United States Patent
Hansen et al.

(10) Patent No.: US 10,966,814 B2
(45) Date of Patent: Apr. 6, 2021

(54) PROSTHETIC AUGMENTS TO IMPROVE MUSCLE MECHANICS

(71) Applicants: Matthew Hansen, Gilbert, AZ (US); Christopher P. Roche, Gainesville, FL (US)

(72) Inventors: Matthew Hansen, Gilbert, AZ (US); Christopher P. Roche, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 0 days.

(21) Appl. No.: 15/024,730

(22) PCT Filed: Sep. 26, 2014

(86) PCT No.: PCT/US2014/057609
§ 371 (c)(1),
(2) Date: Mar. 24, 2016

(87) PCT Pub. No.: WO2015/048385
PCT Pub. Date: Apr. 2, 2015

(65) Prior Publication Data
US 2016/0228234 A1    Aug. 11, 2016

Related U.S. Application Data

(60) Provisional application No. 61/882,806, filed on Sep. 26, 2013.

(51) Int. Cl.
*A61F 2/08* (2006.01)
*A61B 17/56* (2006.01)
(Continued)

(52) U.S. Cl.
CPC ................ *A61F 2/08* (2013.01); *A61B 17/56* (2013.01); *A61F 2/0811* (2013.01);
(Continued)

(58) Field of Classification Search
CPC ...... A61F 2/08; A61F 2/0811; A61F 2/30734; A61F 2/30736; A61F 2002/0894;
(Continued)

(56) References Cited

U.S. PATENT DOCUMENTS

| | | | | |
|---|---|---|---|---|
| 6,468,278 B1 * | 10/2002 | Muckter | ............ | A61B 17/8061 606/291 |
| 2013/0150977 A1 | 6/2013 | Gabriel et al. | | |

(Continued)

FOREIGN PATENT DOCUMENTS

| | | |
|---|---|---|
| EP | 2452641 A1 | 5/2012 |
| WO | 2009018365 A1 | 2/2009 |
| WO | 2011025959 A1 | 3/2011 |

OTHER PUBLICATIONS

International Search Report for International Application No. PCT/US2014/057609, dated Jan. 5, 2015.

*Primary Examiner* — Suba Ganesan
(74) *Attorney, Agent, or Firm* — Greenberg Traurig, LLP

(57) ABSTRACT

Prosthetic augments to improve muscle mechanics are disclosed herein. A prosthetic augment of the present disclosure includes an augment member configured to engage a bone, the augment member having a first face adapted for contacting the bone; and a second face adapted for contacting an underside of a muscle, wherein at least a portion of the second face includes a bulbous surface adapted to alter a wrapping angle of the muscle around the bone, wherein a first thickness is defined between the first face and the second face at a first position on the augment member, wherein a second thickness is defined between the first face and the bulbous surface of the second face, and wherein the first thickness and the second thickness are not equivalent so as to result in the augment member having a non-uniform thickness.

13 Claims, 44 Drawing Sheets

(51) Int. Cl.
    *A61F 2/30* (2006.01)
    *A61F 2/40* (2006.01)
(52) U.S. Cl.
    CPC ... *A61F 2/30739* (2013.01); *A61F 2002/4022* (2013.01); *A61F 2002/4066* (2013.01); *A61F 2220/0008* (2013.01)
(58) Field of Classification Search
    CPC .......... A61F 2002/4088; A61F 2/30756; A61F 2/30738; A61B 17/6425; A61B 2017/567
    See application file for complete search history.

(56) References Cited

U.S. PATENT DOCUMENTS

2013/0211521 A1\* 8/2013 Shenoy ................. A61B 17/56
                                                          623/13.12
2017/0027708 A1\* 2/2017 Shenoy ................. A61B 17/56

\* cited by examiner

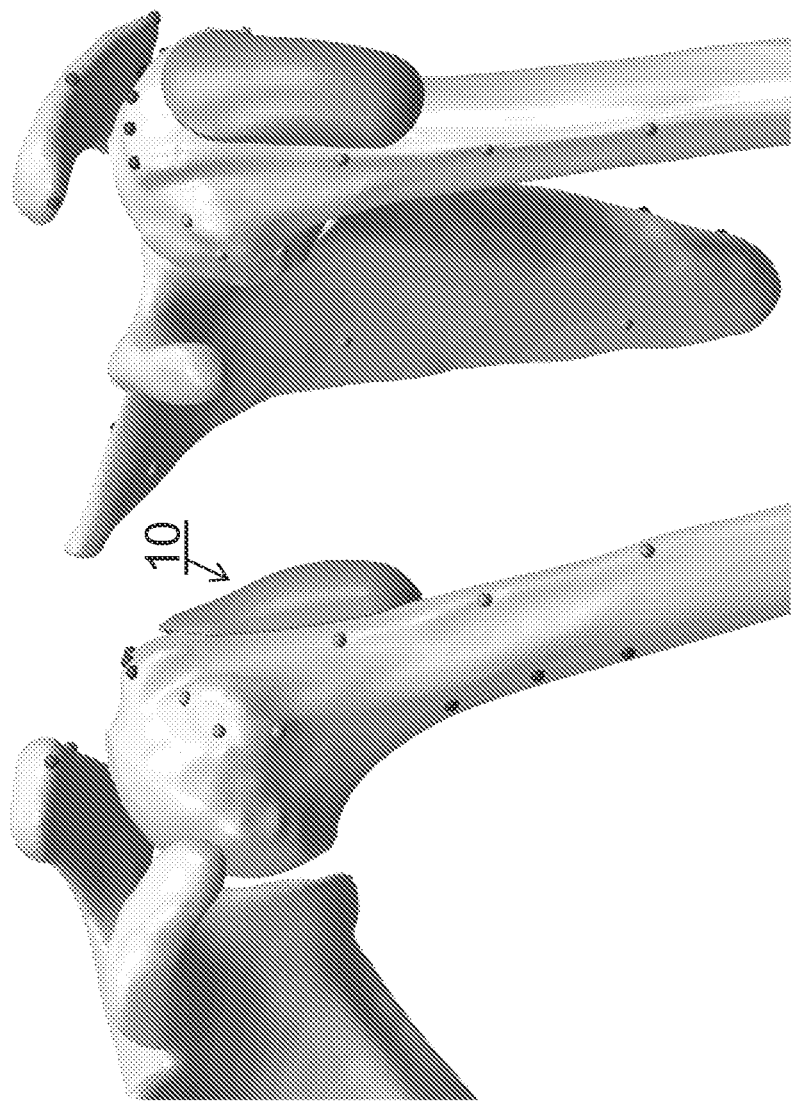

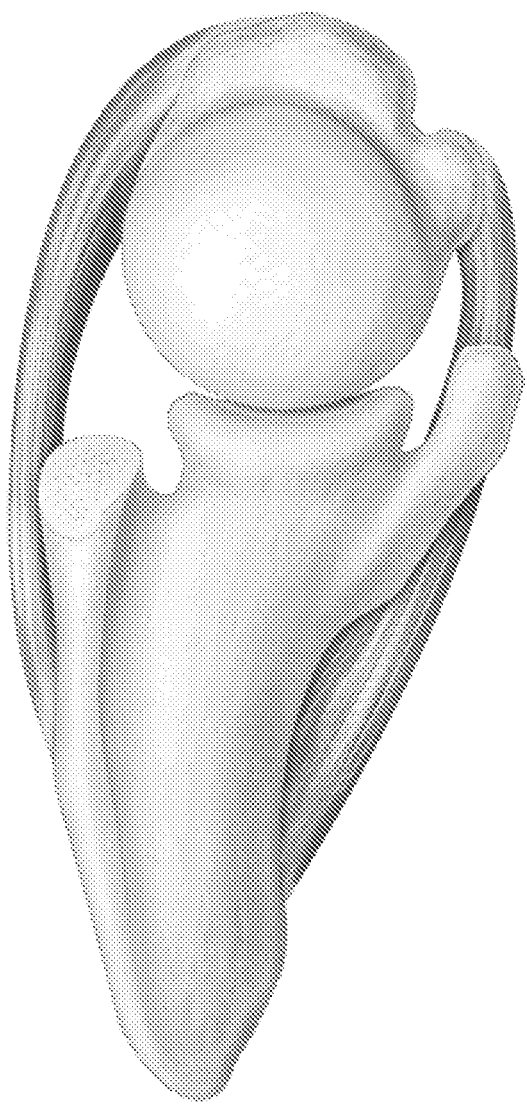
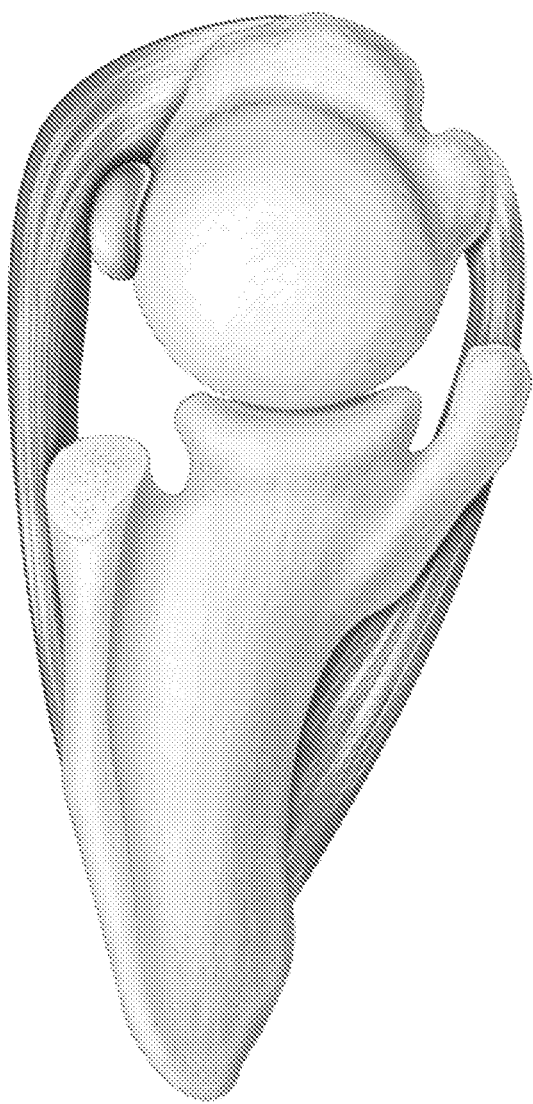
FIG. 15A
FIG. 15B

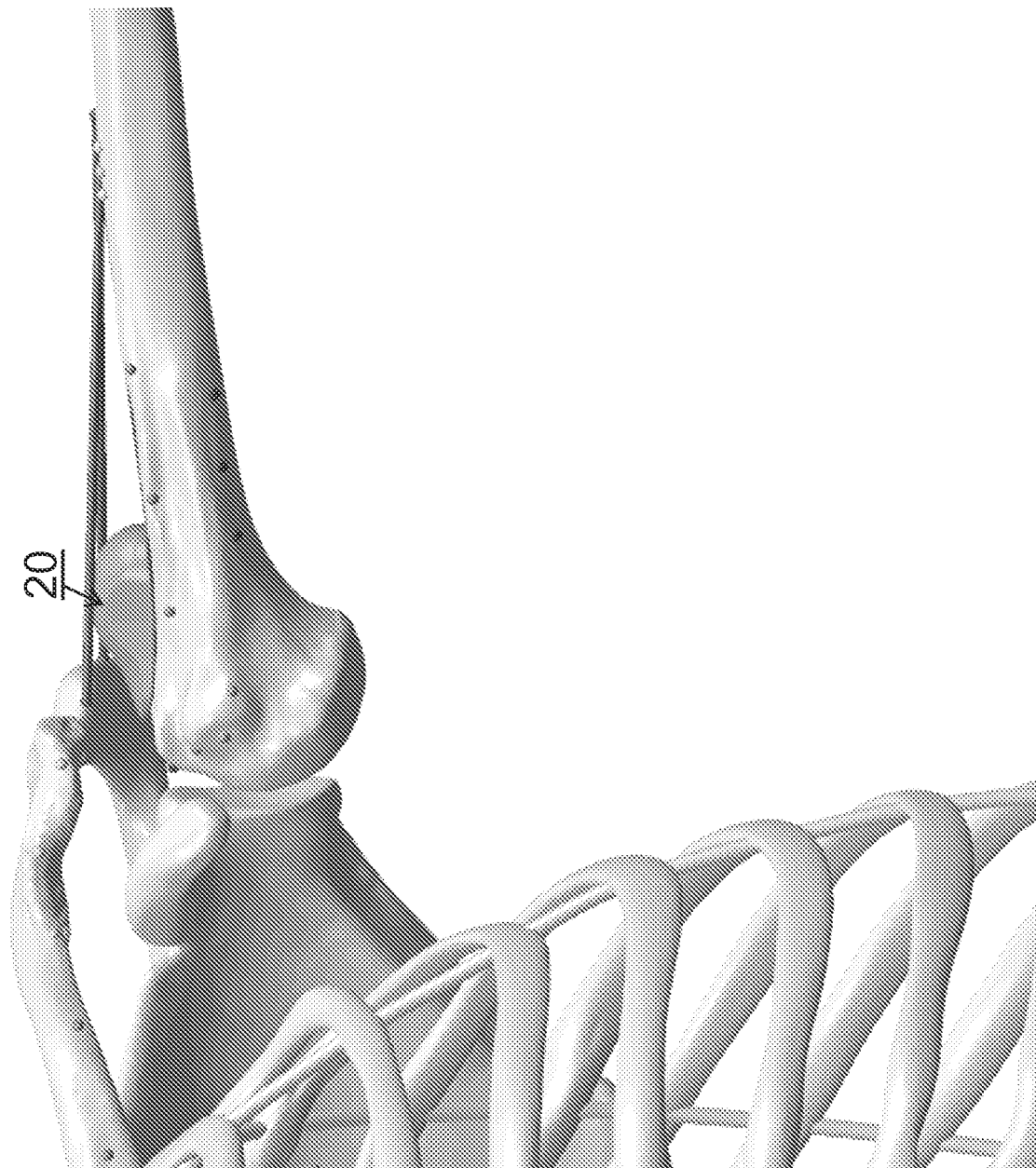

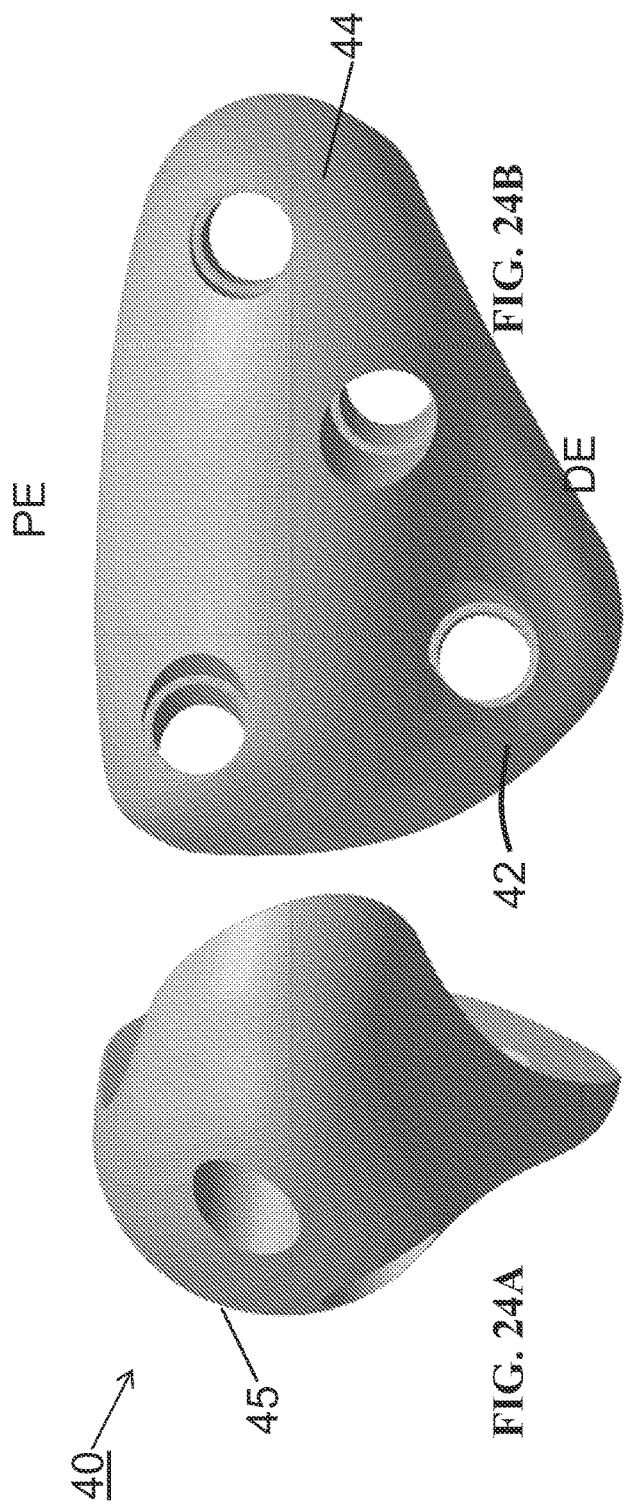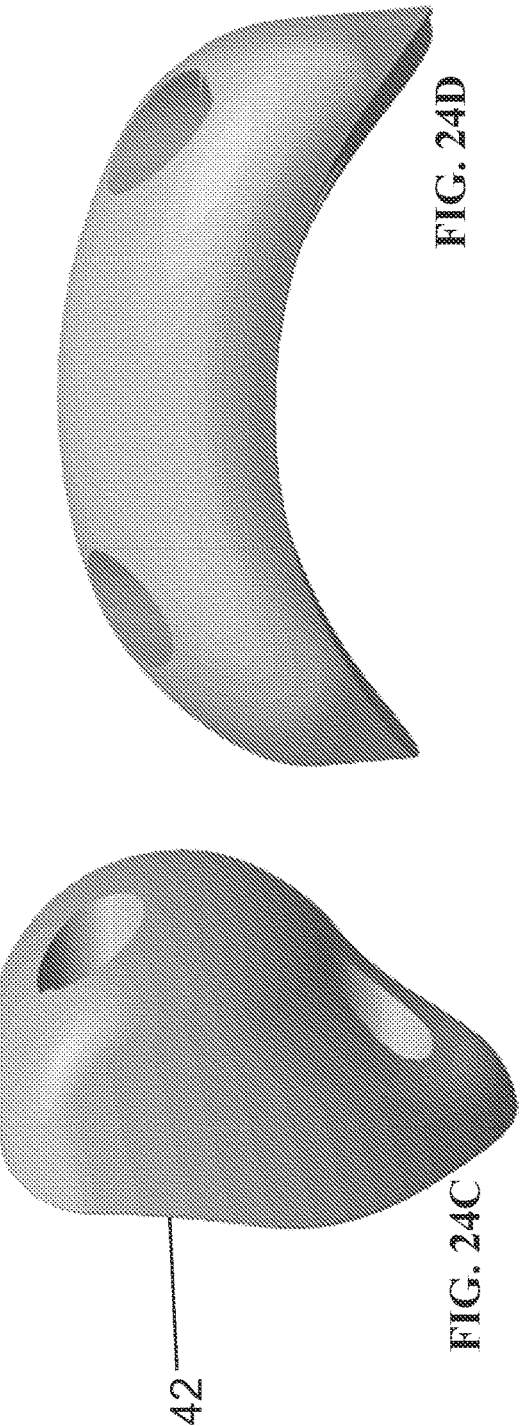

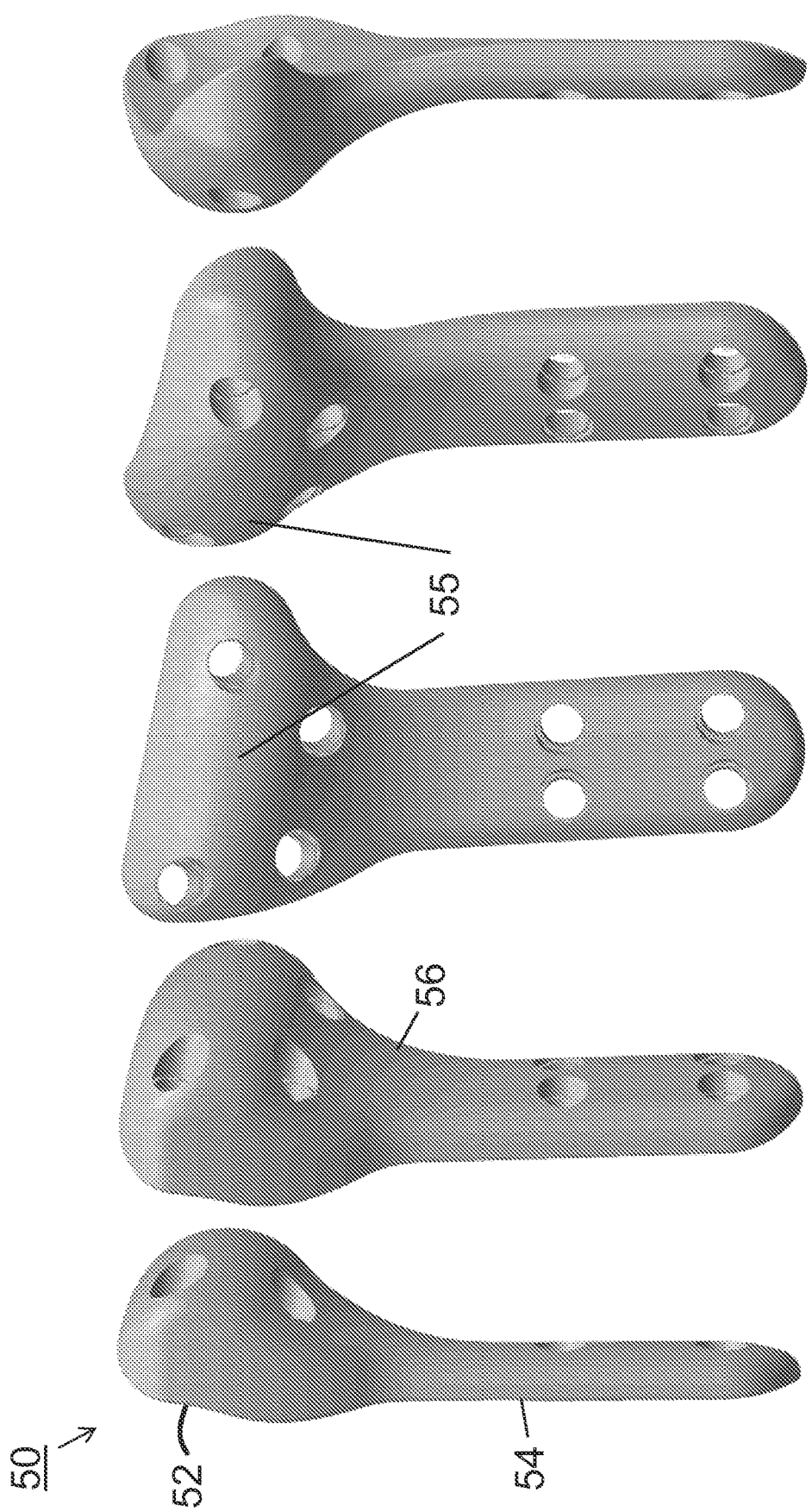

PROSTHETIC AUGMENTS TO IMPROVE MUSCLE MECHANICS

RELATED APPLICATION

This application is a national stage application of PCT/US14/57609, filed Sep. 26, 2014, and claims priority of U.S. Provisional Patent Application Ser. No. 61/882,806, Filed on Sep. 26, 2013, the contents of which are hereby incorporated by reference in their entirety.

BACKGROUND

Muscles generate straight line forces that are converted to torques in proportion to their perpendicular distance between the joint center of rotation (CoR) and the muscle's line of action. This perpendicular distance is termed the muscle moment arm; thus, a 50% larger moment arm implies a 50% lower force required by a particular muscle to induce a given torque/motion. The location of the moment arm relative to the joint center of rotation determines the type of motion the muscle will create. In the shoulder, these motions are abduction/adduction (in the scapular/coronal plane and/or in the transverse plane), internal/external rotation (rotation of long axis of humerus), and flexion/extension (in the sagittal plane). The greater the muscle's moment arm, the greater capacity for that muscle to generate the torque required for motion and to support external loads. The tradeoff for a larger moment arm is that the muscle then requires a greater excursion (i.e. more muscle shortening to generate a given amount of motion). It should be recognized that a muscle's moment arm is only one component of a muscle's ability to generate torque, other factors include the muscle's physiologic cross sectional area, architecture, neural activity, and its length-tension relationship.

The deltoid is the largest and most important muscle in the shoulder girdle. It is the primary mover in the shoulder, and generates forward elevation in the scapular plane. The deltoid consists of three distinct heads: 1) anterior (anterior acromion and clavicle), 2) middle (lateral margin of the acromion), and 3) the posterior deltoid (scapular spine); and accounts for approximately 20% of the mass of the shoulder muscles. At low levels of abduction, the wrapping of the middle deltoid around the greater tuberosity of the humeral head (FIG. 1) generates a stabilizing compressive force; however, this compressive force is small relative to that generated by the rotator cuff.

Changing the joint center of rotation with arthroplasty (specifically, with a reverse shoulder in which the inversion of the anatomic concavities and the inferior and medial shift of the center of rotation) dramatically alters the relationship of each (shoulder) muscle to its normal physiologic function. In the shoulder, medially shifting the center of rotation increases the length of the anterior, middle, and posterior deltoid abduction moment arms and lengthens the anterior, middle, and posterior deltoid allowing them to contribute more toward abduction. These larger abductor moment arms enhance the capacity of the deltoid to elevate the arm in the scapular and coronal planes, compensating for the impaired function of the supraspinatus and the superior portions of the subscapularis and infraspinatus rotator cuff muscles which are typically involved in the indicated pathology. Medially shifting the center of rotation also translates the humerus medially which increases the laxity of any remaining rotator cuff muscles and also leads to impingement of the humerus with the scapular neck at low elevation (i.e. scapular notching).

Restoring the lateral position of the humeral tuberosities is important to tension the remaining rotator cuff muscles in a more natural physiologic manner and offers the potential to better restore rotational strength. While over-tensioning these muscles may offer the possibility of improved resting tone/tension, it may also make it more difficult to repair following tenotomy (in the case of the subscapularis).

In reverse total shoulder replacement arthroplasty, lateralizing the joint center of rotation lateralizes the humerus, tensions the remaining rotator cuff muscles, and minimizes impingement of the humeral component along the inferior scapular neck. Lateralizing the joint center of rotation also increases the torque on the glenoid fixation surface and decreases the lengths of the deltoid abductor moment arms. Because the deltoid abductor moment arms are decreased as the center of rotation is lateralized, the deltoid becomes less effective as an abductor and requires a greater force to elevate the arm in both the scapular and coronal planes. These elevated loads and torques can have negative implications on patient rehab, muscle fatigue, stress fractures, and prosthesis fixation.

SUMMARY

Prosthetic augments to improve muscle mechanics are disclosed herein. In an embodiment, "improve muscle mechanics" means the ability to increase a muscle's moment arm, and/or increase the muscle's length/tension, and/or alter the muscle's line of action, and/or increase the muscle's wrapping.

According to aspects illustrated herein, there is disclosed a prosthetic augment that includes an augment member configured to engage a bone, the augment member having a first face adapted for contacting the bone; and a second face adapted for contacting an underside of a muscle, wherein at least a portion of the second face includes a bulbous surface adapted to alter a wrapping angle of the muscle around the bone, and wherein the second face has a radius of curvature selected from one of a constant radius of curvature or a variable radius of curvature. In an embodiment, the second face has a constant radius and the bulbous surface is a sphere. In an embodiment, the second face has a variable radius of curvature and the bulbous surface is sufficiently elongated to accommodate the anatomic variance of the bone. In an embodiment where the bulbous surface is sufficiently elongated, a first thickness is defined between the first face and the second face at a first position on the augment member, the first thickness ranging from about 1 mm to less than about 5 mm, and a second thickness is defined between the first face and the bulbous surface of the second face, the second thickness ranging from about 7 mm to about 50 mm.

According to aspects illustrated herein, there is disclosed a prosthetic augment that includes an augment member configured to engage a bone, the augment member having a first face adapted for contacting the bone; and a second face adapted for contacting an underside of a muscle, wherein at least a portion of the second face includes a bulbous surface adapted to alter a wrapping angle of the muscle around the bone, wherein a first thickness is defined between the first face and the second face at a first position on the augment member, and wherein the first thickness ranges from about 1 mm to less than about 5 mm, wherein a second thickness is defined between the first face and the bulbous surface of the second face, and wherein the second thickness ranges from about 7 mm to about 50 mm, and wherein the first thickness and the second thickness are not equivalent so as to result in the augment member having a non-uniform thickness.

According to aspects illustrated herein, there is disclosed a prosthetic augment comprising an augment member configured to extend a length and/or a width of a patient's bone, the augment member having a first face adapted for receiving contact with the bone of the patient and a second face adapted for receiving contact with an underside of a muscle of the patient, the augment member having a proximal end toward a head of the patient and a distal end toward a hip of the patient, wherein the augment member includes a rounded portion resulting in a thickness of the augment member being non-uniform from the distal end to the proximal end.

According to aspects illustrated herein, there is disclosed a kit for a long bone that includes a prosthetic augment of the present disclosure and at least one locking bone screw.

According to aspects illustrated herein, there is disclosed a method that includes positioning a prosthetic augment of the present disclosure between a bone and a muscle that wraps the bone; and engaging at least a portion of the first face of the augment member with the bone, wherein the bulbous surface of the second face is adapted to: (i) alter muscle wrapping around the bone, and (i) increase a moment arm of the muscle. In an embodiment, the augment member is engaged to the bone such that a center of rotation of the bulbous surface of the augment member approaches that of a native joint. In an embodiment, the augment member is engaged to the bone such that a center of rotation of the bulbous surface of the augment member approaches that of a native joint and compression of the wrapping muscle results in a stabilizing force. In an embodiment, the bone is a proximal humerus, and wherein the muscle is a deltoid muscle. In an embodiment, the bone is a posterior humerus, and wherein the muscle is a posterior rotator cuff muscle. In an embodiment, the posterior rotator cuff muscle is selected from one of infraspinatus or teres minor. In an embodiment, the bone is an anterior humerus, and wherein the muscle is an anterior shoulder muscle. In an embodiment, the anterior shoulder muscle is selected from the group consisting of subscapularis, teres major, pectoralis and latissimus. In an embodiment, the method is performed during anatomic shoulder arthroplasty. In an embodiment, the method is performed during reverse shoulder arthroplasty. In an embodiment, the method is performed during knee arthroplasty. In an embodiment, the method is performed during hip arthroplasty.

In an embodiment, a prosthetic augment of the present disclosure is sufficiently designed and adapted for increasing the tension of a particular muscle of the patient. Muscle tension can be measured by looking at the change in the length of the lines simulating the muscles. In this disclosure, a computer model of the shoulder joint was used and the native shoulder was assumed to be the normal muscle length. In the computer model of this disclosure, after a specific device was implanted, if the length of the line shortened relative to the same muscle length for the anatomic shoulder without the augment, than that simulated muscle was deemed to be shortened. Conversely, in the computer model of this disclosure, after a specific device was implanted, if the length of the line got longer relative to the same muscle length for the anatomic shoulder without the augment, than that simulated muscle was deemed to be lengthened.

In an embodiment, a prosthetic augment of the present disclosure is sufficiently designed and adapted for increasing the moment arm of a particular muscle so as to result in lower force required by the muscle to induce a given torque/motion. Moment arm can be measured as the perpendicular distance between the line of action of the muscle and the center of rotation of the joint. The augments of the present disclosure have been shown to lateralize the muscle, while the center of rotation of the shoulder joint remains the same. Thus, the perpendicular distance between the line of action of the muscle and the center of rotation of the shoulder joint increases, resulting in an increase in the muscle abductor moment arm.

In an embodiment, a prosthetic augment of the present disclosure is sufficiently designed and adapted to facilitate greater muscle wrapping to impart increased joint stability. In an embodiment, a prosthetic augment of the present disclosure connects to a patient's humerus along the lateral tuberosity of the proximal humerus, underneath the deltoid (e.g. inferior to the rotator cuff, posterior to the teres major, pectoralis major, and latissimus dorsi, anterior to the triceps, and proximal to the axillary nerve).

In an embodiment, a prosthetic augment of the present disclosure includes a second face with a bulbous surface sufficiently designed, when implanted into a patient, to result in an increased deltoid moment arm. In an embodiment, a prosthetic augment of the present disclosure includes a second face with a bulbous surface sufficiently designed, when implanted into a patient, to lower the deltoid force required to elevate (abduct) the arm.

According to aspects illustrated herein, there is disclosed an implant system that includes a prosthetic augment comprising an augment member configured to extend a length of a patient's bone, the augment member having a first face adapted for receiving contact with the bone of the patient and a second face adapted for receiving contact with the underbelly of a muscle of the patient, the augment member having a proximal end toward a head of the patient and a distal end toward a hip of the patient, wherein the augment member includes a bulbous surface resulting in a thickness of the augment member being non-uniform from the distal end to the proximal end; and a reverse shoulder prosthesis. In an embodiment, the reverse shoulder prosthesis includes one or more of the following components: a humeral stem, a humeral adapter tray configured to sit near a resected surface of a humerus; a humeral liner; a glenoid baseplate; and a glenosphere.

In an embodiment, a prosthetic augment of the present disclosure can be used in tandem with a reverse shoulder prosthesis and includes a second face with a bulbous surface sufficiently designed so as to result in an improved deltoid moment arm and deltoid wrapping. In an embodiment, a prosthetic augment of the present disclosure can be used in tandem with a reverse shoulder prosthesis design and includes a second face with a bulbous surface sufficiently designed so as to result in positioning the deltoid sufficiently lateral to impart greater stability to the shoulder joint.

In an embodiment, a prosthetic augment of the present disclosure can be used with the native shoulder or with shoulder arthroplasty (anatomic or reverse). In an embodiment, the use of a prosthetic augment of the present disclosure in a normal shoulder joint results in an increase in the deltoid wrapping angle by as much as 51° as compared to a normal shoulder joint without the prosthetic augment. In an embodiment, the use of a prosthetic augment of the present disclosure in a Grammont reverse shoulder joint results in an increase in the deltoid wrapping angle by as much as 44° as compared to a Grammont reverse shoulder joint without the prosthetic augment. In an embodiment, the use of a prosthetic augment of the present disclosure in an Encore Reverse® shoulder joint results in an increase in the deltoid wrapping angle by as much as 62° as compared to an Encore Reverse® shoulder joint without the prosthetic augment. In an embodiment, the use of a prosthetic augment of the present disclosure in an Equinoxe® reverse shoulder joint results in an increase in the deltoid wrapping angle by as much as 41° as compared to an Equinoxe® reverse shoulder joint without the prosthetic augment.

In another embodiment, a prosthetic augment of the present disclosure is sufficiently designed to attach directly to a patient's muscle (specifically, the deltoid) rather than the patient's bone, and glide over/contact with the bone (specifically, the lateral humerus to maintain the lateral muscle position throughout motion (specifically, arm elevation), thereby increasing the muscle wrapping and moment arm throughout the motion.

According to aspects illustrated herein, a prosthetic augment of the present disclosure can be used in a shoulder joint. In an embodiment, the shoulder joint can be a patient's native shoulder joint. In an embodiment, the shoulder joint can be an anatomic shoulder arthroplasty. In an embodiment, the shoulder joint can be a reverse shoulder arthroplasty. While a prosthetic tuberosity augment of the present disclosure is intended for use in the shoulder (with or without arthroplasty), a prosthetic augment has applications in other joints as well, including the hip, knee, ankle, and spine (with or without arthroplasty) and/or any site where muscles span a joint.

According to aspects illustrated herein, there is disclosed a prosthetic augment that increases the deltoid moment arm. For an intact shoulder, a prosthetic deltoid augment of the present invention may be beneficial in clinical cases of deltoid weakness and rotator cuff weakness. In an embodiment, by decreasing the rotator cuff force required for abduction it may be able to substitute for rotator cuff repair. For anatomic total shoulder replacements, a prosthetic deltoid augment of the present invention may increase the life of the prosthesis by decreasing the joint reaction force and thus decreasing polyethylene wear. In the setting of reverse shoulder arthroplasty (RSA), a prosthetic deltoid augment of the present invention may improve deltoid strength, particularly for those prostheses with a medial glenoid combined with medial humerus design. In revisions of RSA for instability, simply implanting a prosthetic deltoid augment of the present invention rather than replacing the prosthesis may be possible as the prosthetic deltoid augment may be used to tension the deltoid independent of the rotator cuff; thereby, restoring stability to the joint.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIGS. 9A and 9B show the prosthetic tuberosity augment of FIGS. 8A-8D positioned on a lateral humerus.

FIGS. 15A and 15B are drawings of a normal shoulder. FIG. 15A depicts the normal shoulder without a tuberosity augment on the posterior portion of the greater tuberosity; FIG. 15B depicts the normal shoulder with a tuberosity augment positioned on the posterior humerus, underneath the posterior rotator cuff muscles (infraspinatus and teres minor) to posteriorly shift their position and line of action in order to increase their moment arms (bottom).

FIG. 16A depicts the Equinoxe® reverse shoulder without a tuberosity augment on the posterior portion of the greater tuberosity; FIG. 16B depicts the Equinoxe® reverse shoulder with a tuberosity augment positioned on the posterior humerus, underneath the posterior rotator cuff muscles (infraspinatus and teres minor) with reverse shoulder arthroplasty to posteriorly shift their position and line of action in order to increase their moment arms (bottom).

FIG. 18 is a computer model of a normal shoulder abducted to 99 degrees relative to a fixed scapula in which the middle deltoid no longer wraps the +5 mm expanded tuberosity augment of FIGS. 17A-17D and therefore no longer imparts a stabilizing compressive force to the glenoid.

FIGS. 24A-24D and FIGS. 25A-25D show views of a fourth embodiment of a prosthetic tuberosity augment of the present disclosure for a left humerus (FIGS. 24A-24D) and a right humerus (FIGS. 25A-25D).

FIGS. 27A-27E and FIGS. 28A-28E show views of a sixth embodiment of a prosthetic tuberosity augment of the present disclosure for a left humerus (FIGS. 27A-27E) and a right humerus (FIGS. 28A-28E).

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components (and any size, material and similar details shown in the figures are, of course, intended to be illustrative and not restrictive). Therefore, specific structural and functional details disclosed herein are not to be interpreted as limiting, but merely as a representative basis for teaching one skilled in the art to variously employ the present invention.

Reduced muscle function with arthroplasty is a complicated issue. In the shoulder, prosthetic design parameters can alter the tension of the muscles above or below their normal/native resting length (i.e., the length of the muscles of the native anatomic shoulder in neutral position) and or strategically increase (or decrease) the moment arms of muscles to make them more (or less) important contributor to a given type of motion.

Being able to improve the mechanics of a particular muscle (without impairing any other muscle) by strategically increasing its moment arm or alter its line of action and increase its wrapping may improve function and potentially eliminate the need for muscle transfers; especially in difficult pathologies like rotator cuff tear arthropathy or revision arthroplasty in which reverse shoulder arthroplasty is typically indicated.

Figure 1:
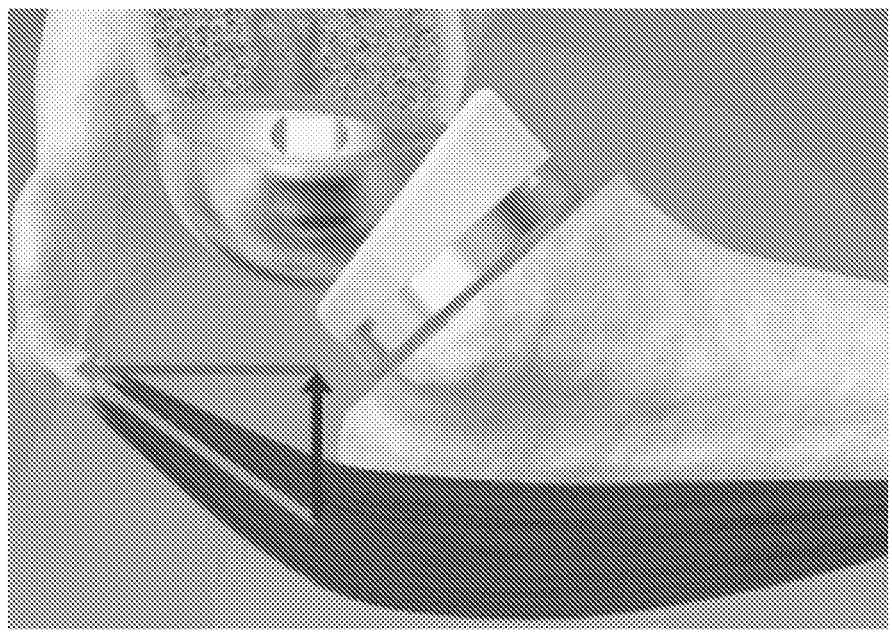
FIG. 1 is a photograph showing the middle deltoid wrapping around the greater tuberosity to increase the stability via humeral head compression.
Figure 2:
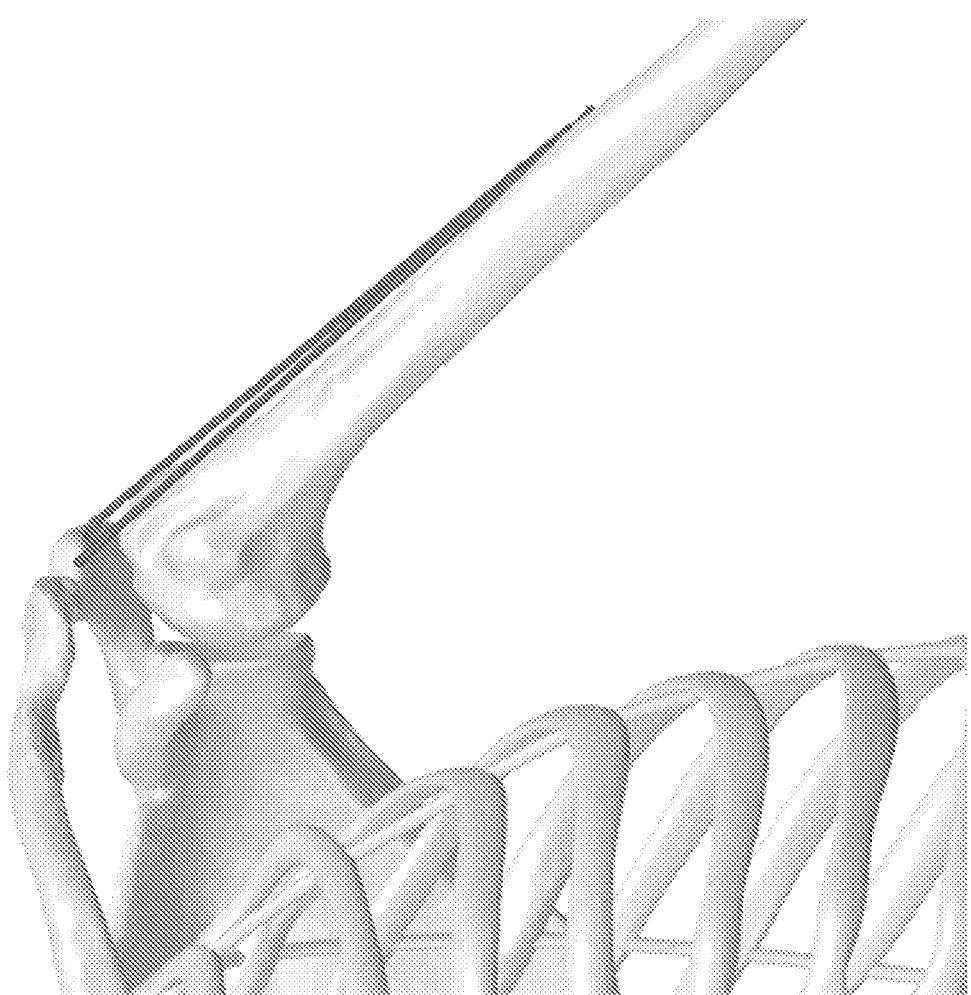
FIG. 2 is a computer model of the normal shoulder abducted to 48 degrees relative to a fixed scapula in which the middle deltoid no longer wraps the greater tuberosity of the humeral head and therefore no longer imparts a stabilizing compressive force to the glenoid.
Figure 3:
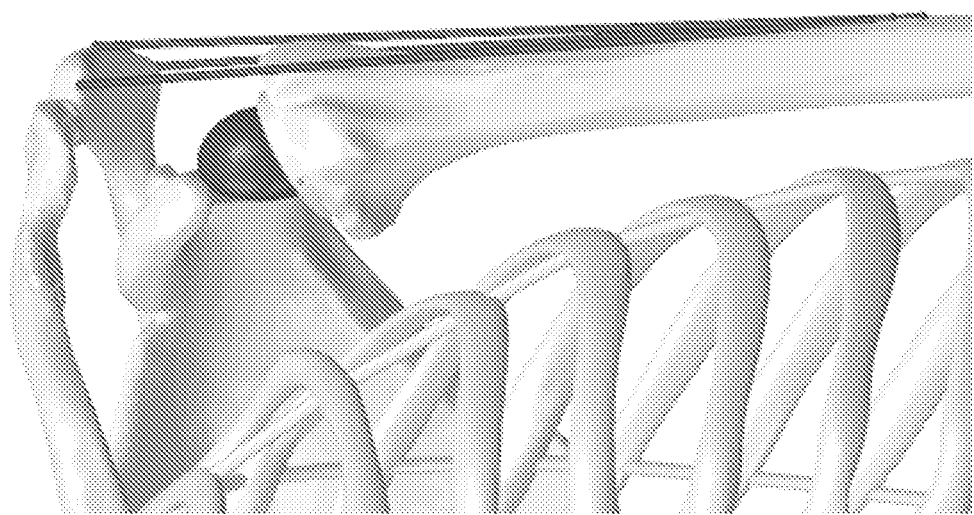
FIG. 3 is a computer model of a 36 mm Grammont reverse shoulder abducted to 8 degrees relative to a fixed scapula in which the middle deltoid no longer wraps the greater tuberosity of the humeral head and therefore no longer imparts a stabilizing compressive force to the glenoid.
Figure 4:
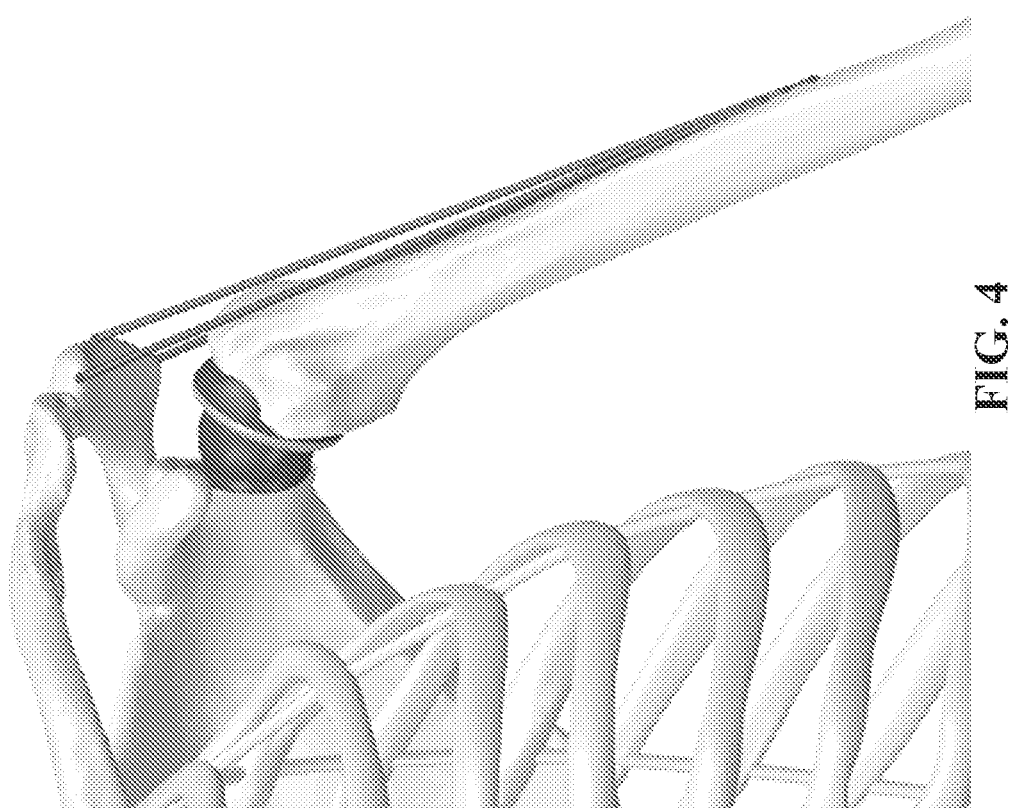
FIG. 4 is a computer model of a 32 mm Encore reverse shoulder abducted to 28 degrees relative to a fixed scapula in which the middle deltoid no longer wraps the greater tuberosity of the humeral head and therefore no longer imparts a stabilizing compressive force to the glenoid.
Figure 5:
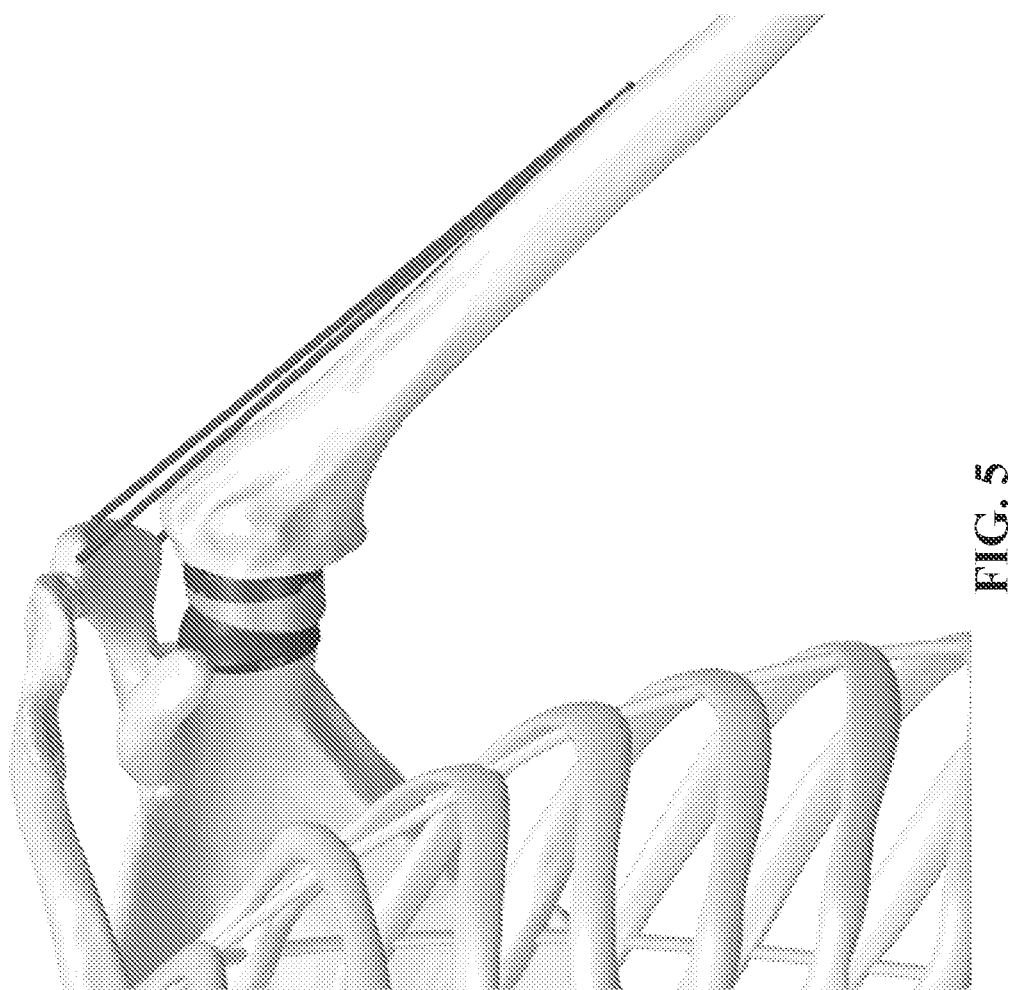
FIG. 5 is a computer model of a 38 mm Equinoxes reverse shoulder abducted to 40 degrees relative to a fixed scapula in which the middle deltoid no longer wraps the greater tuberosity of the humeral head and therefore no longer imparts a stabilizing compressive force to the glenoid.

As described in Table 1 below, deltoid wrapping can be altered by different prosthesis designs (Grammont reverse shoulder, Encore Reverse® shoulder, and Equinoxe® reverse shoulder), different orientations (e.g. changing humeral retroversion and or changing the tilt of the implant), and/or implanting the device in a scapula with varying scapular morphology or wear patterns (e.g. medial glenoid wear). The results presented in Table 1 were calculated from a computer model which simulates muscle lines of action in the shoulder during various arm positions. FIG. 2 is a computer model illustrating the arm abduction in which the middle deltoid ceases to wrap the humeral head greater tuberosity in the normal shoulder (i.e. no prosthesis) at 48° abduction in the scapular plane (relative to a fixed scapula). FIG. 3, FIG. 4 and FIG. 5 are computer models illustrating the same deltoid wrapping phenomenon with varying reverse shoulder prosthesis designs (36 mm Grammont reverse shoulder abducted to 8° relative to a fixed scapula (FIG. 3), 32 mm Encore Reverse® shoulder abducted to 28° relative to a fixed scapula (FIG. 4), and 38 mm Equinoxe® reverse shoulder abducted to 40° relative to a fixed scapula, (FIG. 5)). In FIG. 3, FIG. 4 and FIG. 5, the middle deltoid no longer wraps the greater tuberosity of the humeral head and therefore no longer imparts a stabilizing compressive force to the glenoid.

TABLE 1

Wrapping of Middle Deltoid Around Greater Tuberosity (computer modeling study)

| | Abduction where deltoid doesn't wrap tuberosity |
|---|---|
| Normal Shoulder | 48° |
| 36 Grammont, 20° retroversion | 8° |
| 32 Encore Reverse ®, 20° retroversion | 28° |
| 38 Equinoxe ®, 20° retroversion | 40° |
| 36 Grammont, 0° retroversion | 16° |
| 36 Grammont, 40° retroversion | 7° |
| 36 Grammont, 15° tilt | 7° |
| 32 Encore Reverse ®, 15° tilt | 21° |
| 36 Grammont, 10 mm medial wear | −1° |
| 32 Encore Reverse ®, 10 mm medial wear | 12° |
| 38 Equinoxe ®, 10 mm medial wear | 18° |

Figure 6:
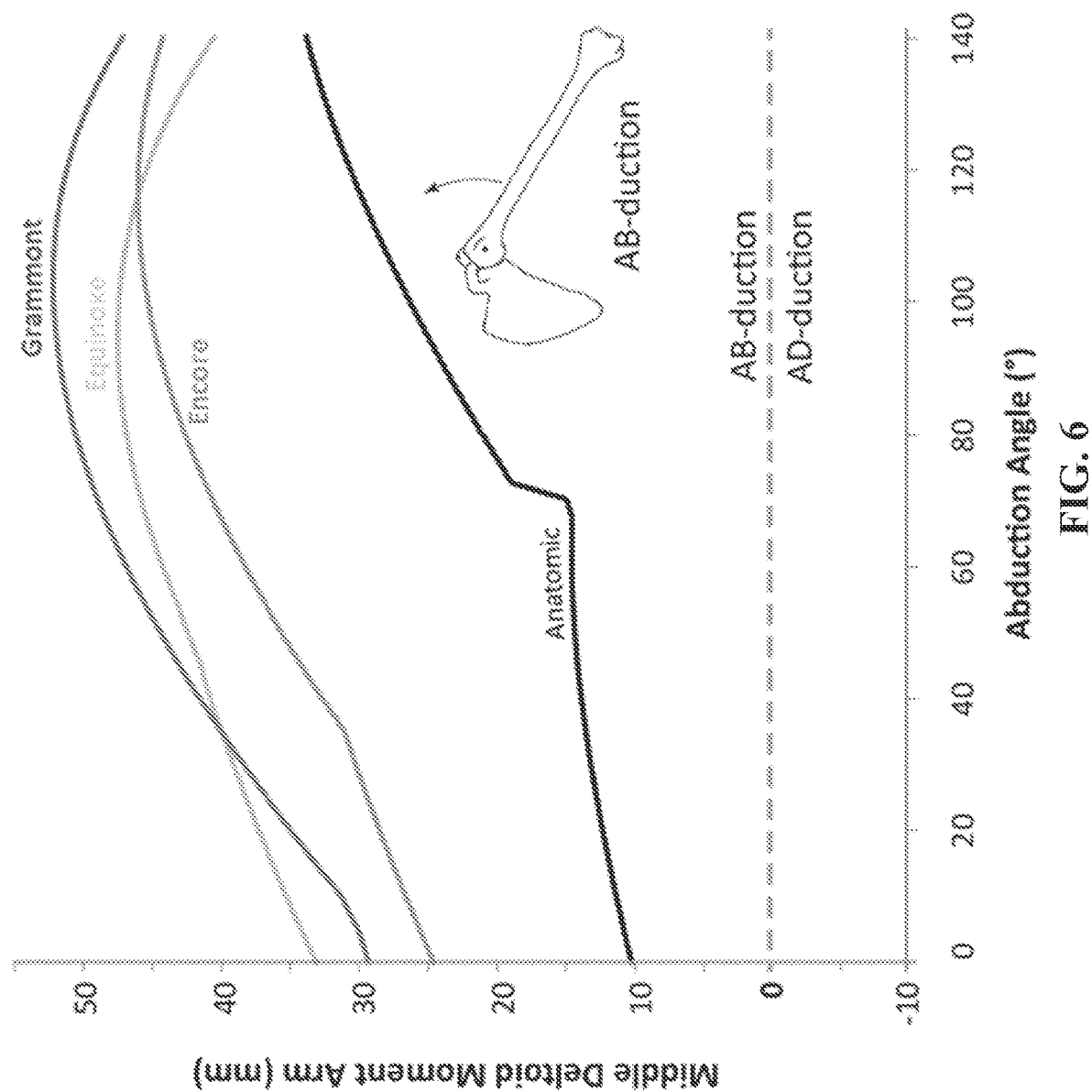
FIG. 6 is a graph showing abduction moment arm for the middle deltoid through 140° of abduction for the normal anatomic shoulder and the 3 aforementioned reverse shoulder designs.
Figure 7A:
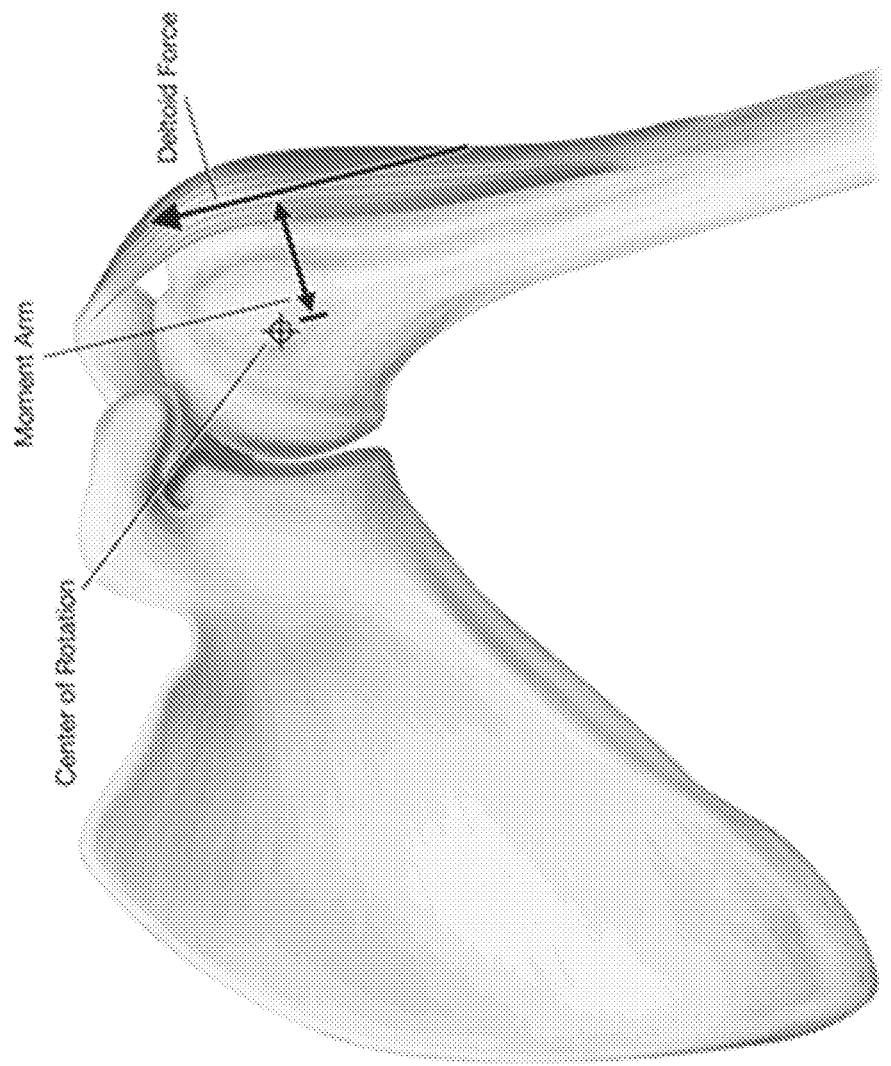
FIGS. 7A-7D are computer models comparing middle deltoid abduction moment arms between the normal shoulder (FIG. 7A) and 3 different reverse shoulder designs: Grammont (FIG. 7B), Encore Reverse® (FIG. 7C), and Equinoxe® (FIG. 7D).
Figure 7B:
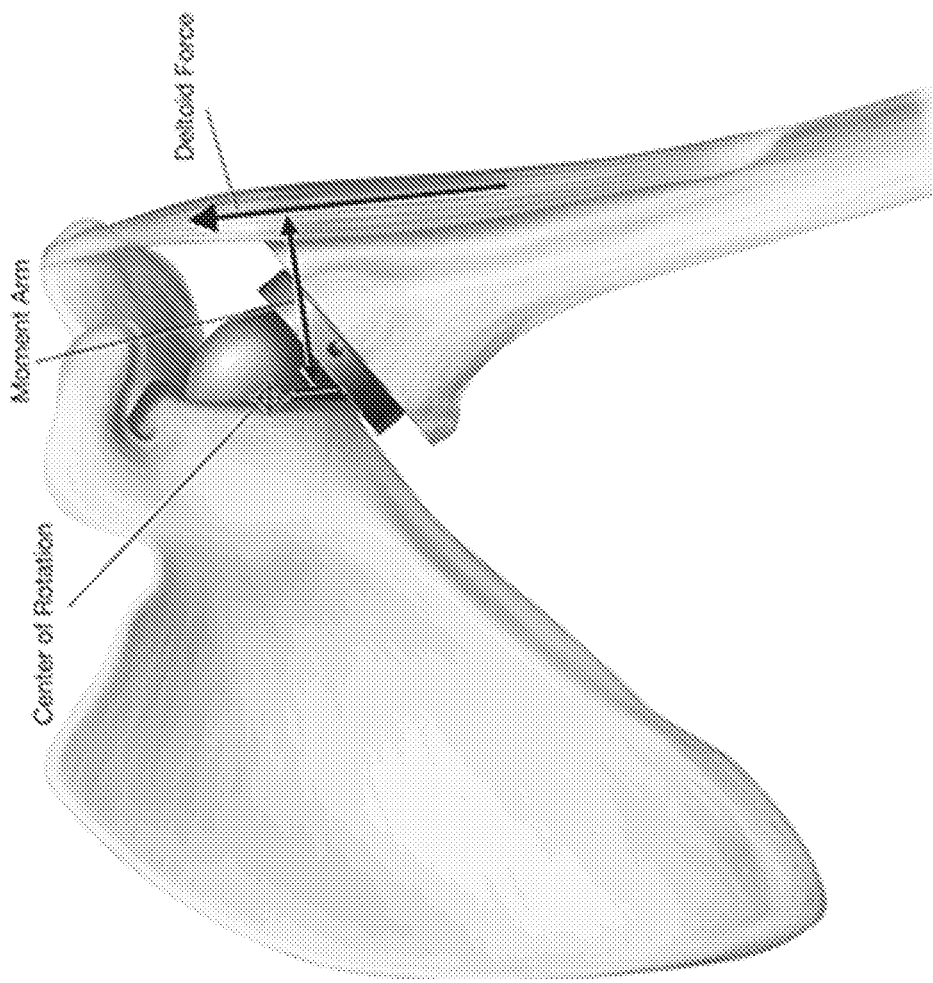
Figure 7C:
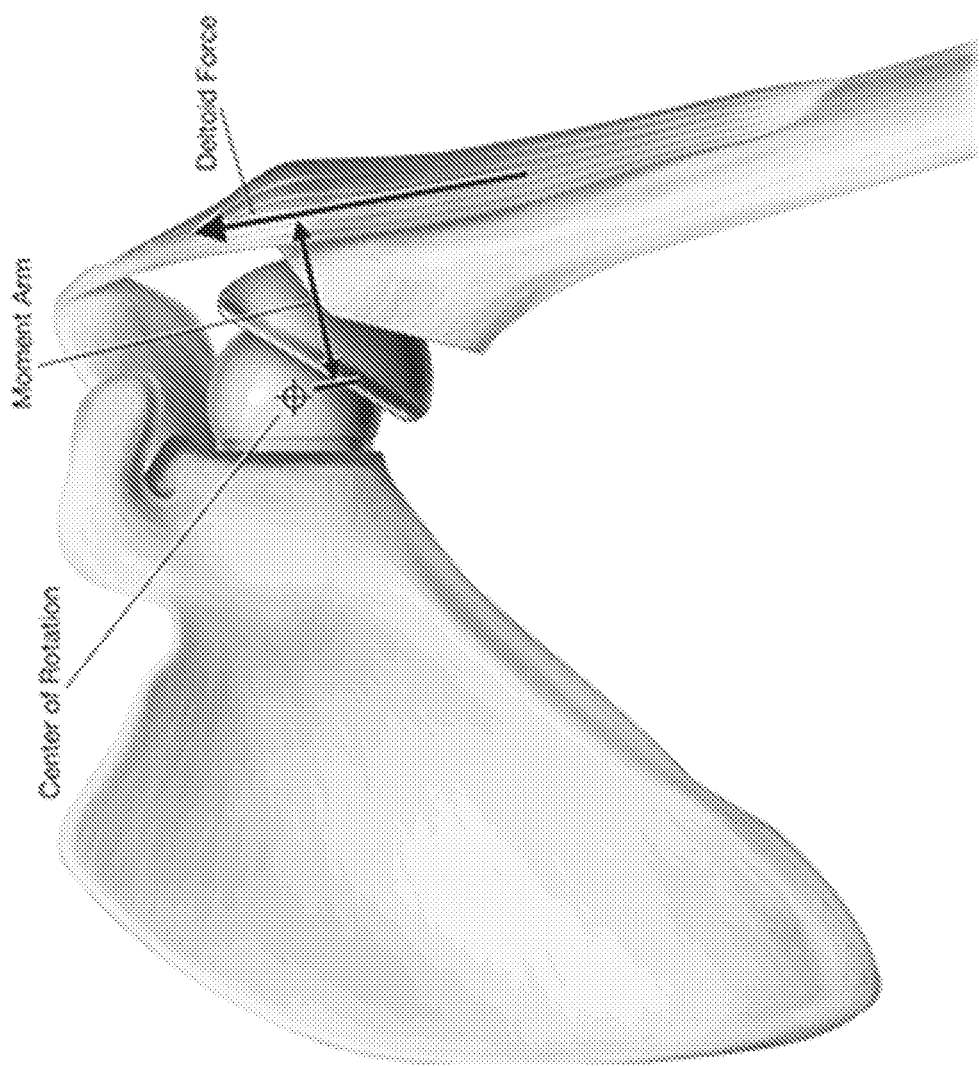
Figure 7D:
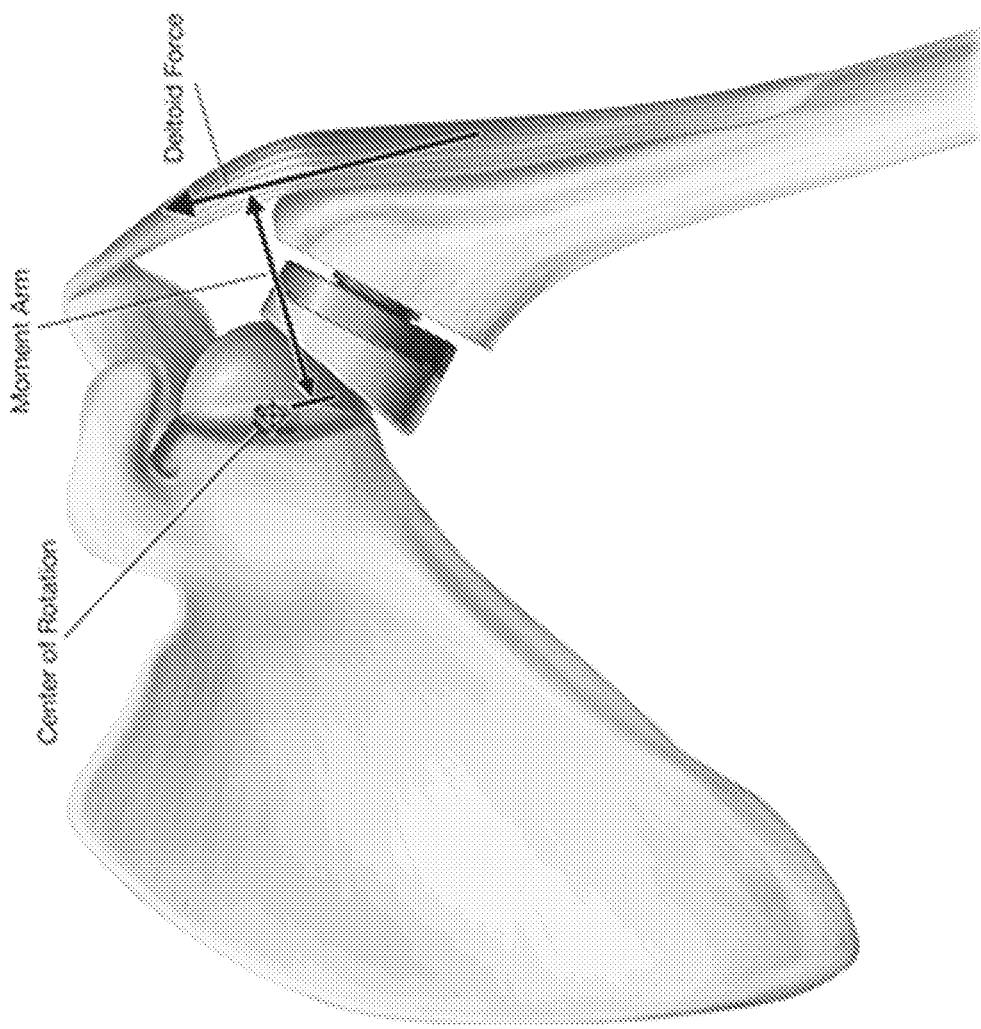

FIG. 6 is a graph showing abduction moment arm for the middle deltoid through 140° of abduction for the normal shoulder and the three aforementioned reverse shoulder prostheses. FIG. 7A, FIG. 7B, FIG. 7C, and FIG. 7D are computer models comparing middle deltoid abduction moment arms between the normal shoulder (FIG. 7A) and 3 different reverse shoulder designs: Grammont (FIG. 7B), Encore Reverse® (FIG. 7C), and Equinoxe® (FIG. 7D). This computer model quantifies the biomechanical impact of 3 commercially available reverse shoulders on the abductor moment arm of seven different muscles during abduction. As illustrated in FIG. 6, FIG. 7A, FIG. 7B, FIG. 7C, and FIG. 7D, the middle deltoid abductor moment arms is significantly increased with reverse shoulder arthroplasty; however, the magnitude of the middle deltoid moment arm is altered by different prosthesis designs (Grammont reverse shoulder, Encore reverse shoulder, vs Equinoxe® reverse shoulder) and changes as a function of humeral elevation. There is a substantial increase in the moment arm for all reverse shoulders compared to the normal shoulder.

FIG. 8A, FIG. 8B, FIG. 8C, and FIG. 8D show four views of a first embodiment of a prosthetic augment 10 of the present disclosure comprising an augment member 12. FIG. 8E, FIG. 8F, and FIG. 8G show three views of the prosthetic augment 10 further comprising locking bone screws 18. In an embodiment, the augment member 12 is a cam/tear-drop shaped, smooth, spherically/splined-curved augment. The augment member 12 is configured to extend a length of a patient's bone, and has a first face 14 adapted for receiving contact with the patient's bone and a second face 16 adapted for receiving contact with the underbelly of a muscle of the patient. The augment member 12 has a proximal end PE toward a head of the patient and a distal end DE toward a hip of the patient. The second face 16 of the augment member 12 includes a bulbous surface 15 resulting in a thickness of the augment member 12 being non-uniform from the distal end DE to the proximal end PE. The bulbous surface 15 is sufficiently elongated to accommodate the anatomic variance of the bone. The second face 16 has a variable radius meaning that at least two different constant radii exist on the second face 16.

Figures 8A, 8B, 8C, 8D:
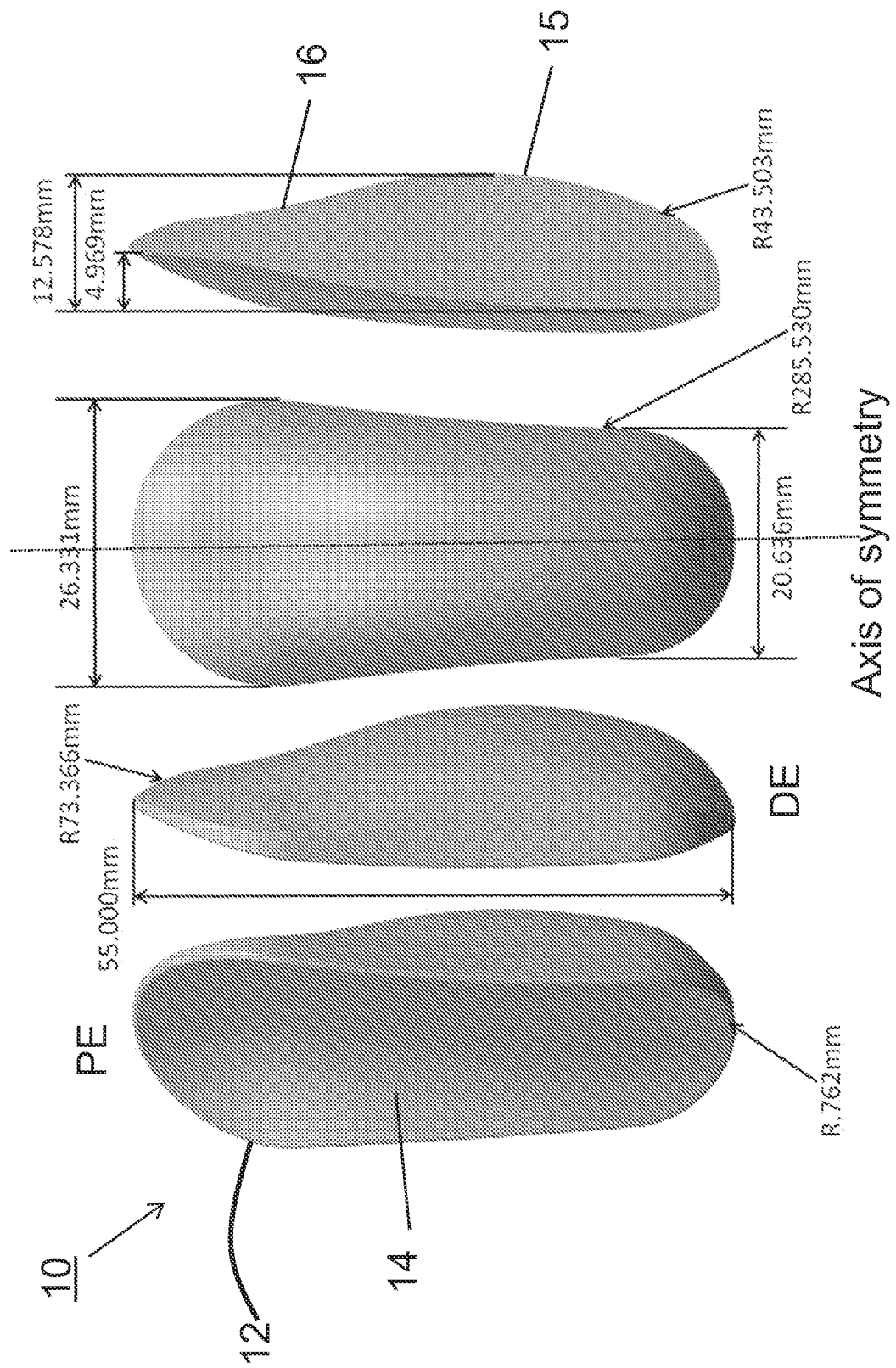
FIGS. 8A-8D show four views of a first embodiment of a cam/tear-drop shaped, smooth, spherically/splined-curved prosthetic tuberosity augment of the present disclosure.
Figure 8G:
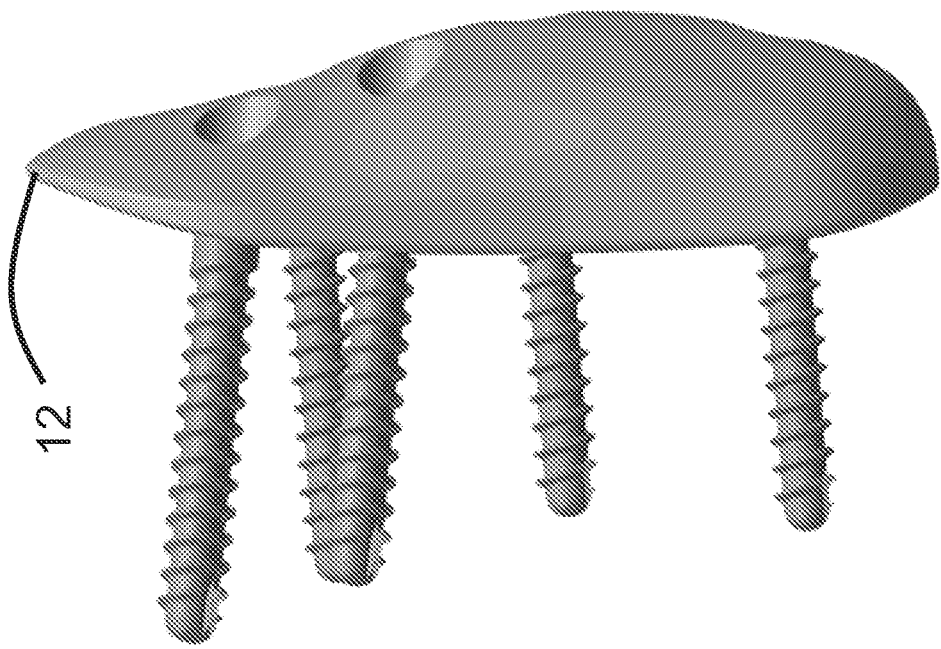
FIGS. 8E-8G show three views of the prosthetic tuberosity augment of FIGS. 8A-8D with locking bone screws.
Figure 8F:
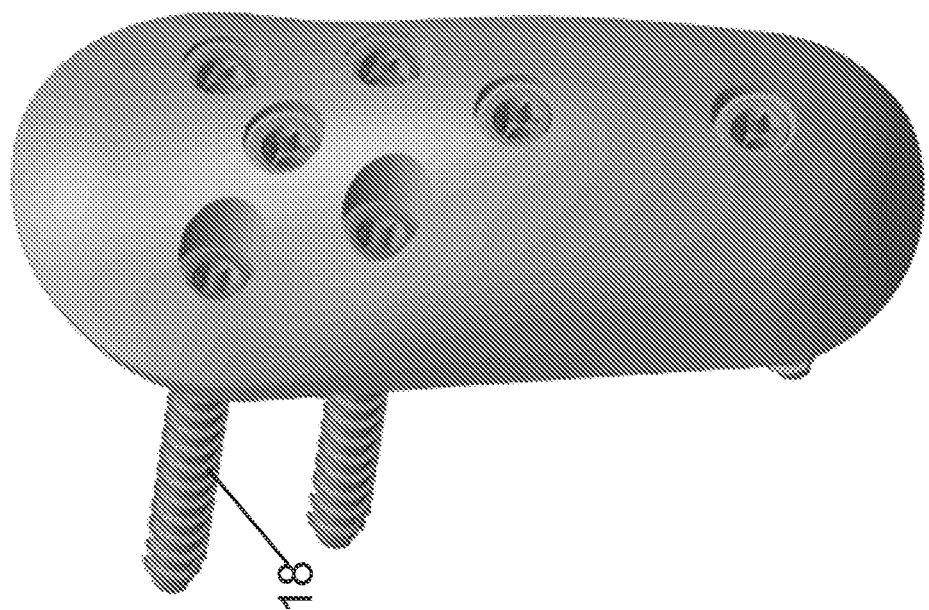
Figure 8E:
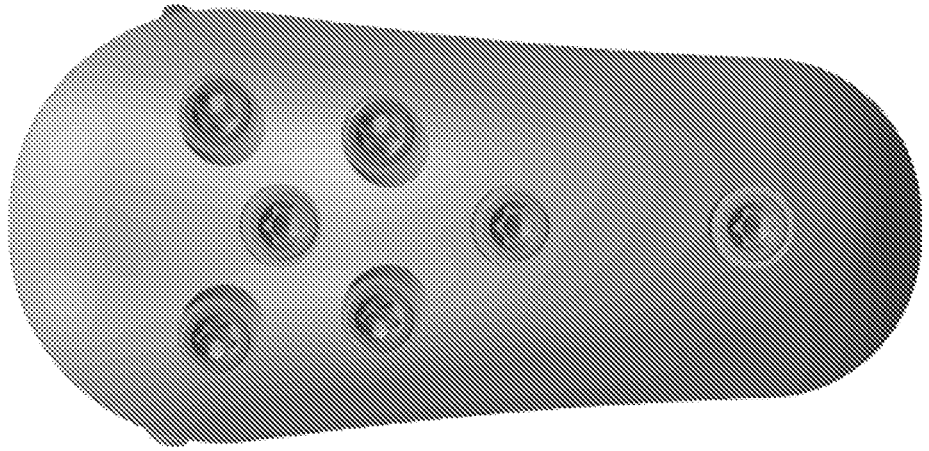

FIG. 8D shows the thickness between first face 14 and second face 16 is non-uniform. A first thickness is defined between the first face 14 and the second face 16 at a first position on the augment member 12. A second thickness is defined between the first face 14 and the bulbous surface 15 of the second face 14. The first thickness and the second thickness are not equivalent so as to result in the augment member 12 having a non-uniform thickness. The augment member 12 comprises variable thicknesses at multiple positions. In an embodiment, the first thickness is less than about 5 mm. In an embodiment, the first thickness ranges from about 1 mm to less than about 5 mm. In an embodiment, the first thickness ranges from about 1 mm to about 4 mm. In an embodiment, the first thickness ranges from about 2 mm to about 3 mm. In an embodiment, the second thickness ranges from above 6 mm to about 50 mm. In an embodiment, the second thickness ranges from about 10 mm to about 46 mm. In an embodiment, the second thickness ranges from about 14 mm to about 42 mm. In an embodiment, the second thickness ranges from about 18 mm to about 38 mm. In an embodiment, the second thickness ranges from about 22 mm to about 34 mm. In an embodiment, the second thickness ranges from about 26 mm to about 30 mm. In an embodiment, the second thickness ranges from about 11 mm to about 19 mm. In an embodiment, the second thickness ranges from about 6 mm to about 40 mm. In an embodiment, the second thickness ranges from about 6 mm to about 30 mm. In an embodiment, the second thickness ranges from about 6 mm to about 20 mm. In an embodiment, the second thickness ranges between about 6 mm to about 10 mm. In an embodiment, the second thickness ranges between about 6.5 mm to about 9.5 mm. In an embodiment, the second thickness ranges between about 7 mm to about 9 mm. In an embodiment, the second thickness ranges between about 7.5 mm to about 8.5 mm.

First face 14 can be contoured (as illustrated) or can be flat. The bulbous surface 15 is sufficiently designed to result in an increase in the wrapping point of a deltoid muscle around the greater tuberosity and also an increase in the abductor moment arm of the deltoid muscle. In an embodiment, the bulbous surface 15 is shaped round to prevent abrasion of the muscle as the augment member 12 fits between the underbelly of the muscle and the lateral humeral bone. The curvature and location of the augment member 12 profile is sufficiently designed so that the center of rotation of the bulbous surface 15 approaches that of the native joint so that the compression of the deltoid muscle will result in a stabilizing force. In an embodiment, the size of the augment member 12 and the amount of lateralization is limited by the impingement that could result with the acromion at high arm elevation. In an embodiment, the superior portion of the augment member 12 is intended to be thin with a thickness so that the augment member 12 can potentially slide under the acromion if placed high or be low profile so that the augment member 12 doesn't impinge.

In an embodiment, the prosthetic augment member 12 has "bilateral" (two-sided) symmetry, because the left and right halves of the augment member 12 mirror each other, allowing the prosthetic augment to be used in left and right bones. The dotted line running down the middle of the augment member 12 is called "the axis of symmetry" In an embodiment, the prosthetic augment can be sufficiently designed to be asymmetric and be provided in lefts and rights in order to better fit the individual patient's anatomy. In an embodiment, an edge of the distal end DE of the augment member 12 is curved. In an embodiment, an edge of the proximal end PE of the augment member 12 is curved. In an embodiment, the augment member 12 ranges from about 20.00 mm to about 50.00 mm in length. In an embodiment, the augment member 12 ranges from about 21.00 mm to about 49.00 mm in length. In an embodiment, the augment member 12 ranges from about 22.00 mm to about 48.00 mm in length. In an embodiment, the augment member 12 ranges from about 23.00 mm to about 47.00 mm in length. In an embodiment, the augment member 12 ranges from about 24.00 mm to about 46.00 mm in length. In an embodiment, the augment member 12 ranges from about 25.00 mm to about 45.00 mm in length. In an embodiment, the augment member 12 ranges from about 26.00 mm to about 44.00 mm in length. In an embodiment, the augment member 12 ranges from about 27.00 mm to about 43.00 mm in length. In an embodiment, the augment member 12 ranges from about 28.00 mm to about 42.00 mm in length. In an embodiment, the augment member 12 ranges from about 29.00 mm to about 41.00 mm in length. In an embodiment, the augment member 12 ranges from about 31.00 mm to about 39.00 mm in length. In an embodiment, the augment member 12 ranges from about 32.00 mm to about 38.00 mm in length. In an embodiment, the augment member 12 ranges from about 33.00 mm to about 37.00 mm in length. In an embodiment, the augment member 12 ranges from about 34.00 mm to about 36.00 mm in length. In an embodiment, the augment member 12 ranges from about 50.00 mm to about 60.00 mm in length. In an embodiment, the augment member 12 ranges from about 51.00 mm to about 59.00 mm in length. In an embodiment, the augment member 12 ranges from about 52.00 mm to about 58.00 mm in length. In an embodiment, the augment member 12 ranges from about 53.00 mm to about 57.00 mm in length. In an embodiment, the augment member 12 ranges from about 54.00 mm to about 56.00 mm in length. In an embodiment, the augment member 12 ranges from about 54.50 mm to about 55.50 mm in length. In an embodiment, the augment member 12 is about 55.00 mm in length.

In an embodiment, a prosthetic augment of the present disclosure is sufficiently designed to attach to a bone and be positioned in a location that strategically increases the tension of a particular muscle. In an embodiment, a prosthetic augment of the present disclosure is sufficiently designed to attach to a bone and individually increases that muscle's moment arm (without a corresponding decrease in the moment arm of the agonist muscle(s)). In an embodiment, a prosthetic augment of the present disclosure is sufficiently designed to attach to a bone and facilitate greater muscle wrapping to impart increased joint stability. Surgeons typically assess joint stability through a trial reduction. If the joint is unstable, the surgeon will try to improve stability by implanting thicker implants. In an anatomic shoulder (in which stability is achieved dynamically with the rotator cuff muscle), surgeons will translate the humerus anteriorly or posteriorly on the glenoid. If the humerus bounces back to the center of the glenoid when they let go of the humerus, than they say the joint is sufficiently stable. However, if the humerus does not bounce back they need to improve stability. In the setting of the reverse shoulder, the surgeon will perform a trial reduction and move the humerus through a few different ranges of motion. If the humeral component "shucks" (e.g. humeral liner comes off the glenosphere inferiorly) more than 3 or 4 mm than the surgeon will replace the implants with thicker humeral liners or bigger diameter glenospheres to tighten the joint. The augments of the present disclosure, in both the anatomic and reverse settings, offer an alternative way to tension the joint in which the deltoid is only lengthened (and not the rotator cuff) when placed on the lateral proximal humerus. In an embodiment, this is advantageous because the deltoid and rotator cuff muscles are relatively fragile muscles and if they are overtensioned too much they can be pain generators and eventually rupture and tear.

In an embodiment, a prosthetic augment of the present disclosure connects to a patient's humerus along the inferior portion of the lateral tuberosity (see, for example FIG. 9A and FIG. 9B), underneath the deltoid (e.g. inferior to the rotator cuff, posterior to the teres major, pectoralis major, and latissimus dorsi, anterior to the triceps, and proximal to the axillary nerve). The location of attachment of the prosthetic augment is sufficiently inferior-lateral to avoid/minimize subacromial impingement during arm elevation. The unique cam/tear-drop shape of the augment member 12 increases the wrapping of the deltoid around the humerus to impart joint compression at greater levels of elevation (as described in Table 1) and also increases the abductor moment arm of the deltoid (increasing the efficiency of the muscle thereby requiring less deltoid force to elevate the arm) while maintaining these increased moment arms at greater levels of elevation (avoiding the decrease in the abductor moment arm with increased elevation as described in FIG. 6). It should be noted that the cam/tear-drop shape may be biased in a particular direction to recruit more or less of a particular muscle for a given motion and/or to increase or decrease the moment arms of a particular muscle; for example, bias the augment member 12 in such a manner to translate the humerus posteriorly to recruit more of the posterior deltoid for external rotation and also increases its abductor moment arm and external rotation moment arm. Conversely, the augment member 12 can be biased in such a manner to translate the humerus anteriorly to recruit more of the anterior deltoid for internal rotation and also increases its abductor moment arm and internal rotation moment arm.

Alternatively (and inversely), the augment member 12 can connect to the patients muscle (specifically, the deltoid) rather than the bone, and glide over/contact with the bone (specifically, the lateral humerus), as occurs anatomically in the knee patella, to maintain the lateral muscle position throughout motion (specifically, arm elevation), thereby increasing the muscle wrapping and moment arm throughout the motion (as described above in Table 1 and FIG. 6).

The augment can be used with the native shoulder or with shoulder arthroplasty (anatomic or reverse) to improve the mechanics of the muscles as described in this disclosure. As this device improves muscle mechanics, it has application in fracture plate implant design and fixation as well. When the tuberosity augment is used with reverse shoulder arthroplasty, the resulting increased deltoid moment arm may sufficiently lower the deltoid force required to elevate the arm to mitigate one of the most common complications of reverse shoulder arthroplasty: acromial fractures. Also, the tuberosity augment can be used in tandem with any reverse shoulder prosthesis design to improve the deltoid moment arm and deltoid wrapping—as described in Table 2 (below), prosthesis designs with a medialized humeral component (such as the Grammont reverse shoulder) may benefit the most from the tuberosity augment as the tuberosity augment may position the deltoid sufficiently lateral to impart greater stability. This device may be implanted at the time of surgery or after the fact in revisions to impart greater stability. While the tuberosity augment of the present disclosure is intended for use in the shoulder (with or without arthroplasty), this prosthetic augment has applications in other joints as well, including the hip, knee, ankle, and spine (with or without arthroplasty) and/or any site where muscles span a joint.

In an embodiment, the addition of the augment member 12 of FIG. 8A, FIG. 8B, FIG. 8C, and FIG. 8D, increases the deltoid wrapping for the normal shoulder from 48° to 90°, from 48° to 88°, from 48° to 86°, from 48° to 84°, from 48° to 82°, from 48° to 80°, from 48° to 78°, from 48° to 76°, from 48° to 74°, from 48° to 72°, from 48° to 70°, 48° to 68°, 48° to 66°, 48° to 64°, 48° to 62°, 48° to 60°, 48° to 58°, 48° to 56°, 48° to 54°, 48° to 52° or 48° to 50°. In an embodiment, the addition of the prosthetic augment increased the deltoid wrapping for the normal shoulder from 48° to 72°, as indicated in Table 2.

In an embodiment, the addition of the augment member 12 of FIG. 8A, FIG. 8B, FIG. 8C, and FIG. 8D, increases the deltoid wrapping for the 36 Grammont shoulder (with 20° retroversion) from 8° to 45°, from 8° to 43°, from 8° to 41°, from 8° to 39°, from 8° to 37°, from 8° to 35°, from 8° to 33°, from 8° to 31°, from 8° to 29°, from 8° to 27°, from 8° to 25°, from 8° to 23°, from 8° to 21°, from 8° to 19°, from 8° to 17°, from 8° to 15°, from 8° to 13° or from 8° to 11°. In an embodiment, the addition of the prosthetic augment increased the deltoid wrapping for the 36 Grammont shoulder (with 20° retroversion) from 8° to 31°, as indicated in Table 2.

In an embodiment, the addition of the augment member 12 of FIG. 8A, FIG. 8B, FIG. 8C, and FIG. 8D increases the deltoid wrapping for the 32 Encore Reverse® shoulder from 28° to 64°, from 28° to 62°, from 28° to 60°, from 28° to 58°, from 28° to 56°, from 28° to 54°, from 28° to 52°, from 28° to 50°, from 28° to 48°, from 28° to 46°, from 28° to 44°, from 28° to 42°, from 28° to 40°, from 28° to 38° or from 28° to 36°. In an embodiment, the addition of the prosthetic augment increased the deltoid wrapping for the 32 Encore Reverse® shoulder from 28° to 56°, as indicated in Table 2.

In an embodiment, the addition of the augment member 12 of FIG. 8A, FIG. 8B, FIG. 8C, and FIG. 8D increases the deltoid wrapping for the 38 Equinoxe® shoulder from 40° to 89°, from 40° to 87°, from 40° to 85°, from 40° to 83°, from 40° to 81° from 40° to 79°, from 40° to 77°, from 40° to 75°, from 40° to 73°, from 40° to 71° or from 40° to 69°. In an embodiment, the addition of the prosthetic augment increased the deltoid wrapping for the 38 Equinoxe® shoulder from 40° to 81°, as indicated in Table 2.

Figure 10:
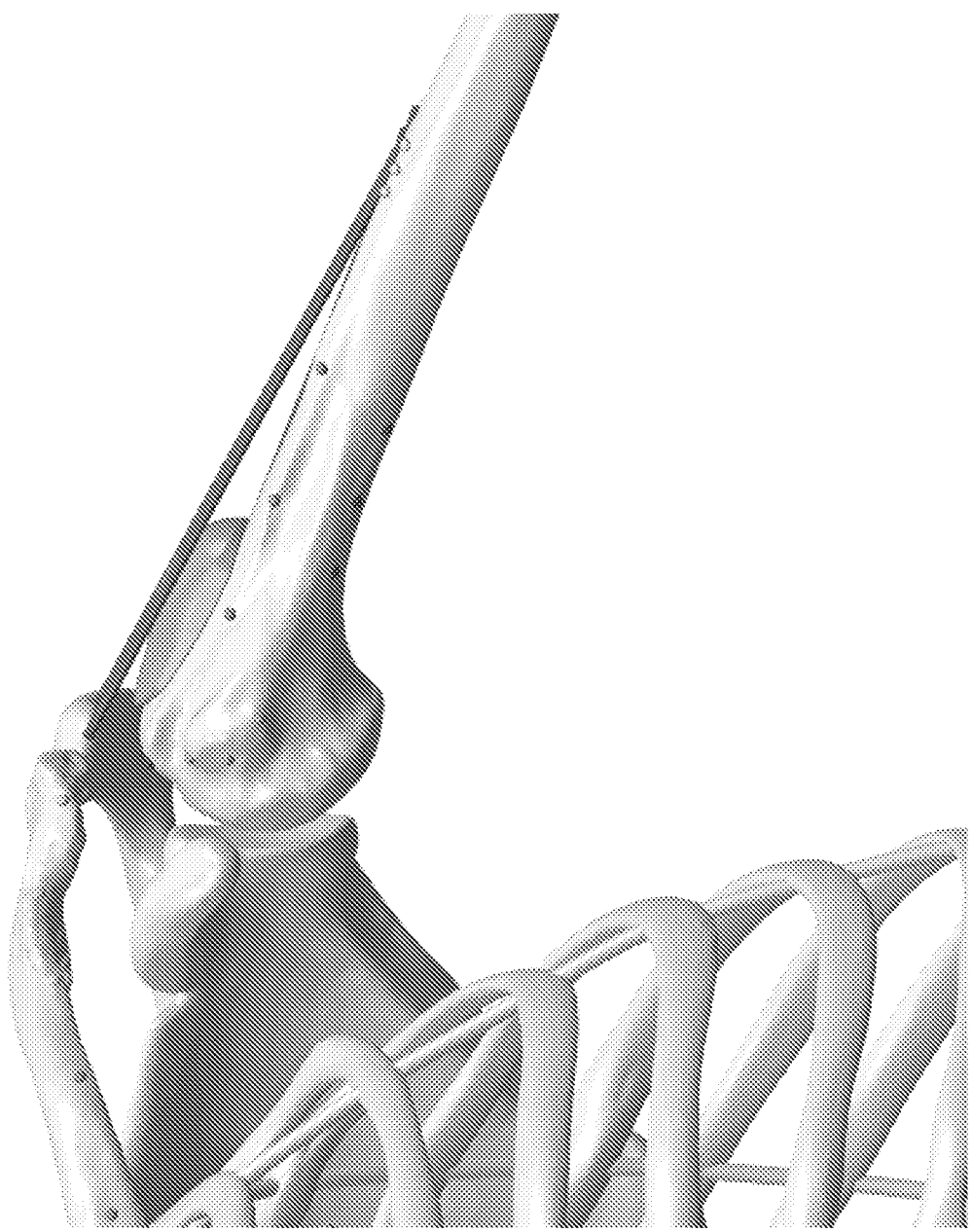
FIG. 10 is a computer model of a normal shoulder abducted to 72 degrees relative to a fixed scapula in which the middle deltoid no longer wraps the tuberosity augment of FIGS. 8A-8D and therefore no longer imparts a stabilizing compressive force to the glenoid.
Figure 11:
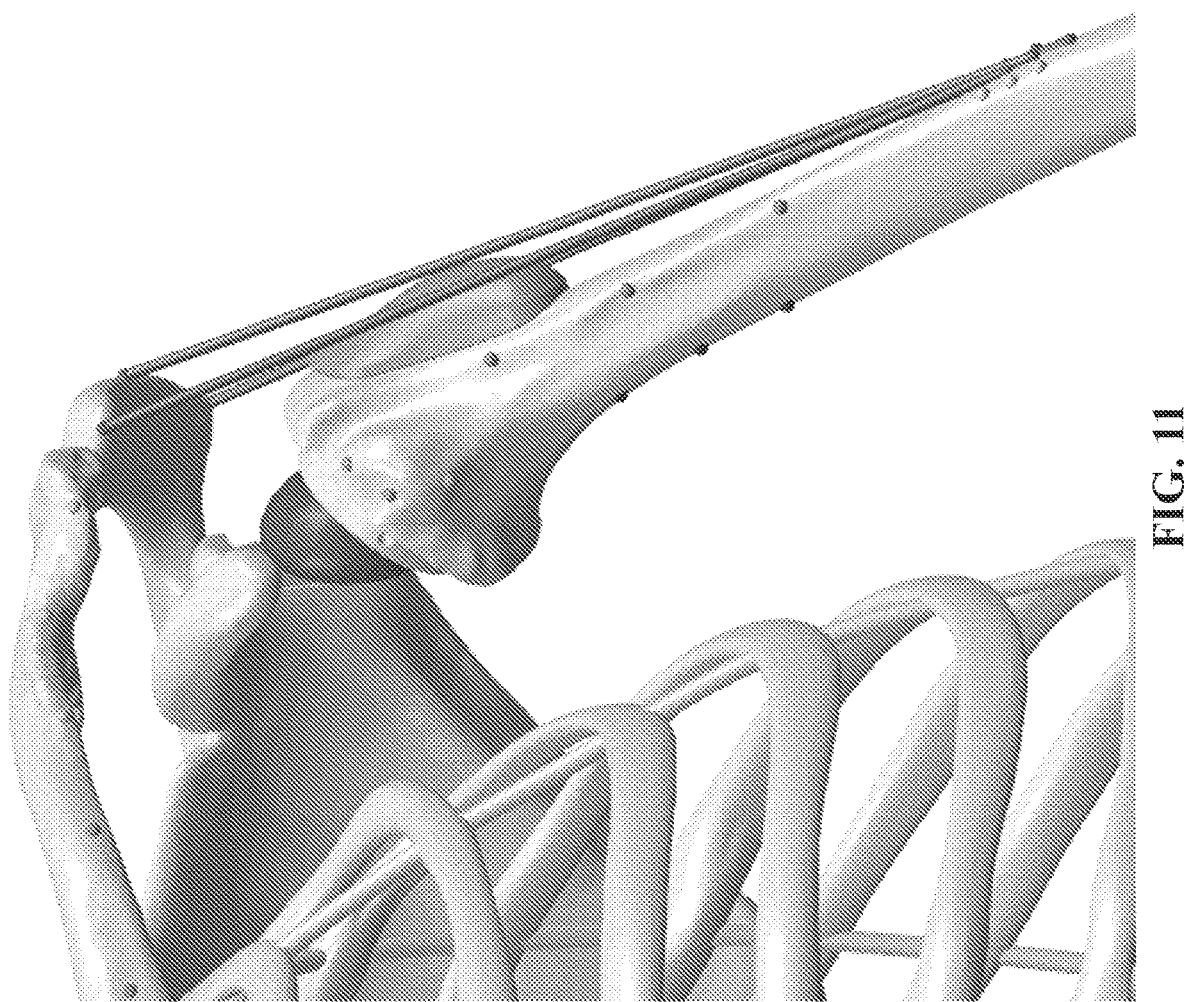
FIG. 11 is a computer model of a 36 mm Grammont reverse shoulder abducted to 31 degrees relative to a fixed scapula in which the middle deltoid no longer wraps the tuberosity augment of FIGS. 8A-8D and therefore no longer imparts a stabilizing compressive force to the glenoid.
Figure 12:
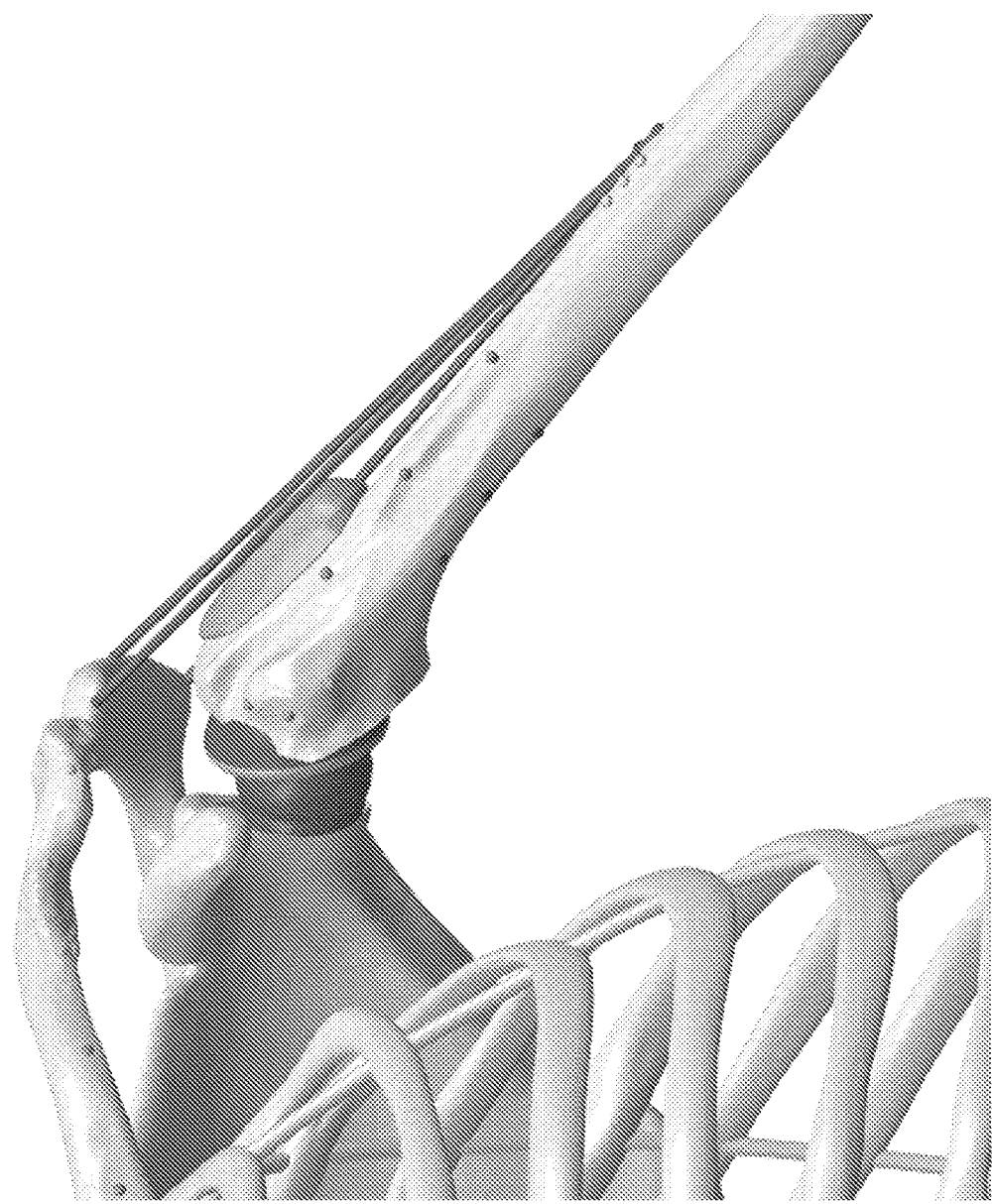
FIG. 12 is a computer model of a 32 mm Encore Reverse® shoulder abducted to 56 degrees relative to a fixed scapula in which the middle deltoid no longer wraps the tuberosity augment of FIGS. 8A-8D and therefore no longer imparts a stabilizing compressive force to the glenoid.
Figure 13:
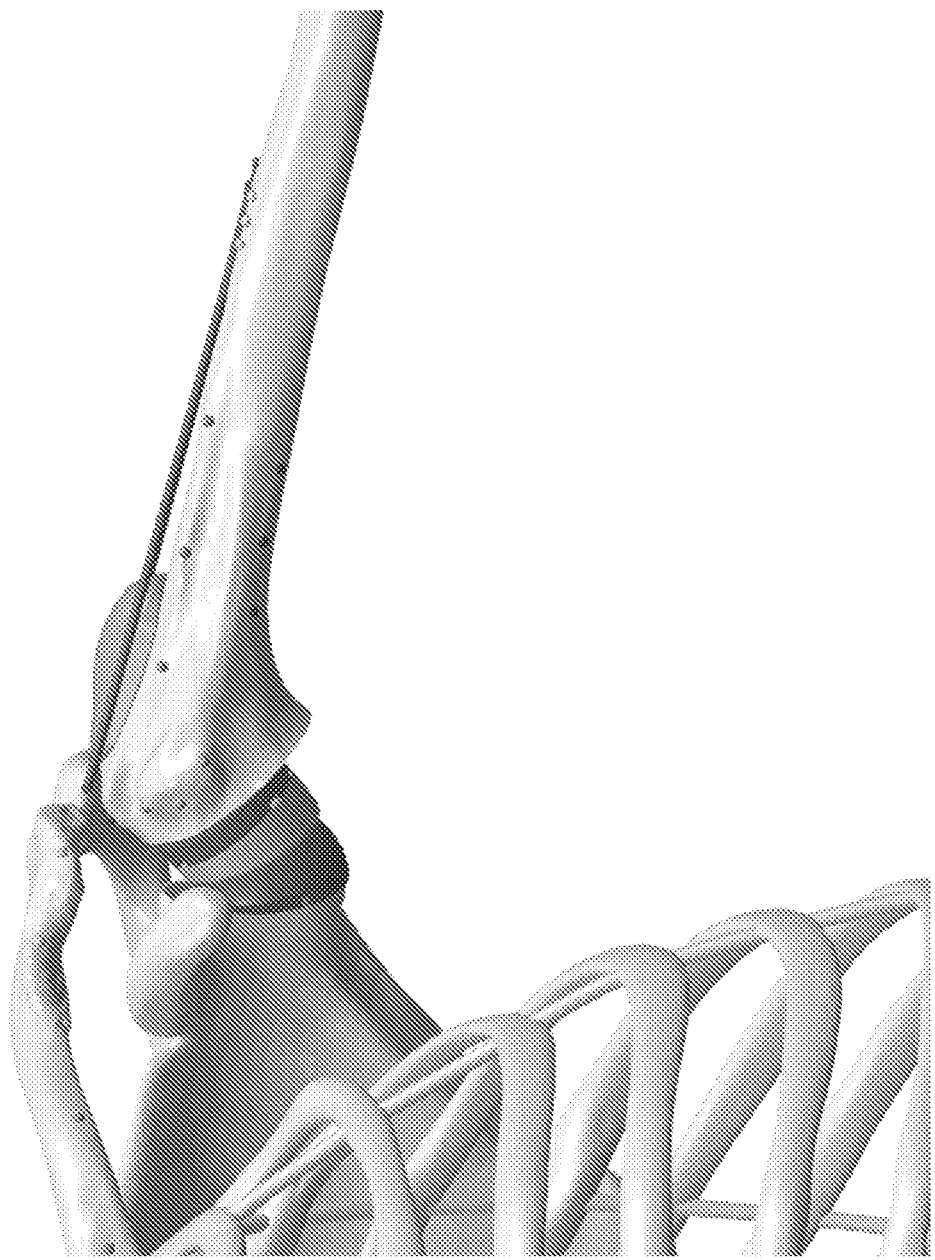
FIG. 13 is a computer model of a 38 mm Equinoxe® reverse shoulder abducted to 81 degrees relative to a fixed scapula in which the tuberosity augment of FIGS. 8A-8D on the greater tuberosity impinges with the acromion; it should be noted that at this degree of elevation the middle deltoid still wrapped the tuberosity augment.
Figure 14A:
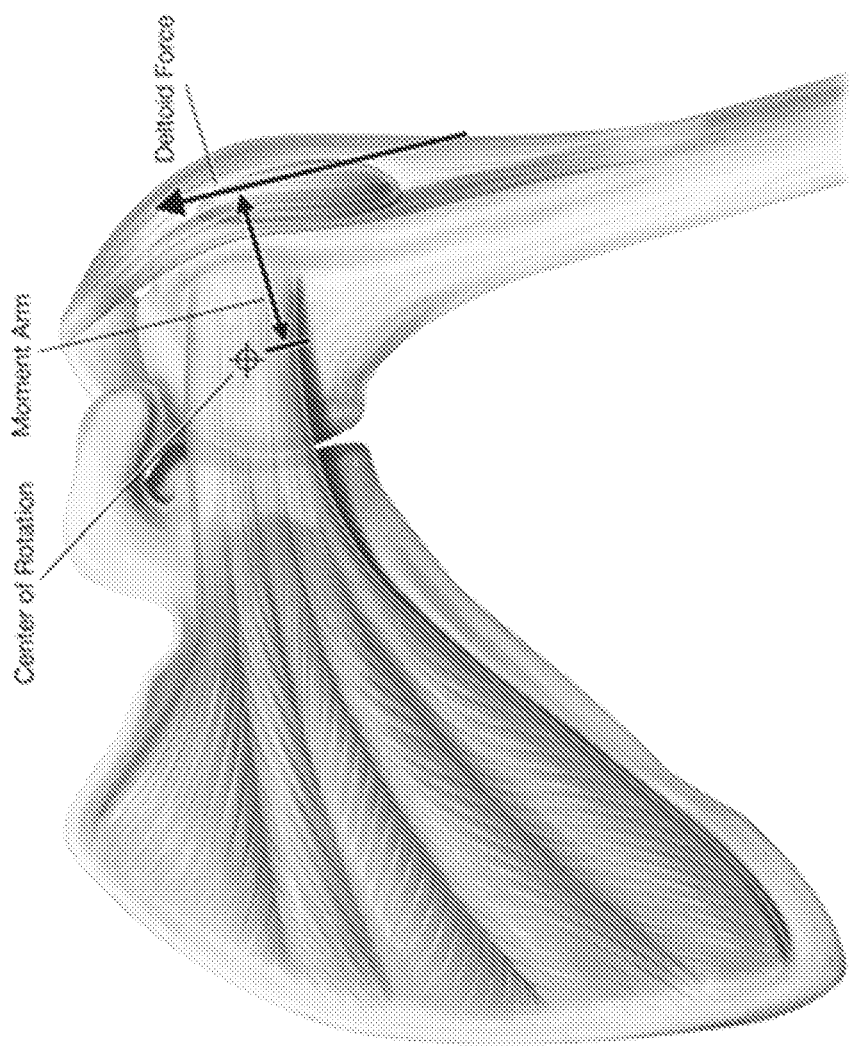
FIGS. 14A-14D are drawings comparing middle deltoid abduction moment arms between the normal shoulder (FIG. 14A) and 3 different reverse shoulder designs: Grammont (FIG. 14B), Encore Reverse® (FIG. 14C), and Equinoxe® (FIG. 14D) when each is used with the proposed prosthetic tuberosity augment of the present disclosure of FIGS. 8A-8D.
Figure 14B:
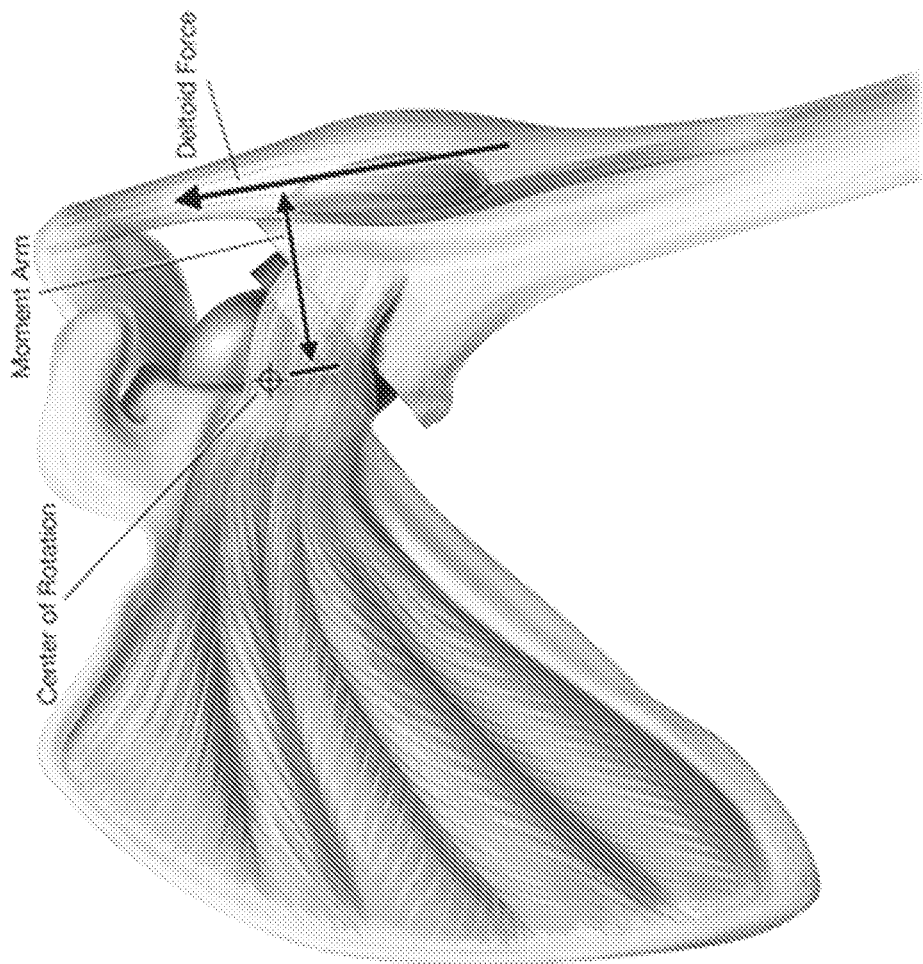
Figure 14C:
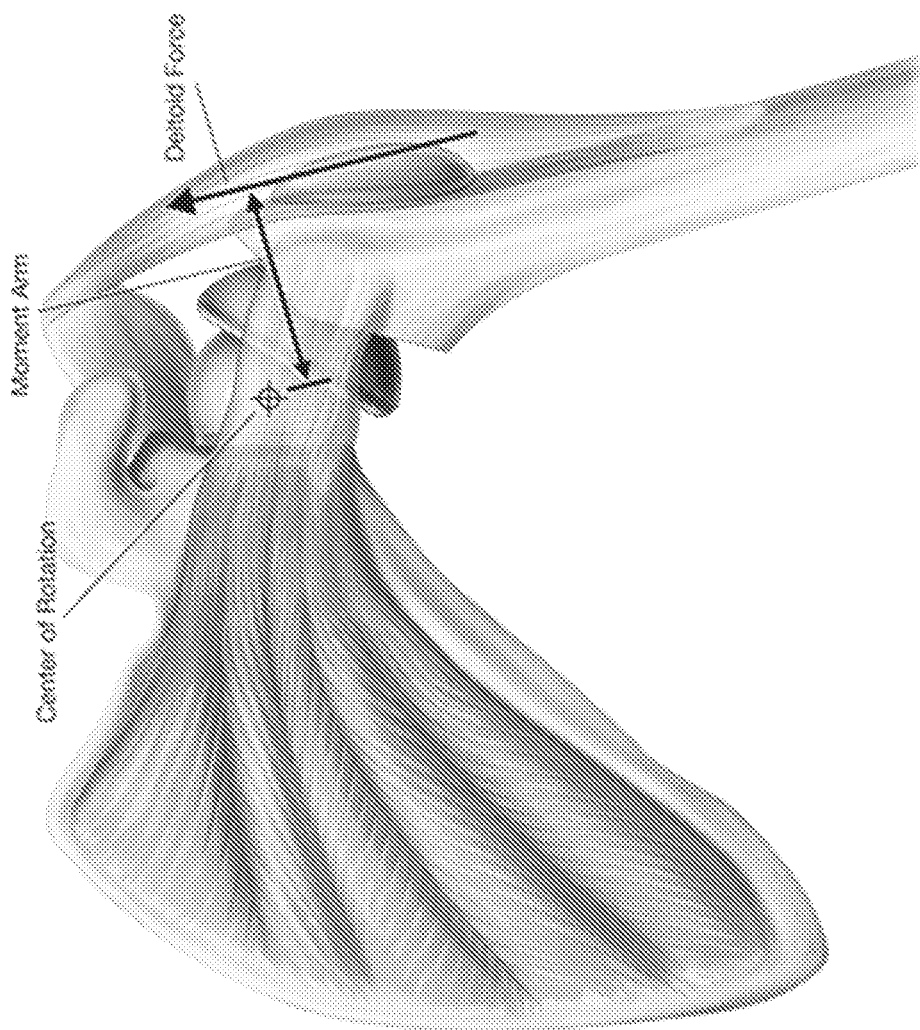
Figure 14D:
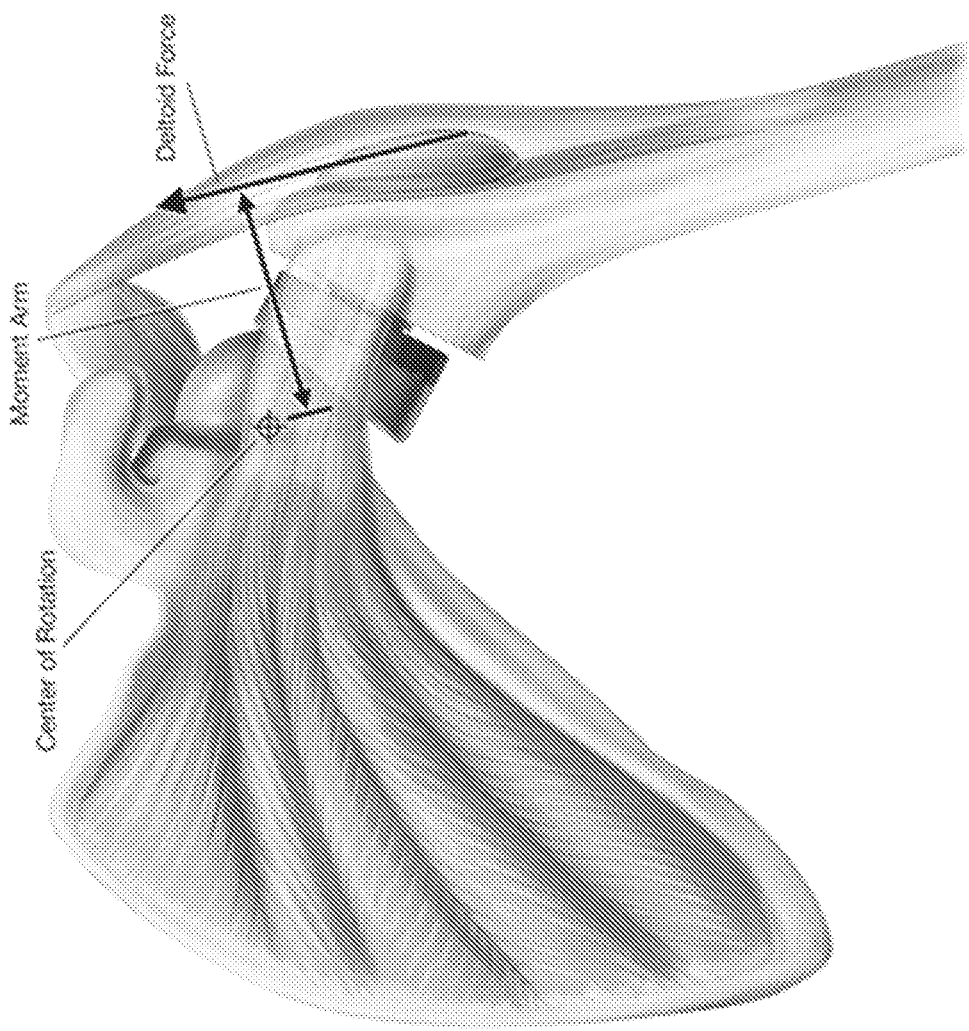
Figure 16A:
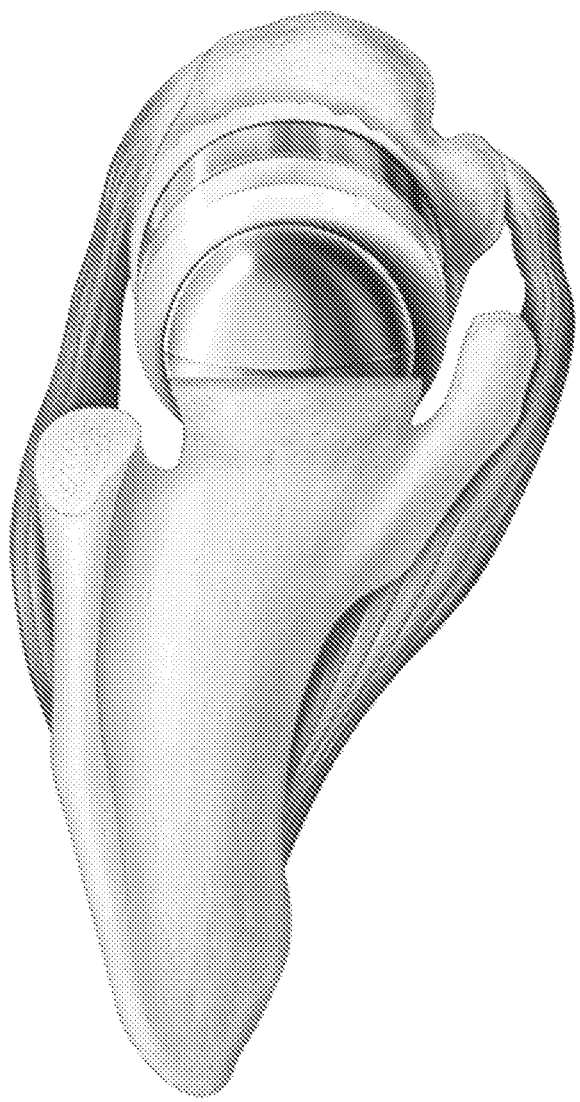
FIGS. 16A and 16B are drawings of an Equinoxe® reverse shoulder.
Figure 16B:
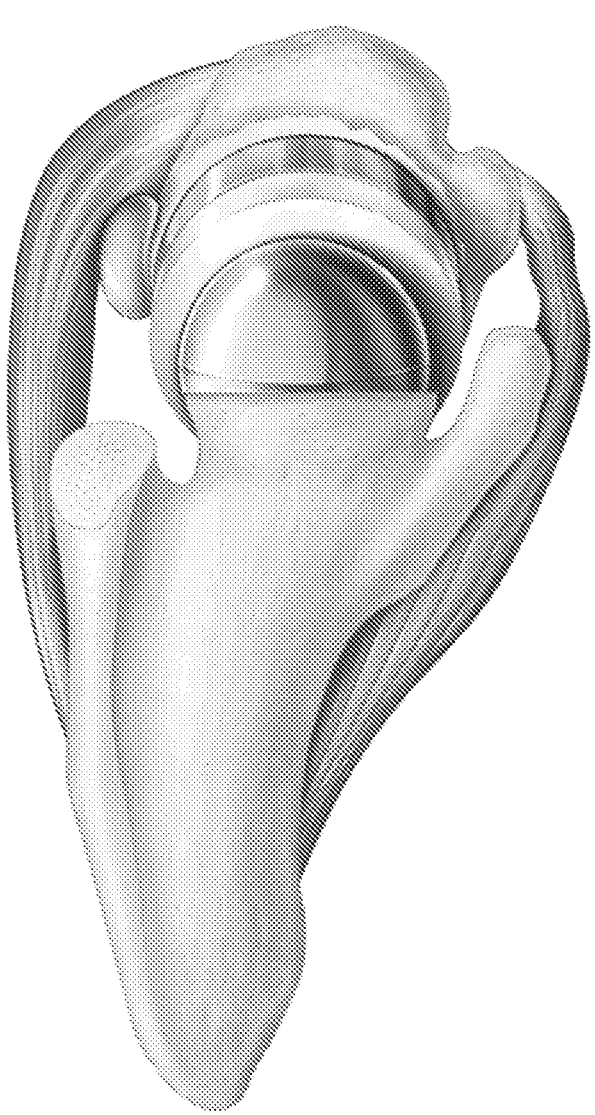

FIG. 10 illustrates the arm abduction in which the middle deltoid ceases to wrap the augment member 12 of FIG. 8A, FIG. 8B, FIG. 8C, and FIG. 8D in the normal shoulder at 72° abduction in the scapular plane (relative to a fixed scapula). FIG. 11, FIG. 12 and FIG. 13 illustrate the same deltoid wrapping phenomenon with varying reverse shoulder prosthesis designs (36 mm Grammont, 32 mm Encore Reverse®, and 38 mm Equinoxe®, respectively) when used with the augment member 12 of FIG. 8A, FIG. 8B, FIG. 8C, and FIG. 8D. Additional benefit can be expected for out of plane elevation. Table 2 lists the results of the computer model studies and shows how the deltoid wrapping can be significantly improved for each of the aforementioned prosthesis designs (36 Grammont, 20° retroversion with augment, 32 Encore Reverse®, 20° retroversion with augment, 38 Equinoxe®, 20° retroversion with augment) with the use of the augment member 12 of the present disclosure (measurements performed using a computer model which simulates muscle lines of action in the shoulder during various arm positions).

TABLE 2

| Wrapping of Middle Deltoid Around the Augment Member 12 | |
|---|---|
| | Abduction where deltoid doesn't wrap tuberosity augment |
| Normal Shoulder with Augment | 72° |
| 36 Grammont, 20° retroversion with Augment | 31° |
| 32 Encore, 20° retroversion with Augment | 56° |
| 38 Equinoxe ®, 20° retroversion with Augment | 81° (impingement; middle deltoid still wrapped at this degree of elevation) |

As depicted in FIG. 14A, FIG. 14B, FIG. 14C, and FIG. 14D the more lateral position of the middle deltoid, due to the configuration of the implanted augment member 12 of the present invention, increases the abductor moment arms for the normal shoulder and for each of the three aforementioned reverse shoulder designs (Grammont reverse shoulder, Encore reverse shoulder, vs Equinoxe® reverse shoulder). Note in FIG. 14A, FIG. 14B, FIG. 14C, and FIG. 14D the inferior and medial shift of the center of rotation.

As described in FIG. 15A, FIG. 15B, FIG. 16A and FIG. 16B, the augment member 12 can also be sufficiently designed to connect to the posterior humerus and fit underneath the posterior rotator cuff muscles (infraspinatus and teres minor) to increase their rotator moment arms (increasing the efficiency of each muscle thereby requiring less infraspinatus and/or teres minor force to externally rotate the arm). The augment member 12 can also be sufficiently designed to connect to the anterior humerus and fit underneath the internal rotation muscles (subscapularis, teres major, pectoralis major, and latissimus dorsi) to increase their rotator moment arms (increasing the efficiency of each muscle thereby requiring less subscapularis, teres major, pectoralis major, and/or latissimus dorsi force to internally rotate the arm). With reverse shoulder arthroplasty, the augment member 12 may also improve tension of these internal or external rotation muscles, which have been previously demonstrated to be lax due to the medialized center of rotation caused by the inversion of the concavities (e.g. laxity inherent to reverse shoulder arthroplasty).

FIG. 17A, FIG. 17B, FIG. 17C, and FIG. 17D show four views of a second embodiment of a prosthetic augment 20 of the present disclosure comprising an augment member 22. The prosthetic augment 20 may further comprise locking bone screws. In an embodiment, the augment member 22 is a cam/tear-drop shaped, smooth, spherically/splined-curved augment. The augment member 22 is configured to extend a length of a patient's bone, and has a first face 24 adapted for receiving contact with the patient's bone and a second face 26 adapted for receiving contact with the underbelly of a muscle of the patient. The augment member 22 has a proximal end PE toward a head of the patient and a distal end DE toward a hip of the patient. The second face 26 of the augment member 22 includes a bulbous surface 25 resulting in a thickness of the augment member 22 being non-uniform from the distal end DE to the proximal end PE. The bulbous surface 25 is sufficiently elongated to accommodate the anatomic variance of the bone. The second face 26 has a variable radius meaning that at least two different constant radii exist on the second face 26.

Figures 17A, 17B, 17C, 17D:
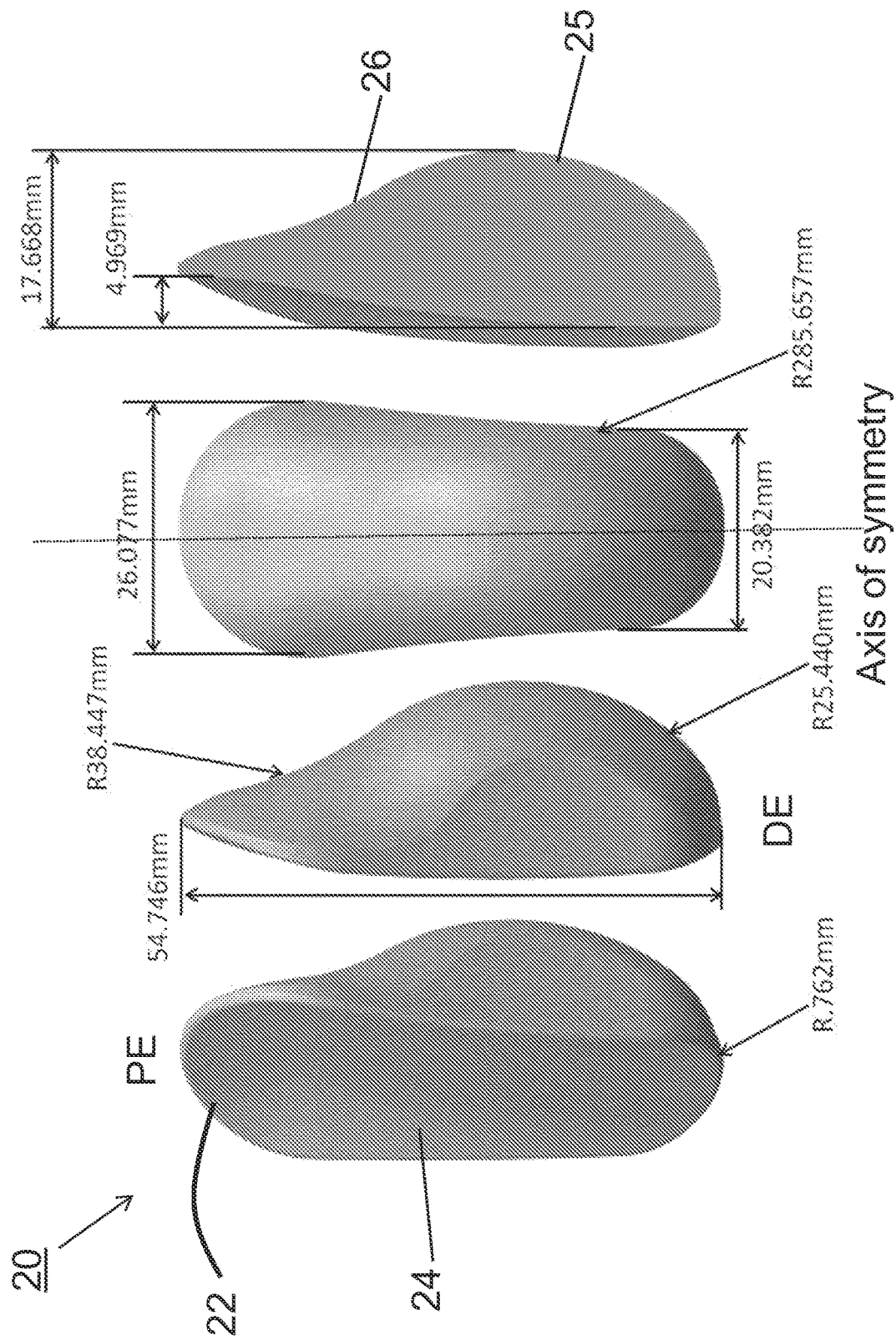
FIGS. 17A-17D show four views of a second embodiment of a cam/tear-drop shaped, smooth, spherically/splined-curved prosthetic expanded tuberosity augment of the present disclosure that is +5 mm thicker than the first embodiment depicted in FIGS. 8A-8D.
Figure 19:
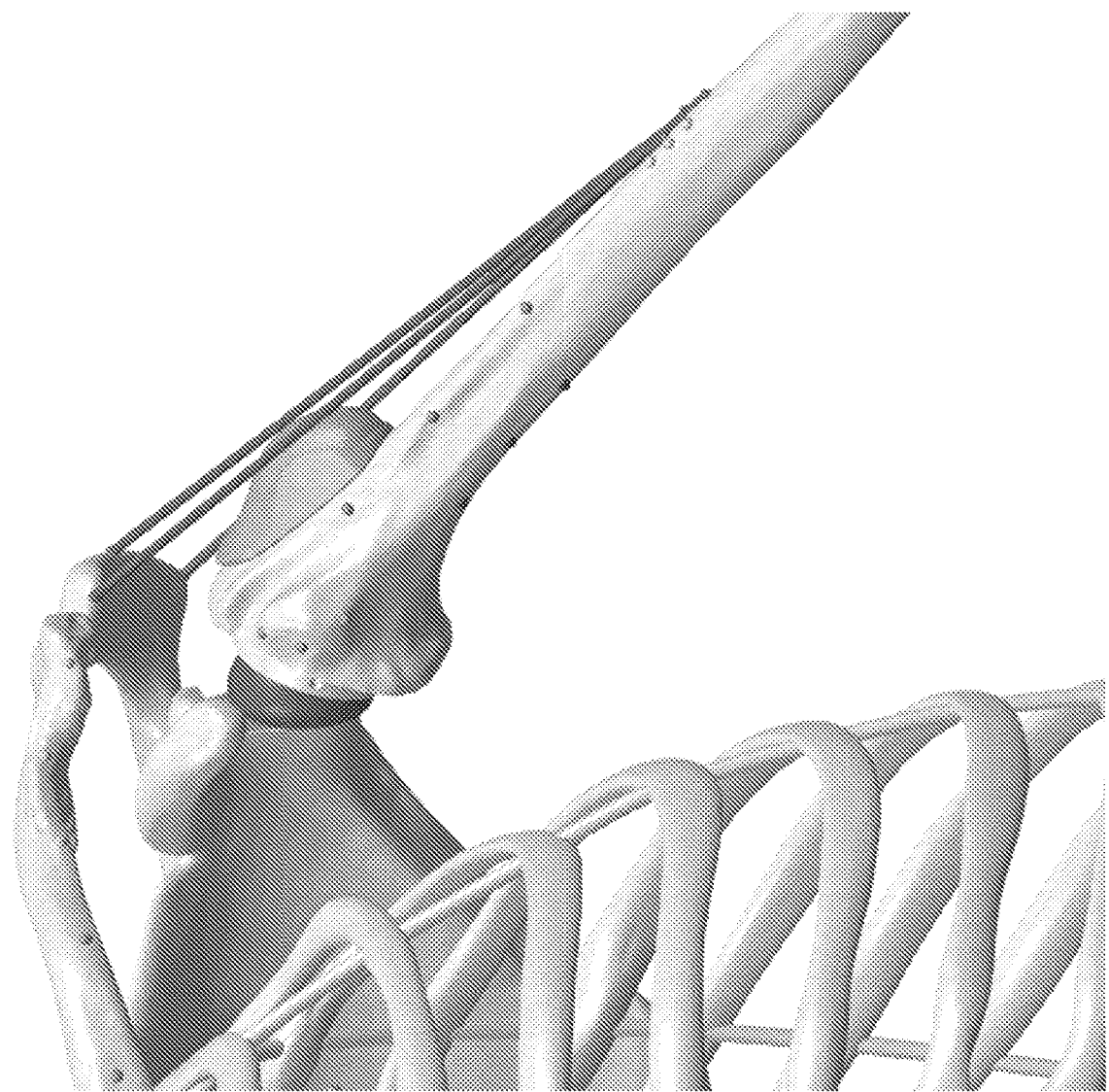
FIG. 19 is a computer model of a 36 mm Grammont reverse shoulder abducted to 52 degrees relative to a fixed scapula in which the middle deltoid no longer wraps the +5 mm expanded tuberosity augment of FIGS. 17A-17D and therefore no longer imparts a stabilizing compressive force to the glenoid.
Figure 20:
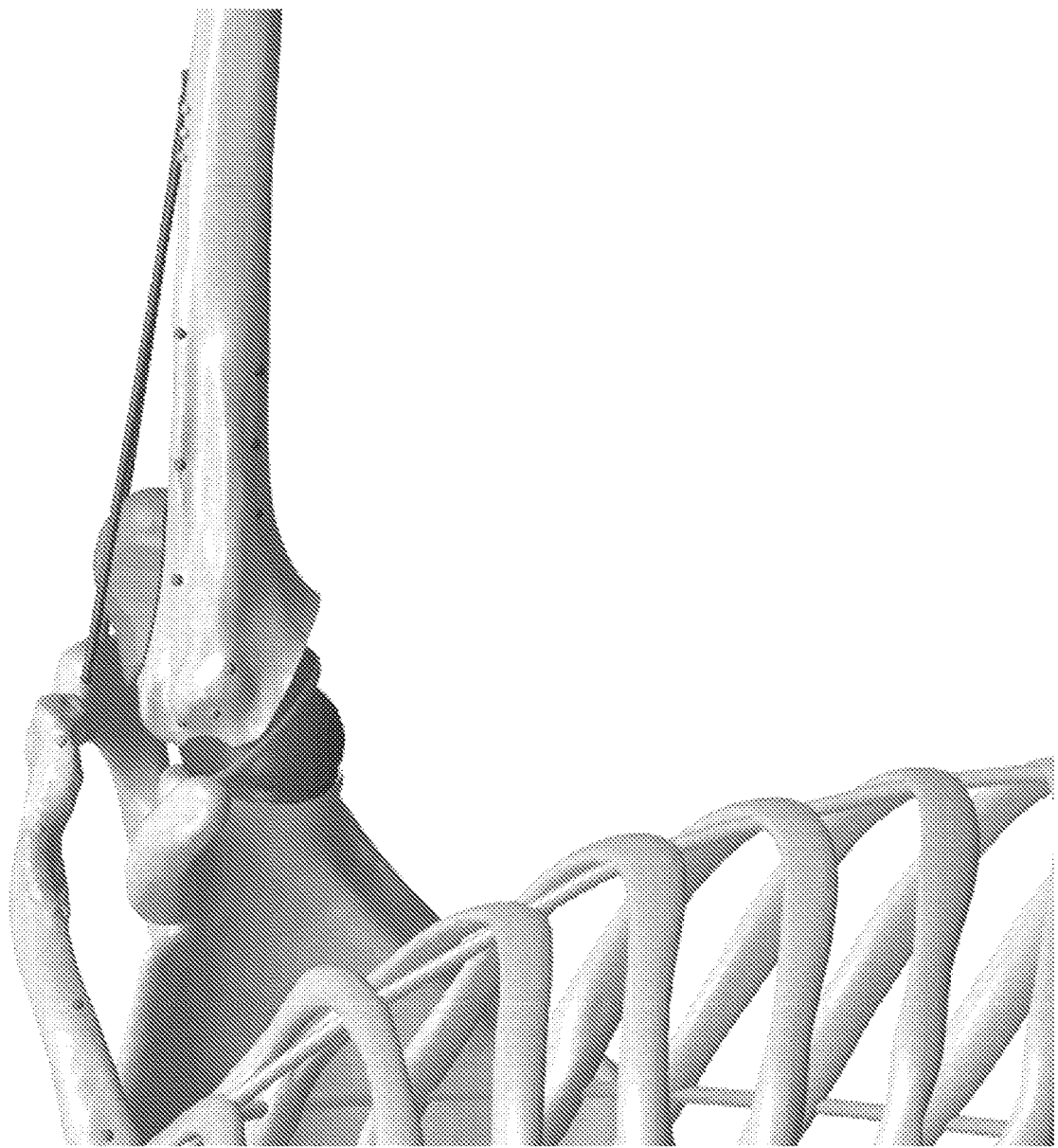
FIG. 20 is a computer model of a 32 mm Encore Reverse® shoulder abducted to 90 degrees relative to a fixed scapula in which +5 mm expanded tuberosity augment of FIGS. 17A-17D on the greater tuberosity impinges with the acromion; it should be noted that at this degree of elevation the middle deltoid still wrapped the augment.
Figure 21:
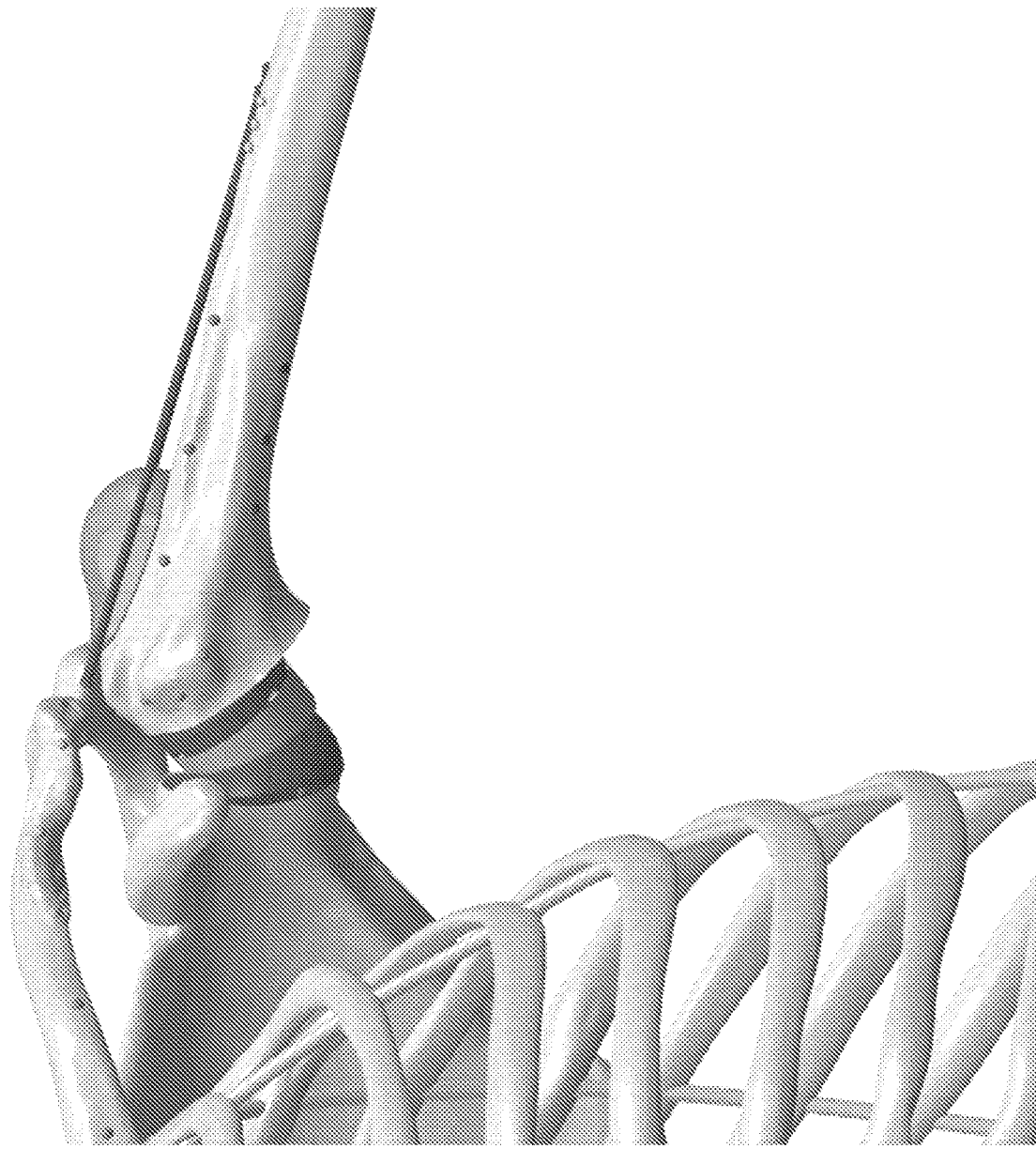
FIG. 21 is a computer model of a 38 mm Equinoxe® reverse shoulder abducted to 81 degrees relative to a fixed scapula in which the +5 mm expanded augment of FIGS. 17A-17D on the greater tuberosity impinges with the acromion; it should be noted that at this degree of elevation the middle deltoid still wrapped the augment.

FIG. 17D shows the thickness between first face 24 and second face 26 is non-uniform. A first thickness is defined between the first face 24 and the second face 26 at a first position on the augment member 22. A second thickness is defined between the first face 24 and the bulbous surface 25 of the second face 26. The first thickness and the second thickness are not equivalent so as to result in the augment member 22 having a non-uniform thickness. In this embodiment, the second thickness is +5 mm thicker than the second thickness in the first embodiment depicted in FIG. 8A, FIG. 8B, FIG. 8C, and FIG. 8D. The augment member 22 comprises variable thicknesses at multiple positions. In an embodiment, the first thickness is less than about 5 mm. In an embodiment, the first thickness ranges from about 1 mm to less than about 5 mm. In an embodiment, the first thickness ranges from about 1 mm to about 4 mm. In an embodiment, the first thickness ranges from about 2 mm to about 3 mm. In an embodiment, the second thickness ranges from above 6 mm to about 55 mm. In an embodiment, the second thickness ranges from above 7 mm to about 53 mm. In an embodiment, the second thickness ranges from above 8 mm to about 51 mm. In an embodiment, the second thickness ranges from above 69 mm to about 49 mm. In an embodiment, the second thickness ranges from about 10 mm to about 46 mm. In an embodiment, the second thickness ranges from about 14 mm to about 42 mm. In an embodiment, the second thickness ranges from about 18 mm to about 38 mm. In an embodiment, the second thickness ranges from about 22 mm to about 34 mm. In an embodiment, the second thickness ranges from about 26 mm to about 30 mm. In an embodiment, the second thickness ranges from about 11 mm to about 19 mm. In an embodiment, the second thickness ranges from about 6 mm to about 40 mm. In an embodiment, the second thickness ranges from about 6 mm to about 30 mm. In an embodiment, the second thickness ranges from about 6 mm to about 20 mm. In an embodiment, the second thickness ranges between about 6 mm to about 10 mm. In an embodiment, the second thickness ranges between about 6.5 mm to about 9.5 mm. In an embodiment, the second thickness ranges between about 7 mm to about 9 mm. In an embodiment, the second thickness ranges between about 7.5 mm to about 8.5 mm.

First face 24 can be contoured (as illustrated) or can be flat. The bulbous surface 25 is sufficiently designed to result in an increase in the wrapping point of a deltoid muscle around the greater tuberosity and also an increase in the abductor moment arm of the deltoid muscle. In an embodiment, the bulbous surface 25 is shaped round to prevent abrasion of the muscle as the augment member 22 fits between the underbelly of the muscle and the lateral humeral bone. The curvature and location of the augment member 22 profile is sufficiently designed so that the center of rotation of the bulbous surface 25 approaches that of the native joint so that the compression of the deltoid muscle will result in a stabilizing force. In an embodiment, the size of the augment member 22 and the amount of lateralization is limited by the impingement that could result with the acromion at high arm elevation. In an embodiment, the superior portion of the augment member 22 is intended to be thin with a thickness so that the augment member 22 can potentially slide under the acromion if placed high or be low profile so that the augment member 22 doesn't impinge.

In an embodiment, the prosthetic augment member 22 has "bilateral" (two-sided) symmetry, because the left and right halves of the augment member 22 mirror each other, allowing the prosthetic augment to be used in left and right bones. The dotted line running down the middle of the augment member 22 is called "the axis of symmetry" In an embodiment, the prosthetic augment can be sufficiently designed to be asymmetric and be provided in lefts and rights in order to better fit the individual patient's anatomy. In an embodiment, an edge of the distal end DE of the augment member 22 is curved. In an embodiment, an edge of the proximal end PE of the augment member 22 is curved. In an embodiment, the augment member 22 ranges from about 20.00 mm to about 50.00 mm in length. In an embodiment, the augment member 22 ranges from about 21.00 mm to about 49.00 mm in length. In an embodiment, the augment member 22 ranges from about 22.00 mm to about 48.00 mm in length. In an embodiment, the augment member 22 ranges from about 23.00 mm to about 47.00 mm in length. In an embodiment, the augment member 22 ranges from about 24.00 mm to about 46.00 mm in length. In an embodiment, the augment member 22 ranges from about 25.00 mm to about 45.00 mm in length. In an embodiment, the augment member 22 ranges from about 26.00 mm to about 44.00 mm in length. In an embodiment, the augment member 22 ranges from about 27.00 mm to about 43.00 mm in length. In an embodiment, the augment member 22 ranges from about 28.00 mm to about 42.00 mm in length. In an embodiment, the augment member 22 ranges from about 29.00 mm to about 41.00 mm in length. In an embodiment, the augment member 22 ranges from about 31.00 mm to about 39.00 mm in length. In an embodiment, the augment member 22 ranges from about 32.00 mm to about 38.00 mm in length. In an embodiment, the augment member 22 ranges from about 33.00 mm to about 37.00 mm in length. In an embodiment, the augment member 22 ranges from about 34.00 mm to about 36.00 mm in length. In an embodiment, the augment member 22 ranges from about 50.00 mm to about 60.00 mm in length. In an embodiment, the augment member 22 ranges from about 51.00 mm to about 59.00 mm in length. In an embodiment, the augment member 22 ranges from about 52.00 mm to about 58.00 mm in length. In an embodiment, the augment member 22 ranges from about 53.00 mm to about 57.00 mm in length. In an embodiment, the augment member 22 ranges from about 54.00 mm to about 56.00 mm in length. In an embodiment, the augment member 22 ranges from about 54.50 mm to about 55.50 mm in length. In an embodiment, the augment member 22 is about 55.00 mm in length.

FIG. 18 is a computer model of a normal shoulder abducted to 99 degrees relative to a fixed scapula in which the middle deltoid no longer wraps the +5 mm expanded tuberosity augment of FIG. 17A, FIG. 17B, FIG. 17C, and FIG. 17D and therefore no longer imparts a stabilizing compressive force to the glenoid.

The augment member 22 of FIG. 17A, FIG. 17B, FIG. 17C, and FIG. 17D can lateralize the deltoid further to improve the wrapping angle and moment arm for the normal shoulder and for each of the aforementioned prosthesis designs (Grammont reverse shoulder, Encore reverse shoulder, Equinoxe® reverse shoulder) as described in FIG. 18, FIG. 19, FIG. 20 and FIG. 21 and Table 3.

In an embodiment, the addition of the augment member 22 of FIG. 17A, FIG. 17B, FIG. 17C, and FIG. 17D increases the deltoid wrapping for the normal shoulder from 48° to 113°, from 48° to 111°, from 48° to 109°, from 48° to 107°, from 48° to 105°, from 48° to 103°, from 48° to 101°, from 48° to 99°, from 48° to 97°, from 48° to 95°, from 48° to 93°, 48° to 91°, 48° to 89°, 48° to 87°, 48° to 85°, 48° to 83°, 48° to 81°, 48° to 79°, 48° to 77°, 48° to 75° or 48° to 73°. In an embodiment, the addition of the prosthetic augment increased the deltoid wrapping for the normal shoulder from 48° to 99°, as indicated in Table 3.

In an embodiment, the addition of the augment member 22 of FIG. 17A, FIG. 17B, FIG. 17C, and FIG. 17D increases the deltoid wrapping for the 36 Grammont shoulder (with 20° retroversion) from 8° to 66°, from 8° to 64°, from 8° to 62°, from 8° to 60°, from 8° to 58°, from 8° to 56°, from 8° to 54°, from 8° to 52°, from 8° to 50°, from 8° to 48°, from 8° to 46°, from 8° to 44°, from 8° to 42°, from 8° to 40°, from 8° to 38°, from 8° to 36°, from 8° to 34° or from 8° to 32°. In an embodiment, the addition of the prosthetic augment increased the deltoid wrapping for the 36 Grammont shoulder (with 20° retroversion) from 8° to 52°, as indicated in Table 3.

In an embodiment, the addition of the augment member 22 of FIG. 17A, FIG. 17B, FIG. 17C, and FIG. 17D increases the deltoid wrapping for the 32 Encore Reverse® shoulder from 28° to 98°, from 28° to 96°, from 28° to 94°, from 28° to 92°, from 28° to 90°, from 28° to 88°, from 28° to 86°, from 28° to 84°, from 28° to 82°, from 28° to 80°, from 28° to 78°, from 28° to 76°, from 28° to 74°, from 28° to 72° or from 28° to 70°. In an embodiment, the addition of the prosthetic augment increased the deltoid wrapping for the 32 Encore Reverse® shoulder from 28° to 90°, as indicated in Table 3.

In an embodiment, the addition of the augment member 22 of FIG. 17A, FIG. 17B, FIG. 17C, and FIG. 17D increases the deltoid wrapping for the 38 Equinoxe® shoulder from 40° to 89°, from 40° to 87°, from 40° to 85°, from 40° to 83°, from 40° to 81° from 40° to 79°, from 40° to 77°, from 40° to 75°, from 40° to 73°, from 40° to 71° or from 40° to 69°. In an embodiment, the addition of the augment member 22 increased the deltoid wrapping for the 38 Equinoxe® shoulder from 40° to 81°, as indicated in Table 3.

TABLE 3

Wrapping of Middle Deltoid Around the +5 mm Expanded Augment Member 22

| | Abduction where deltoid doesn't wrap tuberosity augment |
|---|---|
| Normal Shoulder with Augment | 99° |
| 36 Grammont, 20° retroversion with +5 mm Augment | 52° |
| 32 Encore reverse ®, 20° retroversion with +5 mm Augment | 90° (impingement; middle deltoid still wrapped at this degree of elevation) |
| 38 Equinoxe ®, 20° retroversion with +5 mm Augment | 81° (impingement; middle deltoid still wrapped at this degree of elevation) |

FIG. 22A, FIG. 22B, FIG. 22C, and FIG. 22D show four views of a third embodiment of a prosthetic augment 30 of the present disclosure comprising an augment member 32. The prosthetic augment 30 may further comprise locking bone screws. In an embodiment, the augment member 32 is a cam/tear-drop shaped, smooth, spherically/splined-curved augment. The augment member 32 is configured to extend a length of a patient's bone, and has a first face 34 adapted for receiving contact with the patient's bone and a second face 36 adapted for receiving contact with the underbelly of a muscle of the patient. The augment member 32 has a proximal end PE toward a head of the patient and a distal end DE toward a hip of the patient. The second face 36 of the augment member 32 includes a bulbous surface 35 resulting in a thickness of the augment member 22 being non-uniform from the distal end DE to the proximal end PE. In this embodiment, the bulbous surface 35 is superiorly shifted as compared with the first embodiment depicted in FIGS. 8A-8D and the second embodiment depicted in FIG. 17A, FIG. 17B, FIG. 17C, and FIG. 17D. Superior shift may improve the anatomic contour of the patient's shoulder. The augment of FIG. 22A, FIG. 22B, FIG. 22C, and FIG. 22D may be useful for improving cosmetic concerns with arthroplasty; particularly reverse shoulder arthroplasty in which the shoulder is elongated and may not have an anatomic contour—in such a situation these augments may restore the anatomic aesthetic. The bulbous surface 35 is sufficiently elongated to accommodate the anatomic variance of the bone. The second face 36 has a variable radius meaning that at least two different constant radii exist on the second face 36.

Figures 22A, 22B, 22C, 22D:
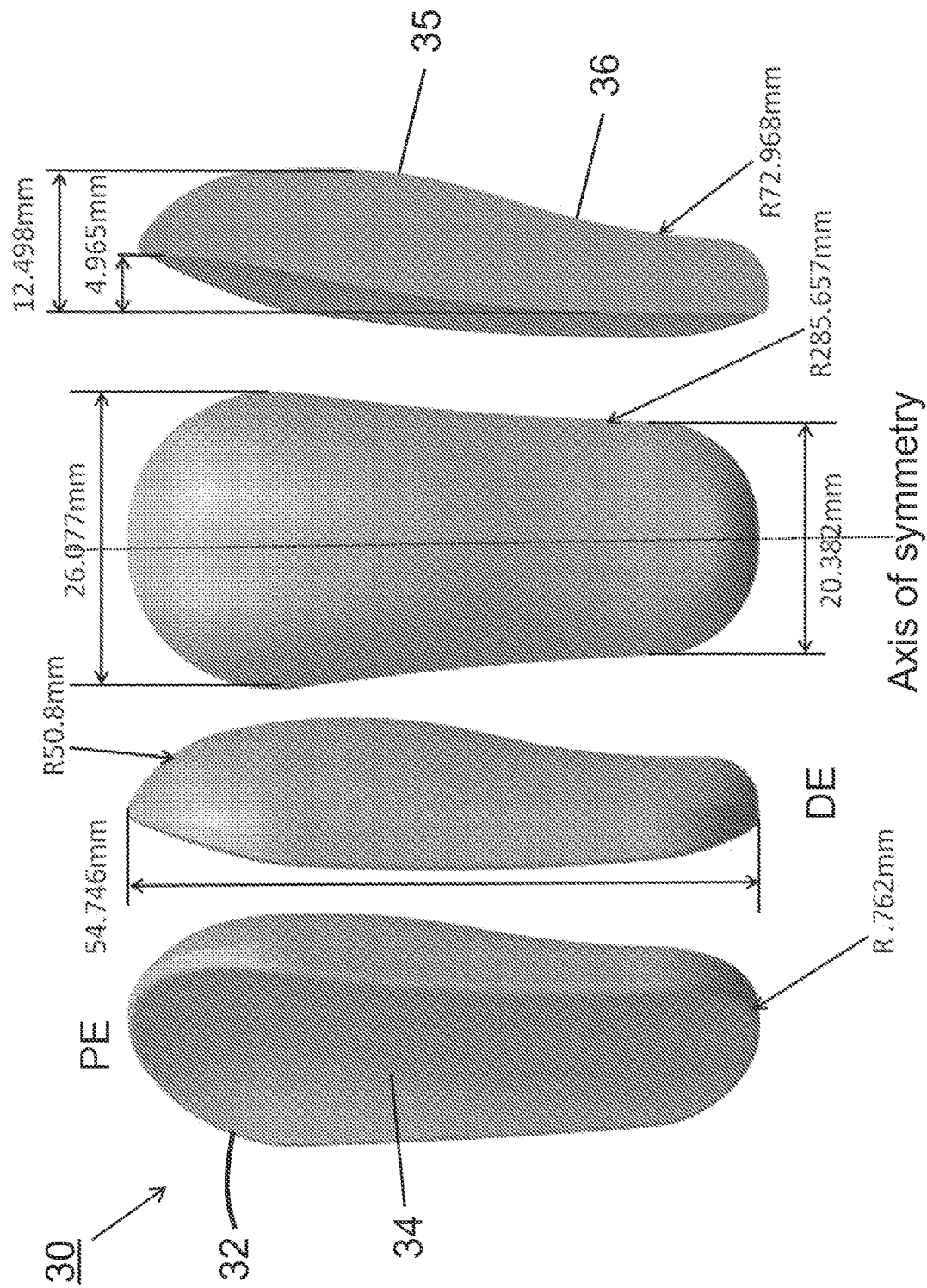
FIGS. 22A-22D show four views of a third embodiment of a cam/tear-drop shaped, smooth, spherically/splined-curved prosthetic tuberosity augment of the present disclosure where the "bump" is superiorly shifted as compared with the first embodiment depicted in FIGS. 8A-8D and the second embodiment depicted in FIGS. 17A-17D. Superior shift may improve the anatomic contour of the patient's shoulder, particularly when used with reverse shoulder arthroplasty.

FIG. 22D shows the thickness between first face 34 and second face 36 is non-uniform. A first thickness is defined between the first face 34 and the second face 36 at a first position on the augment member 32. A second thickness is defined between the first face 34 and the bulbous surface 35 of the second face 36. The first thickness and the second thickness are not equivalent so as to result in the augment member 32 having a non-uniform thickness. The augment member 32 comprises variable thicknesses at multiple positions. In an embodiment, the first thickness is less than about 5 mm. In an embodiment, the first thickness ranges from about 1 mm to less than about 5 mm. In an embodiment, the first thickness ranges from about 1 mm to about 4 mm. In an embodiment, the first thickness ranges from about 2 mm to about 3 mm. In an embodiment, the second thickness ranges from above 6 mm to about 50 mm. In an embodiment, the second thickness ranges from about 10 mm to about 46 mm. In an embodiment, the second thickness ranges from about 14 mm to about 42 mm. In an embodiment, the second thickness ranges from about 18 mm to about 38 mm. In an embodiment, the second thickness ranges from about 22 mm to about 34 mm. In an embodiment, the second thickness ranges from about 26 mm to about 30 mm. In an embodiment, the second thickness ranges from about 11 mm to about 19 mm. In an embodiment, the second thickness ranges from about 6 mm to about 40 mm. In an embodiment, the second thickness ranges from about 6 mm to about 30 mm. In an embodiment, the second thickness ranges from about 6 mm to about 20 mm. In an embodiment, the second thickness ranges between about 6 mm to about 10 mm. In an embodiment, the second thickness ranges between about 6.5 mm to about 9.5 mm. In an embodiment, the second thickness ranges between about 7 mm to about 9 mm. In an embodiment, the second thickness ranges between about 7.5 mm to about 8.5 mm.

First face 34 can be contoured (as illustrated) or can be flat. The bulbous surface 35 is sufficiently designed to result in an increase in the wrapping point of a deltoid muscle around the greater tuberosity and also an increase in the abductor moment arm of the deltoid muscle. In an embodiment, the bulbous surface 35 is shaped round to prevent abrasion of the muscle as the augment member 32 fits between the underbelly of the muscle and the lateral humeral bone. The curvature and location of the augment member 32 profile is sufficiently designed so that the center of rotation of the bulbous surface 35 approaches that of the native joint so that the compression of the deltoid muscle will result in a stabilizing force. In an embodiment, the size of the augment member 32 and the amount of lateralization is limited by the impingement that could result with the acromion at high arm elevation. In an embodiment, the superior portion of the augment member 32 is intended to be thin with a thickness so that the augment member 32 can potentially slide under the acromion if placed high or be low profile so that the augment member 32 doesn't impinge.

In an embodiment, the augment member 32 has "bilateral" (two-sided) symmetry, because the left and right halves of the augment member 32 mirror each other, allowing the prosthetic augment to be used in left and right bones. The dotted line running down the middle of the augment member 32 is called "the axis of symmetry" In an embodiment, the prosthetic augment can be sufficiently designed to be asymmetric and be provided in lefts and rights in order to better fit the individual patient's anatomy. In an embodiment, an edge of the distal end DE of the augment member 32 is curved. In an embodiment, an edge of the proximal end PE of the augment member 32 is curved. In an embodiment, the augment member 32 ranges from about 20.00 mm to about 50.00 mm in length. In an embodiment, the augment member 32 ranges from about 21.00 mm to about 49.00 mm in length. In an embodiment, the augment member 32 ranges from about 22.00 mm to about 48.00 mm in length. In an embodiment, the augment member 32 ranges from about 23.00 mm to about 47.00 mm in length. In an embodiment, the augment member 32 ranges from about 24.00 mm to about 46.00 mm in length. In an embodiment, the augment member 32 ranges from about 25.00 mm to about 45.00 mm in length. In an embodiment, the augment member 32 ranges from about 26.00 mm to about 44.00 mm in length. In an embodiment, the augment member 32 ranges from about 27.00 mm to about 43.00 mm in length. In an embodiment, the augment member 32 ranges from about 28.00 mm to about 42.00 mm in length. In an embodiment, the augment member 32 ranges from about 29.00 mm to about 41.00 mm in length. In an embodiment, the augment member 32 ranges from about 31.00 mm to about 39.00 mm in length. In an embodiment, the augment member 32 ranges from about 32.00 mm to about 38.00 mm in length. In an embodiment, the augment member 32 ranges from about 33.00 mm to about 37.00 mm in length. In an embodiment, the augment member 32 ranges from about 34.00 mm to about 36.00 mm in length. In an embodiment, the augment member 32 ranges from about 50.00 mm to about 60.00 mm in length. In an embodiment, the augment member 32 ranges from about 51.00 mm to about 59.00 mm in length. In an embodiment, the augment member 32 ranges from about 52.00 mm to about 58.00 mm in length. In an embodiment, the augment member 32 ranges from about 53.00 mm to about 57.00 mm in length. In an embodiment, the augment member 32 ranges from about 54.00 mm to about 56.00 mm in length. In an embodiment, the augment member 32 ranges from about 54.50 mm to about 55.50 mm in length. In an embodiment, the augment member 32 is about 55.00 mm in length.

Figures 23A, 23B, 23C:
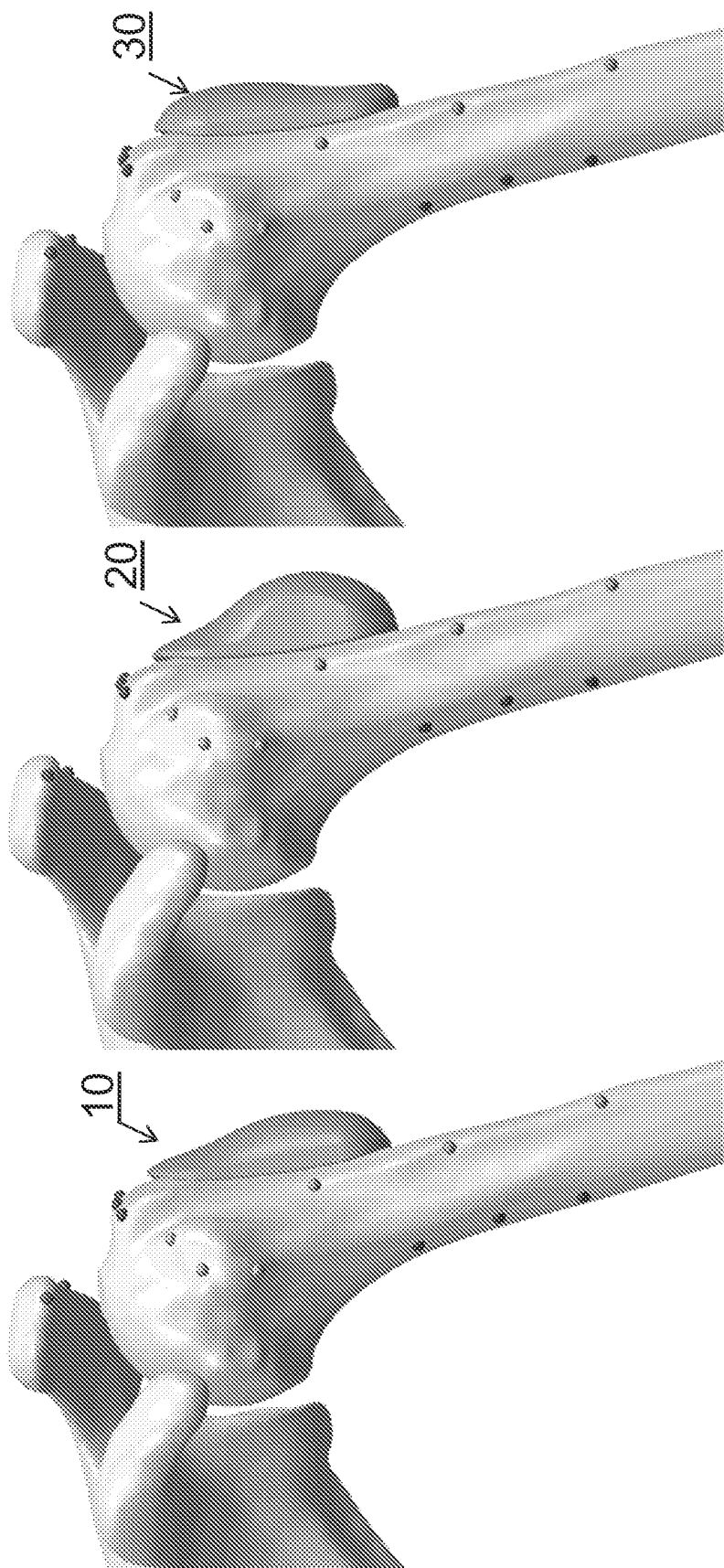
FIGS. 23A-23C are computer models showing the first embodiment tuberosity augment (FIG. 23A), the second embodiment expanded tuberosity component (FIG. 23B, and the third embodiment superiorly shifted tuberosity component (FIG. 23C) positioned on a lateral humerus.

The augment member 32 of FIG. 22A, FIG. 22B, FIG. 22C, and FIG. 22D with the superiorly shifted bulbous surface 35 can improve the wrapping angle and moment arm for the normal shoulder and for each of the aforementioned prosthesis designs (Grammont reverse shoulder, Encore reverse shoulder, Equinoxe® reverse shoulder) as described in FIG. 23A, FIG. 23B and FIG. 23C and Table 4.

In an embodiment, the addition of the augment member 32 of FIG. 22A, FIG. 22B, FIG. 22C, and FIG. 22D increases the deltoid wrapping for the normal shoulder from 48° to 90°, from 48° to 88°, from 48° to 86°, from 48° to 84°, from 48° to 82°, from 48° to 80°, from 48° to 78°, from 48° to 76°, from 48° to 74°, from 48° to 72°, from 48° to 70°, 48° to 68°, 48° to 66°, 48° to 64°, 48° to 62°, 48° to 60°, 48° to 58°, 48° to 56°, 48° to 54°, 48° to 52° or 48° to 50°. In an embodiment, the addition of the prosthetic augment increased the deltoid wrapping for the normal shoulder from 48° to 72°, as indicated in Table 4.

In an embodiment, the addition of the augment member 32 of FIG. 22A, FIG. 22B, FIG. 22C, and FIG. 22D increases the deltoid wrapping for the 36 Grammont shoulder (with 20° retroversion) from 8° to 42°, from 8° to 40°, from 8° to 38°, from 8° to 36°, from 8° to 34°, from 8° to 32°, from 8° to 30°, from 8° to 28°, from 8° to 26°, from 8° to 24°, from 8° to 22°, from 8° to 20°, from 8° to 18°, from 8° to 16°, from 8° to 14°, from 8° to 12° or from 8° to 10°. In an embodiment, the addition of the augment member 32 increased the deltoid wrapping for the 36 Grammont shoulder (with 20° retroversion) from 8° to 28°, as indicated in Table 4.

In an embodiment, the addition of the augment member 32 of FIG. 22A, FIG. 22B, FIG. 22C, and FIG. 22D increases the deltoid wrapping for the 32 Encore Reverse® shoulder from 28° to 61°, from 28° to 59°, from 28° to 57°, from 28° to 55°, from 28° to 53°, from 28° to 51°, from 28° to 49°, from 28° to 47°, from 28° to 45°, from 28° to 43°, from 28° to 41°, from 28° to 39°, from 28° to 37°, from 28° to 35° or from 28° to 33°. In an embodiment, the addition of the augment member 32 increased the deltoid wrapping for the 32 Encore Reverse® shoulder from 28° to 51°, as indicated in Table 4.

In an embodiment, the addition of the augment member 32 of FIG. 22A, FIG. 22B, FIG. 22C, and FIG. 22D increases the deltoid wrapping for the 38 Equinoxe® shoulder from 40° to 89°, from 40° to 87°, from 40° to 85°, from 40° to 83°, from 40° to 81° from 40° to 79°, from 40° to 77°, from 40° to 75°, from 40° to 73°, from 40° to 71° or from 40° to 69°. In an embodiment, the addition of the augment member 32 increased the deltoid wrapping for the 38 Equinoxe® shoulder from 40° to 81°, as indicated in Table 4.

TABLE 4

Wrapping of Middle Deltoid Around the Superiorly Shifted Augment Member 32

| | Abduction where deltoid doesn't wrap tuberosity augment |
|---|---|
| Normal Shoulder with Augment | 72° |
| 36 Grammont, 20° retroversion with Superiorly Shifted Augment | 28° |
| 32 Encore reverse ®, 20° retroversion with Superiorly Shifted Augment | 51° |
| 38 Equinoxe ®, 20° retroversion with Superiorly Shifted Augment | 81° (impingement; middle deltoid still wrapped at this degree of elevation) |

As can be seen in the computer models and the results shown in Tables 2-4, the 38 Equinoxe®, 20° retroversion reverse shoulder prosthesis used in conjunction with any of the augment members of the present invention, as depicted in FIG. 8A, FIG. 8B, FIG. 8C, FIG. 8D, FIG. 17A, FIG. 17B, FIG. 17C, FIG. 17D, FIG. 22A, FIG. 22B, FIG. 22C, and FIG. 22D, provides an implant system that, when the arm reaches 81° abduction, deltoid wrapping still occurs around the augment.

An augment member of the present invention is offered in various sizes and curvatures to selectively (intraoperatively or otherwise) fit the anatomy of the intended bone/muscle shape/location or be modified to fit based upon patient, bone, tissue, and/or surgical factors. An augment member of the present invention may be smooth (electro-polished) to prevent abrasion or damage to the muscle (or bone) as it slides over the augment. As described in FIG. 8A, FIG. 8B, FIG. 8C, FIG. 8D, FIG. 17A, FIG. 17B, FIG. 17C, FIG. 17D, FIG. 22A, FIG. 22B, FIG. 22C, and FIG. 22D, an augment member of the present invention may be modular to allow multiple sizes or multiple offsets of tuberosity elements to attach relative to the base fixation component to facilitate intraoperative trialing to ensure adequate stability. In addition to being modular, an augment member of the present invention may have a mobile bearing component attaching to the bone (relative to the base fixation component) that permits contact with the muscle during multiple different motions.

FIG. 24A, FIG. 24B, FIG. 24C, and FIG. 24D and FIG. 25A, FIG. 25B, FIG. 25C, and FIG. 25D show a fourth embodiment of a prosthetic augment 40 of the present disclosure that is asymmetric and provided for a left humerus (FIG. 24A, FIG. 24B, FIG. 24C, and FIG. 24D) and a right humerus (FIG. 25A, FIG. 25B, FIG. 25C, and FIG. 25D). The prosthetic augment 40 includes an augment member 42 configured to extend a length of a patient's bone, the augment member 42 having a first face 44 adapted for receiving contact with the patient's bone and a second face 46 adapted for receiving contact with the underbelly of a muscle of the patient, the augment member 42 having a proximal end PE toward a head of the patient and a distal end DE toward a hip of the patient, wherein the augment member 42 includes a bulbous surface 45 resulting in a thickness of the augment member 42 being non-uniform from the distal end DE to the proximal end PE. In an embodiment, an edge of the distal end DE of the augment member 42 is curved. In an embodiment, an edge of the proximal end PE of the augment member 42 is curved. The prosthetic augment 40 may further comprise locking bone screws. The bulbous surface 45 is sufficiently elongated to accommodate the anatomic variance of the bone. The second face 46 has a variable radius meaning that at least two different constant radii exist on the second face 46.

Figure 25A:
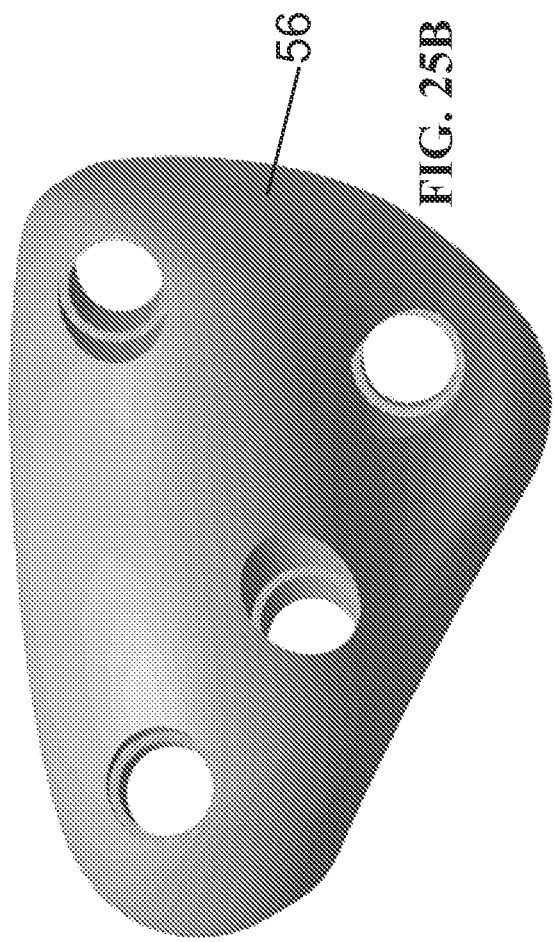
Figure 25B:
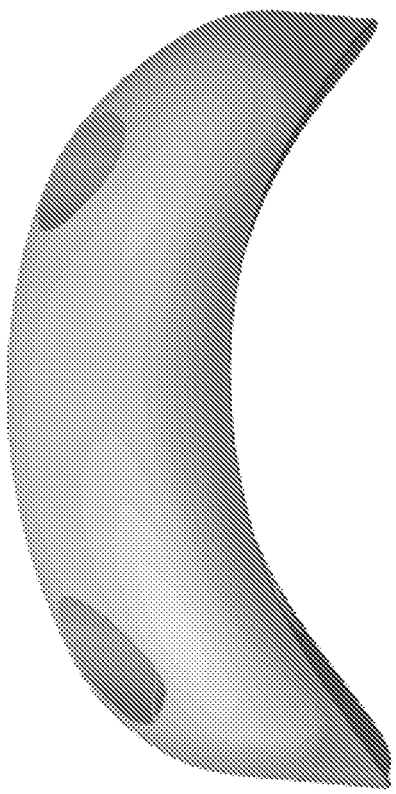
Figure 25C:
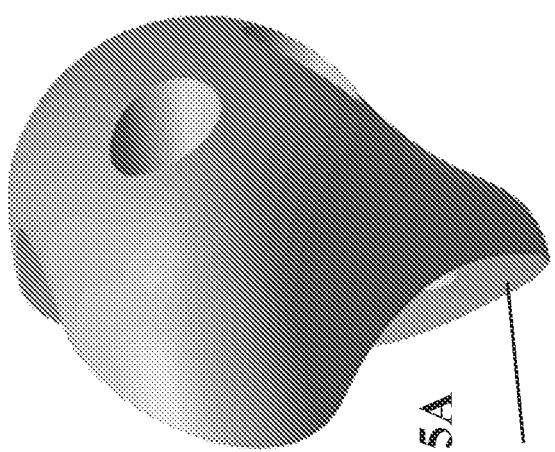
Figure 25D:
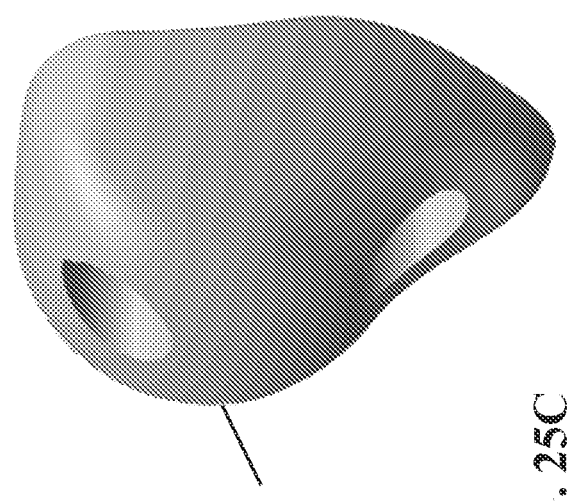

FIGS. 24A and 25A show the thickness between first face 44 and second face 46 is non-uniform. A first thickness is defined between the first face 44 and the second face 46 at a first position on the augment member 42. A second thickness is defined between the first face 44 and the bulbous surface 45 of the second face 46. The first thickness and the second thickness are not equivalent so as to result in the augment member 42 having a non-uniform thickness. The augment member 42 comprises variable thicknesses at multiple positions. In an embodiment, the first thickness is less than about 5 mm. In an embodiment, the first thickness ranges from about 1 mm to less than about 5 mm. In an embodiment, the first thickness ranges from about 1 mm to about 4 mm. In an embodiment, the first thickness ranges from about 2 mm to about 3 mm. In an embodiment, the second thickness ranges from above 6 mm to about 50 mm. In an embodiment, the second thickness ranges from about 10 mm to about 46 mm. In an embodiment, the second thickness ranges from about 14 mm to about 42 mm. In an embodiment, the second thickness ranges from about 18 mm to about 38 mm. In an embodiment, the second thickness ranges from about 22 mm to about 34 mm. In an embodiment, the second thickness ranges from about 26 mm to about 30 mm. In an embodiment, the second thickness ranges from about 11 mm to about 19 mm. In an embodiment, the second thickness ranges from about 6 mm to about 40 mm. In an embodiment, the second thickness ranges from about 6 mm to about 30 mm. In an embodiment, the second thickness ranges from about 6 mm to about 20 mm. In an embodiment, the second thickness ranges between about 6 mm to about 10 mm. In an embodiment, the second thickness ranges between about 6.5 mm to about 9.5 mm. In an embodiment, the second thickness ranges between about 7 mm to about 9 mm. In an embodiment, the second thickness ranges between about 7.5 mm to about 8.5 mm.

First face 44 can be contoured (as illustrated) or can be flat. The bulbous surface 45 is sufficiently designed to result in an increase in the wrapping point of a deltoid muscle around the greater tuberosity and also an increase in the abductor moment arm of the deltoid muscle. In an embodiment, the bulbous surface 45 is shaped round to prevent abrasion of the muscle as the augment member 42 fits between the underbelly of the muscle and the lateral humeral bone. The curvature and location of the augment member 42 profile is sufficiently designed so that the center of rotation of the bulbous surface 45 approaches that of the native joint so that the compression of the deltoid muscle will result in a stabilizing force. In an embodiment, the size of the augment member 42 and the amount of lateralization is limited by the impingement that could result with the acromion at high arm elevation. In an embodiment, the superior portion of the augment member 42 is intended to be thin with a thickness so that the augment member 42 can potentially slide under the acromion if placed high or be low profile so that the augment member 42 doesn't impinge.

Figure 26C:
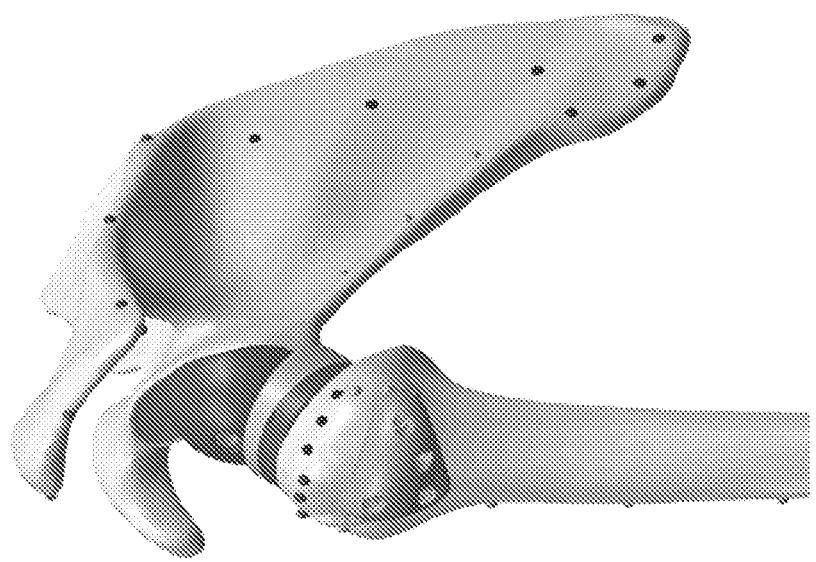
FIGS. 26A-26C are computer models showing the fourth embodiment tuberosity augment of the present disclosure positioned on the greater tuberosity of the left lateral humerus having a 38 mm Equinoxe® Reverse Shoulder prosthesis.
Figure 26B:
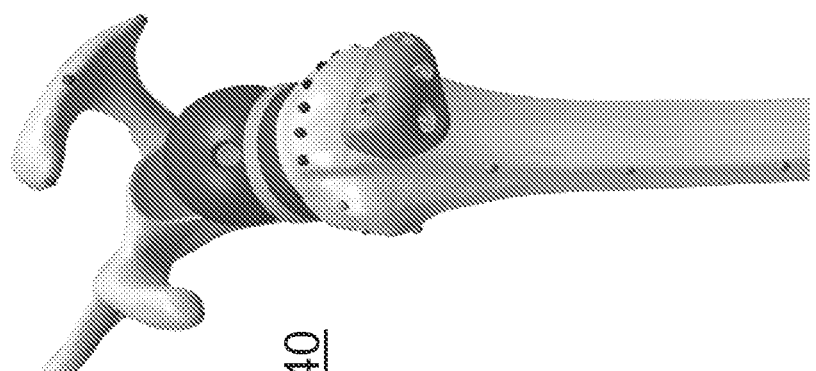
Figure 26A:
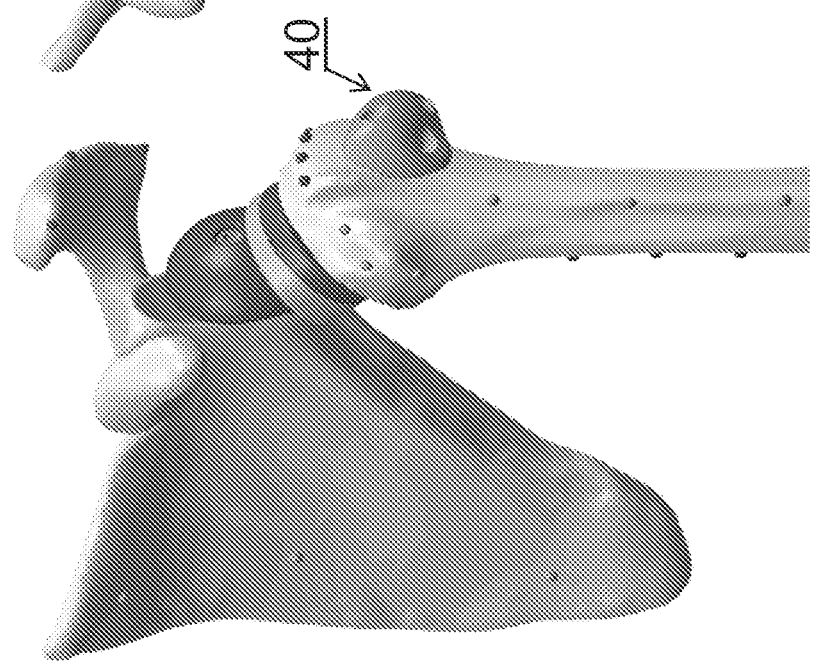

FIG. 26A, FIG. 26B and FIG. 26C are computer models showing the fourth embodiment augment member 40 of the present disclosure positioned on the greater tuberosity of the left lateral humerus having a 38 mm Equinoxe® Reverse Shoulder prosthesis.

FIG. 27A, FIG. 27B, FIG. 27C, FIG. 27D, FIG. 27E, FIG. 28A, FIG. 28B, FIG. 28C, FIG. 28D and FIG. 28E show views of a sixth embodiment of a prosthetic augment 50 of the present disclosure that is asymmetric and provided for a left humerus (FIG. 27A, FIG. 27B, FIG. 27C, FIG. 27D, and FIG. 27E) and a right humerus (FIG. 28A, FIG. 28B, FIG. 28C, FIG. 28D and FIG. 28E). The prosthetic augment 50 includes an augment member 52 configured to extend a length of a patient's bone, the augment member 52 having a first face 54 adapted for receiving contact with the patient's bone and a second face 56 adapted for receiving contact with the underbelly of a muscle of the patient, the augment member 52 having a proximal end PE toward a head of the patient and a distal end DE toward a hip of the patient, wherein the augment member 52 includes a bulbous surface 55 resulting in a thickness of the augment member 52 being non-uniform from the distal end DE to the proximal end PE. In an embodiment, an edge of the distal end DE of the augment member 52 is curved. In an embodiment, an edge of the proximal end PE of the augment member 52 is curved. The prosthetic augment 50 may further comprise locking bone screws. The bulbous surface 55 is sufficiently elongated to accommodate the anatomic variance of the bone. The second face 56 has a variable radius meaning that at least two different constant radii exist on the second face 56.

Figures 28A, 28B, 28C, 28D, 28E:
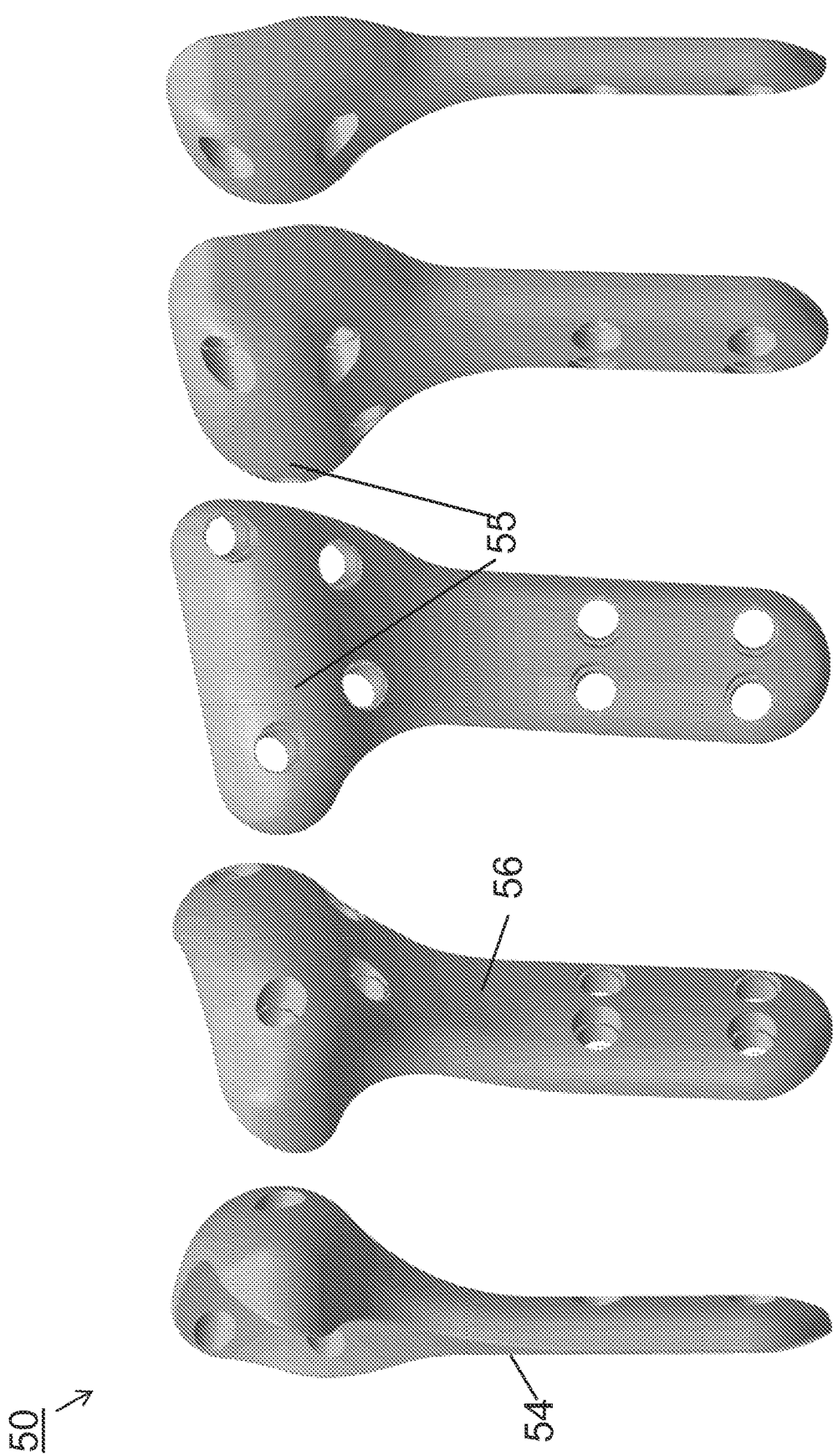

FIGS. 27A and 28A show the thickness between first face 54 and second face 56 is non-uniform. A first thickness is defined between the first face 54 and the second face 56 at a first position on the augment member 52. A second thickness is defined between the first face 54 and the bulbous surface 55 of the second face 56. The first thickness and the second thickness are not equivalent so as to result in the augment member 52 having a non-uniform thickness. In an embodiment, the first thickness is less than about 5 mm. The augment member 52 comprises variable thicknesses at multiple positions. In an embodiment, the first thickness ranges from about 1 mm to less than about 5 mm. In an embodiment, the first thickness ranges from about 1 mm to about 4 mm. In an embodiment, the first thickness ranges from about 2 mm to about 3 mm. In an embodiment, the second thickness ranges from above 6 mm to about 50 mm. In an embodiment, the second thickness ranges from about 10 mm to about 46 mm. In an embodiment, the second thickness ranges from about 14 mm to about 42 mm. In an embodiment, the second thickness ranges from about 18 mm to about 38 mm. In an embodiment, the second thickness ranges from about 22 mm to about 34 mm. In an embodiment, the second thickness ranges from about 26 mm to about 30 mm. In an embodiment, the second thickness ranges from about 11 mm to about 19 mm. In an embodiment, the second thickness ranges from about 6 mm to about 40 mm. In an embodiment, the second thickness ranges from about 6 mm to about 30 mm. In an embodiment, the second thickness ranges from about 6 mm to about 20 mm. In an embodiment, the second thickness ranges between about 6 mm to about 10 mm. In an embodiment, the second thickness ranges between about 6.5 mm to about 9.5 mm. In an embodiment, the second thickness ranges between about 7 mm to about 9 mm. In an embodiment, the second thickness ranges between about 7.5 mm to about 8.5 mm.

First face 54 can be contoured (as illustrated) or can be flat. The bulbous surface 55 is sufficiently designed to result in an increase in the wrapping point of a deltoid muscle around the greater tuberosity and also an increase in the abductor moment arm of the deltoid muscle. In an embodiment, the bulbous surface 55 is shaped round to prevent abrasion of the muscle as the augment member 52 fits between the underbelly of the muscle and the lateral humeral bone. The curvature and location of the augment member 52 profile is sufficiently designed so that the center of rotation of the bulbous surface 55 approaches that of the native joint so that the compression of the deltoid muscle will result in a stabilizing force. In an embodiment, the size of the augment member 52 and the amount of lateralization is limited by the impingement that could result with the acromion at high arm elevation. In an embodiment, the superior portion of the augment member 52 is intended to be thin with a thickness so that the augment member 52 can potentially slide under the acromion if placed high or be low profile so that the augment member 52 doesn't impinge.

In an embodiment, an edge of the distal end DE of the augment member 52 is curved. In an embodiment, an edge of the proximal end PE of the augment member 52 is curved. In an embodiment, the augment member 52 ranges from about 20.00 mm to about 50.00 mm in length. In an embodiment, the augment member 52 ranges from about 21.00 mm to about 49.00 mm in length. In an embodiment, the augment member 52 ranges from about 22.00 mm to about 48.00 mm in length. In an embodiment, the augment member 52 ranges from about 23.00 mm to about 47.00 mm in length. In an embodiment, the augment member 52 ranges from about 24.00 mm to about 46.00 mm in length. In an embodiment, the augment member 52 ranges from about 25.00 mm to about 45.00 mm in length. In an embodiment, the augment member 52 ranges from about 26.00 mm to about 44.00 mm in length. In an embodiment, the augment member 52 ranges from about 27.00 mm to about 43.00 mm in length. In an embodiment, the augment member 52 ranges from about 28.00 mm to about 42.00 mm in length. In an embodiment, the augment member 52 ranges from about 29.00 mm to about 41.00 mm in length. In an embodiment, the augment member 52 ranges from about 31.00 mm to about 39.00 mm in length. In an embodiment, the augment member 52 ranges from about 32.00 mm to about 38.00 mm in length. In an embodiment, the augment member 52 ranges from about 33.00 mm to about 37.00 mm in length. In an embodiment, the augment member 52 ranges from about 34.00 mm to about 36.00 mm in length. In an embodiment, the augment member 52 ranges from about 50.00 mm to about 60.00 mm in length. In an embodiment, the augment member 52 ranges from about 51.00 mm to about 59.00 mm in length. In an embodiment, the augment member 52 ranges from about 52.00 mm to about 58.00 mm in length. In an embodiment, the augment member 52 ranges from about 53.00 mm to about 57.00 mm in length. In an embodiment, the augment member 52 ranges from about 54.00 mm to about 56.00 mm in length. In an embodiment, the augment member 52 ranges from about 54.50 mm to about 55.50 mm in length. In an embodiment, the augment member 52 is about 55.00 mm in length.

Figure 29A:
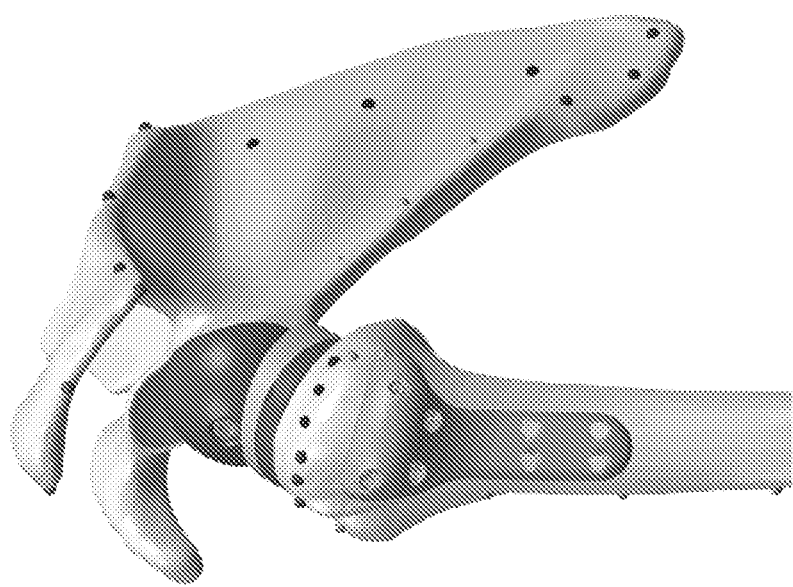
FIGS. 29A-29C are computer models showing the sixth embodiment tuberosity augment of the present disclosure positioned on the greater tuberosity of the left lateral humerus having a 38 mm Equinoxe® Reverse Shoulder prosthesis.
Figure 29B:
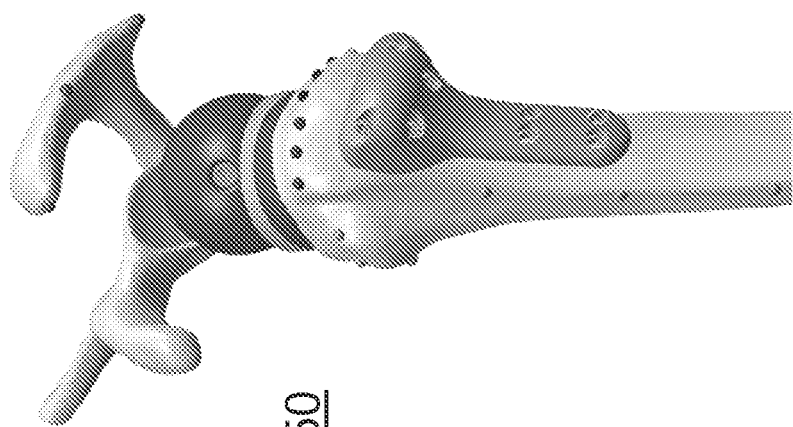
Figure 29C:
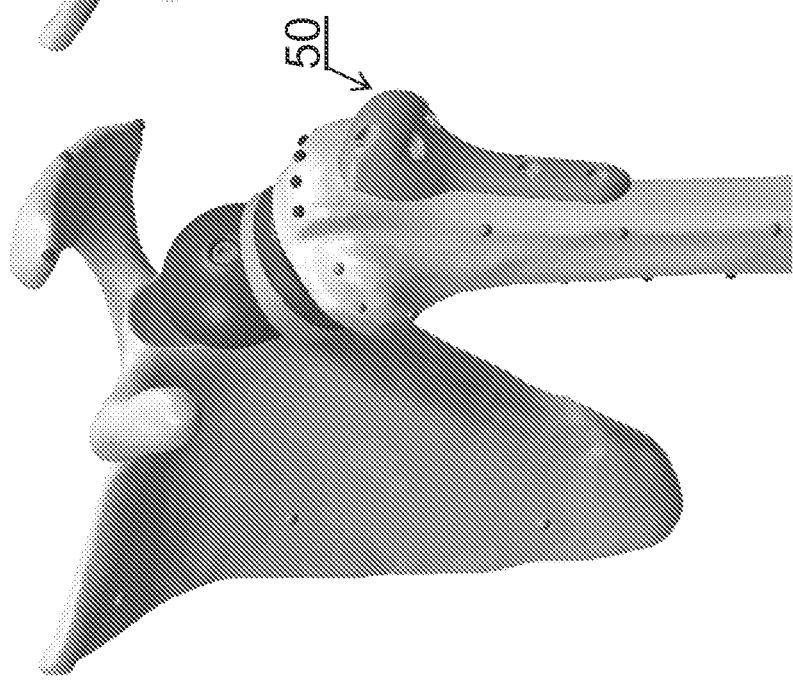

FIG. 29A, FIG. 29B and FIG. 29C are computer models showing the sixth embodiment augment member 52 of the present disclosure positioned on the greater tuberosity of the left lateral humerus having a 38 mm Equinoxe® Reverse Shoulder prosthesis. The augment member 52 is sufficiently designed to re-direct the deltoid muscle line of action to a further lateral position and thus increase the moment arm of that muscle. The augment member 52 is attached to the proximal lateral humerus and essentially focally enlarges the tuberosity without altering the rotator cuff insertions. In an embodiment, by virtue of increasing the deltoid moment arm, the deltoid augment member 52 will increase the deltoid moment arm, and decrease deltoid, posterior cuff, and joint reaction forces necessary to perform a given motion relative to a joint without the augment member 52. In an embodiment, less rotator cuff force is required to stabilize the glenohumeral joint during abduction when the lateral humerus includes the augment member 52 and the resultant joint reaction force (JRF) is lower with the augment member 52.

A second-generation cadaver shoulder model that utilizes simulated neuromuscular control was used for a study. This model is similar to that described by Hansen et al (Biomechanics of massive rotator cuff tears: implications for treatment. J Bone Joint Surg Am. 2008 February; 90(2):316-25), with upgrades that allow use of metal in the field and greater refresh rate for the control loop. Stepper motors (Industrial Devices Corporation, Salem, N.H.) actuate cables that are attached to the rotator cuff tendons and deltoid tuberosity. Force transducers measure the tension developed in each cable as active closed-loop position and orientation control algorithms control each motor. This allows the controller to simulate in vivo glenohumeral kinematics. As presently configured, the controller utilizes active optical markers (Northern Digital, Inc., Waterloo, Ontario, Canada) to track motion, and a six-axis load cell measures the resultant joint reaction force at the glenohumeral joint. One cadaver full upper extremity specimen was tested in scapular plane abduction without any artificial external constraints from 15° to 65° with full mass of the upper extremity. The tests were performed with the elbow extended and with the elbow flexed at 90° to simulate the internal rotation torque associated with many activities of daily living (ADLs). Eight conditions were tested, four conditions with the anatomic shoulder and four conditions with different reverse shoulder prostheses. The four conditions with the native anatomic shoulder are: intact shoulder with and without the augment member 40, and a simulated supraspinatus tendon tear with and without the augment member 40. The four conditions with shoulder prostheses are: 42 mm Grammont RSA with and without the deltoid augment, and 42 mm Equinoxe® RSA with and without the deltoid augment. The subscapularis was repaired with the Grammont but not with the Equinoxe® as that is the typical practice for each device clinically. Three trials were performed for each condition. Students-t test with alpha set at 0.05 was utilized.

Figure 30B:
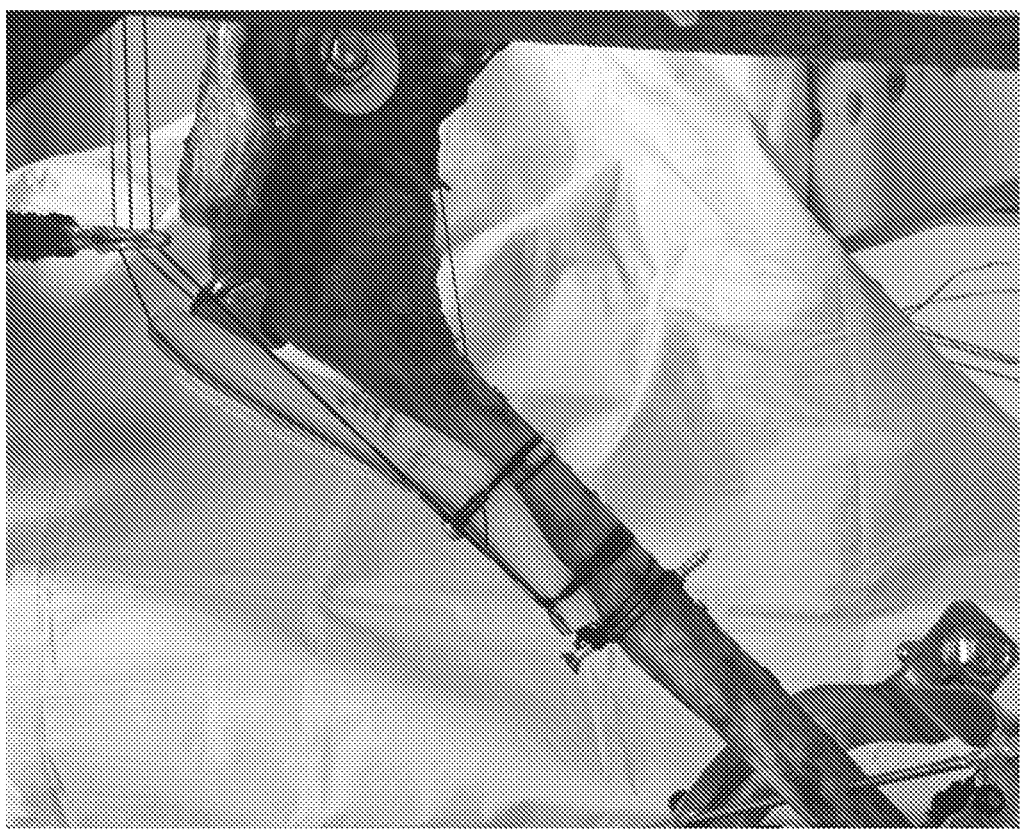
FIG. 30A and FIG. 30B are photographs of a shoulder controller simulating scapular abduction of the native shoulder with the fourth embodiment tuberosity augment of the present disclosure positioned at Low (FIG. 30A) and Mid (FIG. 30B) humeral elevation.
Figure 30A:
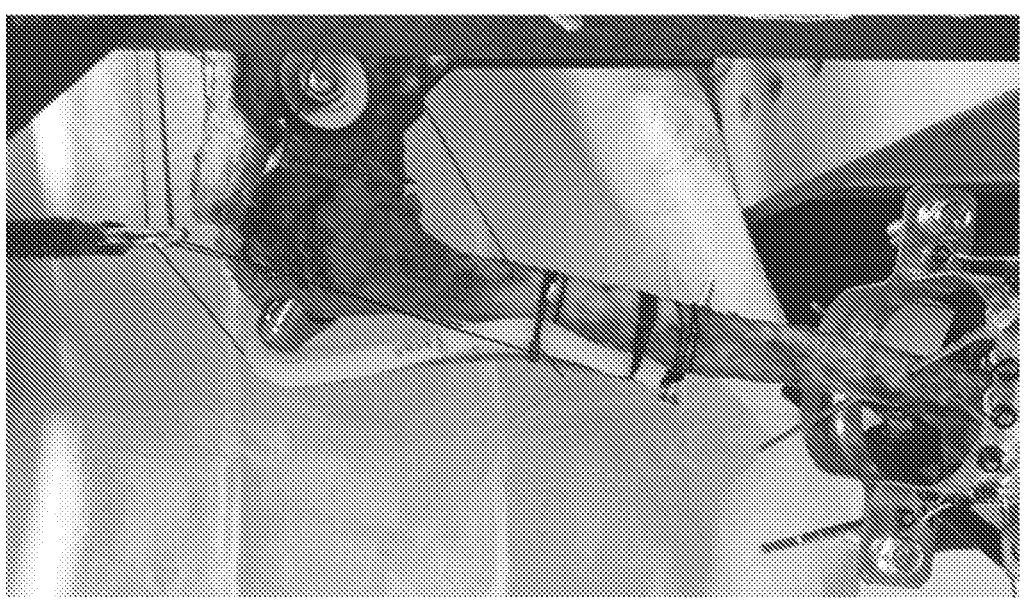
Figures 31A, 31B:
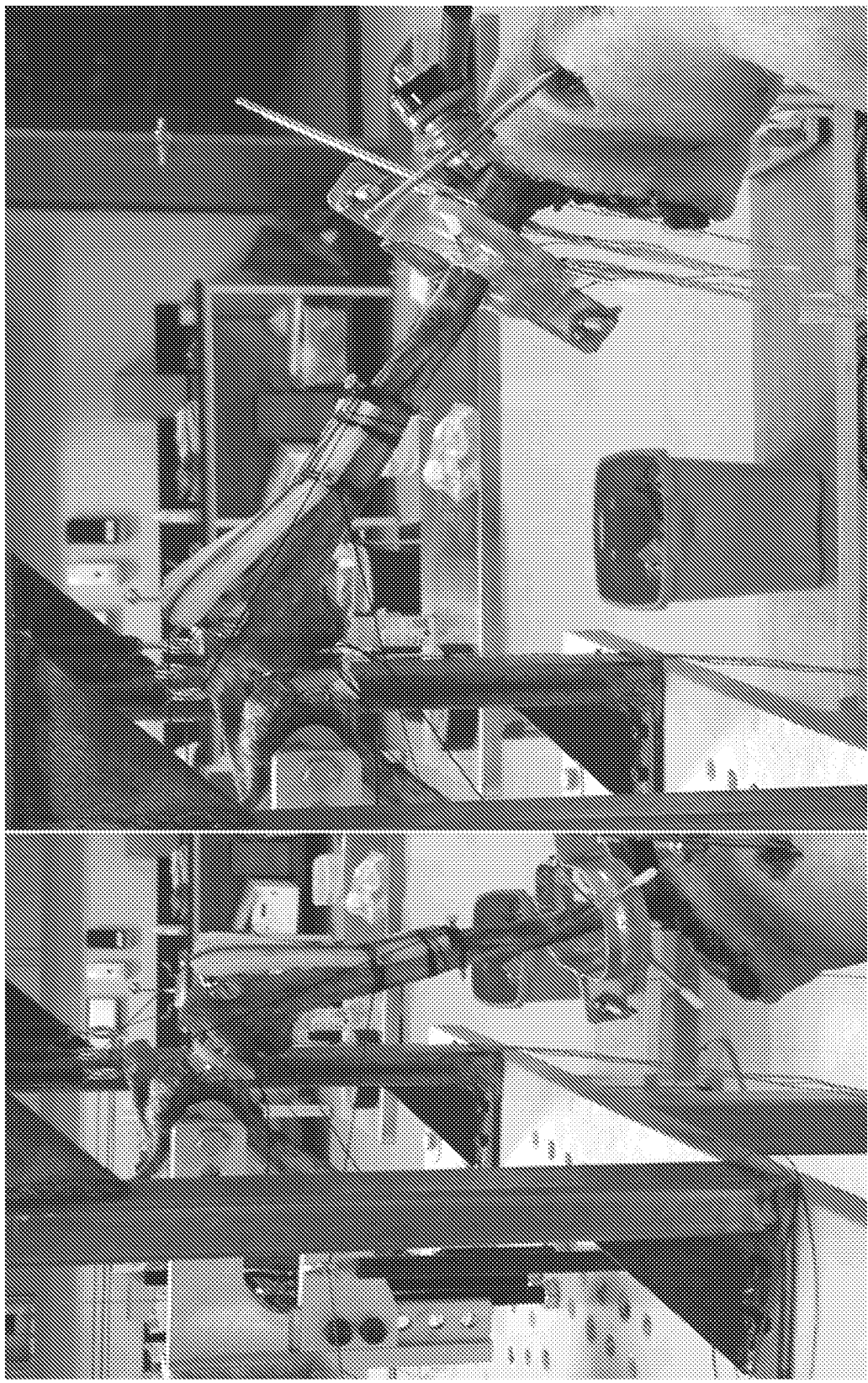
FIG. 31A and FIG. 31B are photographs of a shoulder controller simulating scapular abduction of the 42 mm Equinoxe® Reverse Shoulder prosthesis with the fourth embodiment tuberosity augment of the present disclosure positioned at Low (FIG. 31A) and High (FIG. 31B) humeral elevation.

FIG. 30A and FIG. 30B are photographs of a shoulder controller simulating scapular abduction of the native shoulder with the fourth embodiment augment member 40 of the present disclosure positioned at Low (FIG. 30A) and Mid (FIG. 30B) humeral elevation. FIG. 31A and FIG. 31B are photographs of a shoulder controller simulating scapular abduction of the 42 mm Equinoxe® Reverse Shoulder prosthesis with the fourth embodiment augment member 40 of the present disclosure positioned at Low (FIG. 31A) and High (FIG. 31B) humeral elevation.

Figure 32:
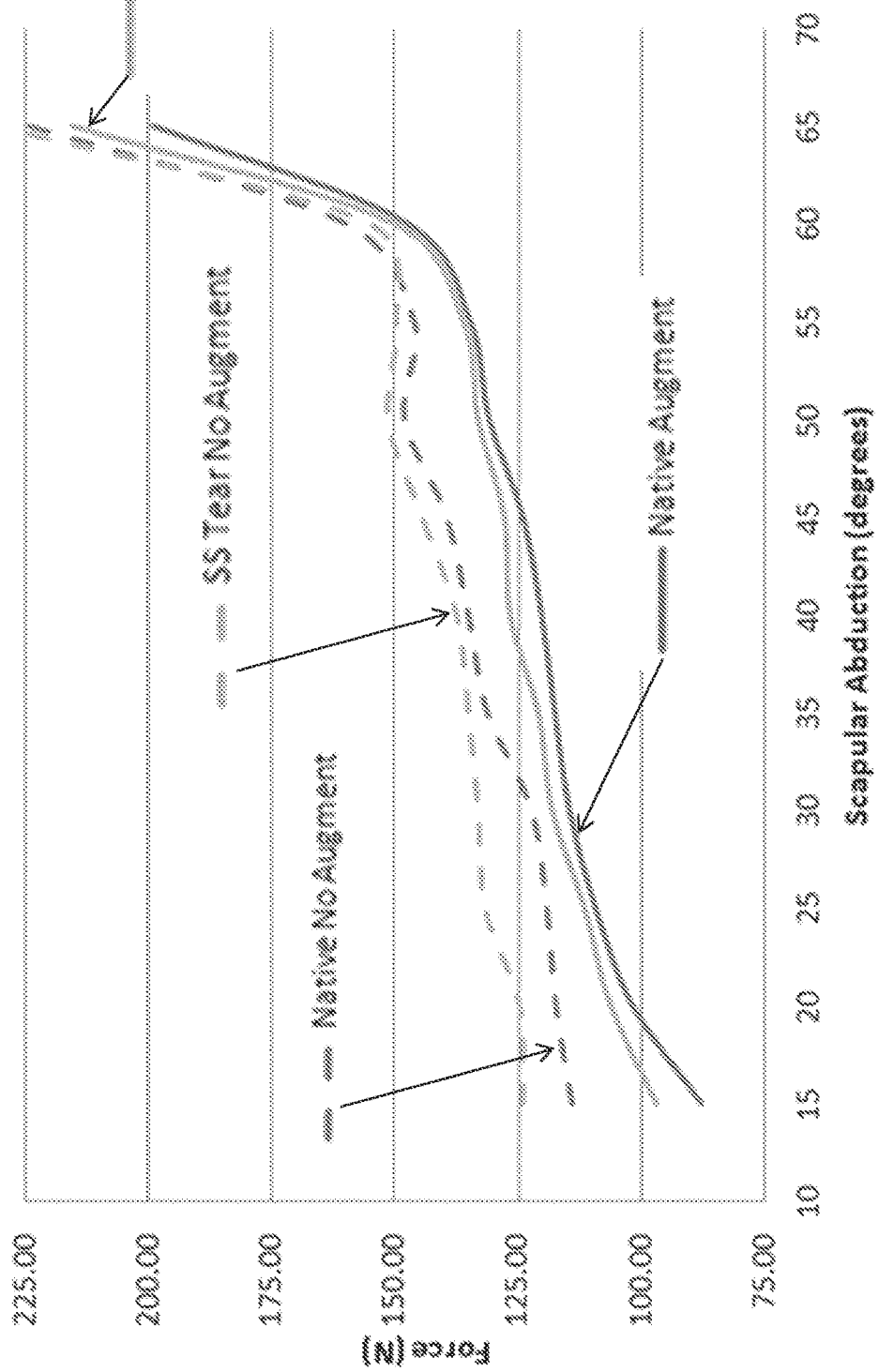
FIG. 32 is a graph comparison of the deltoid force required for abduction with the native anatomic shoulder (with and without augment) and the native shoulder with a supraspinatus tear (with and without augment).
Figure 33:
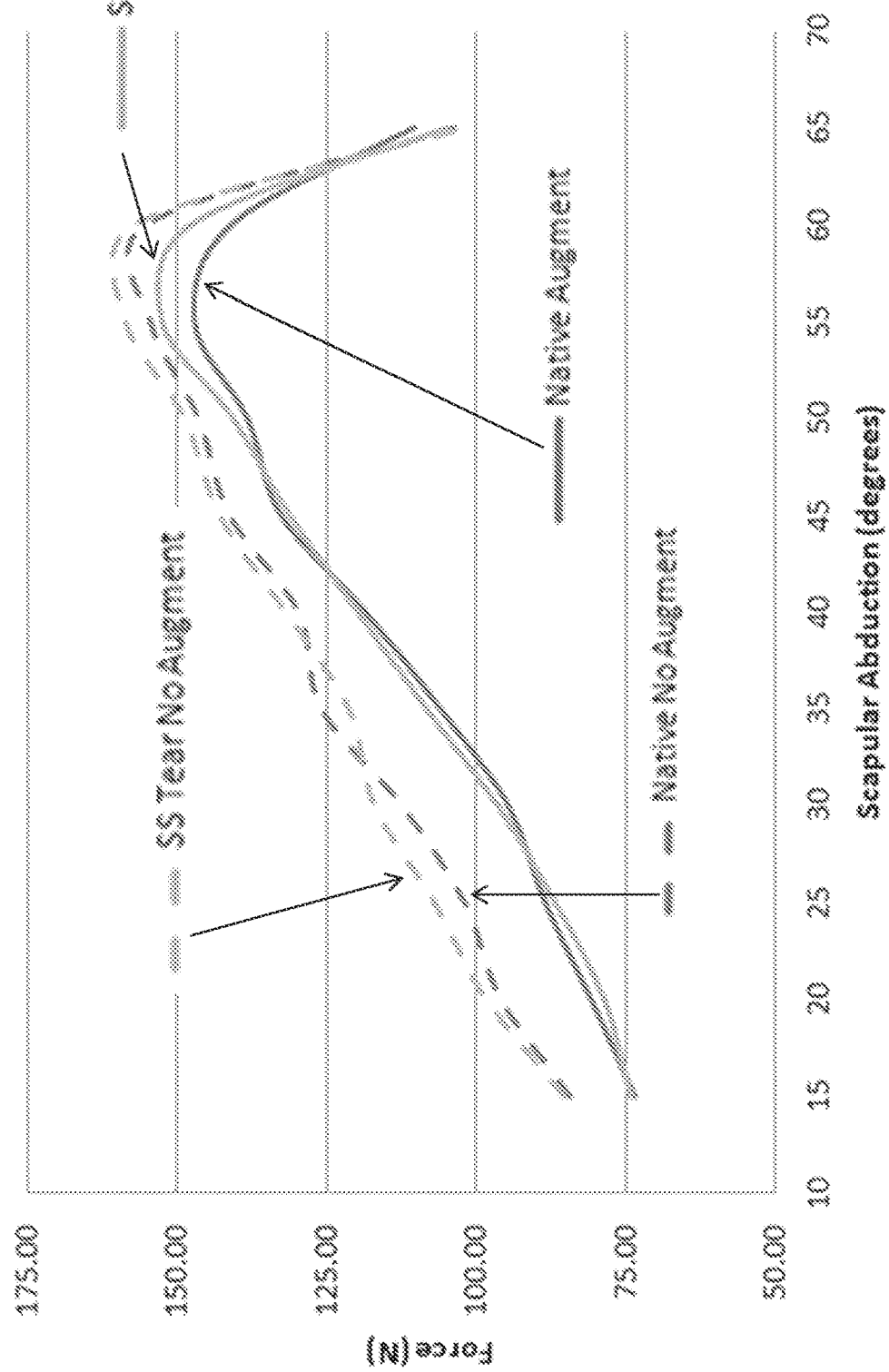
FIG. 33 is a graph comparison of the posterior cuff force required for abduction with the native anatomic shoulder (with and without augment) and the native shoulder with a supraspinatus tear (with and without augment).
Figure 34:
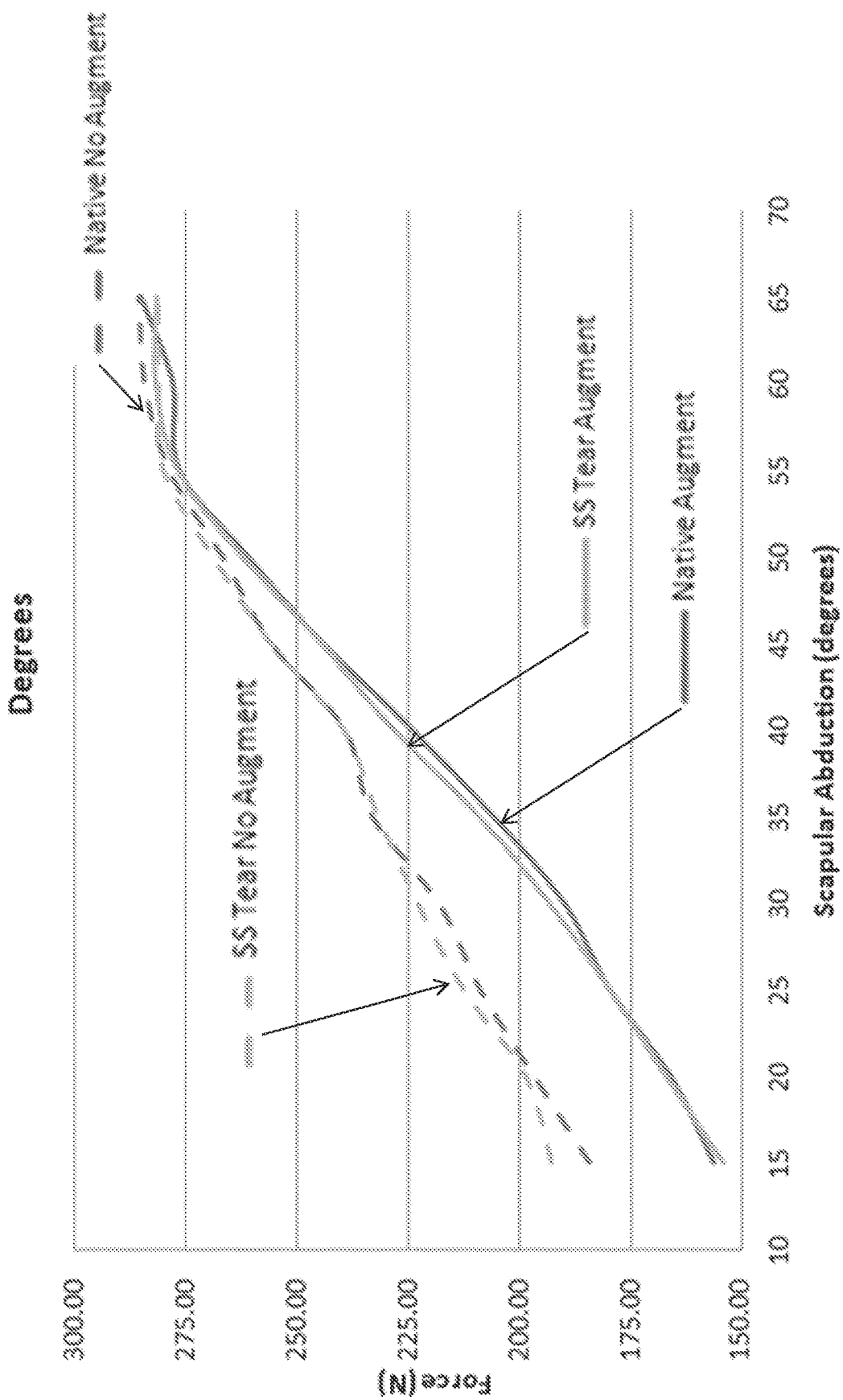
FIG. 34 is a graph comparison of joint reaction forces (JRF) with the native anatomic shoulder (with and without augment) and the native shoulder with a supraspinatus tear (with and without augment).
Figure 35:
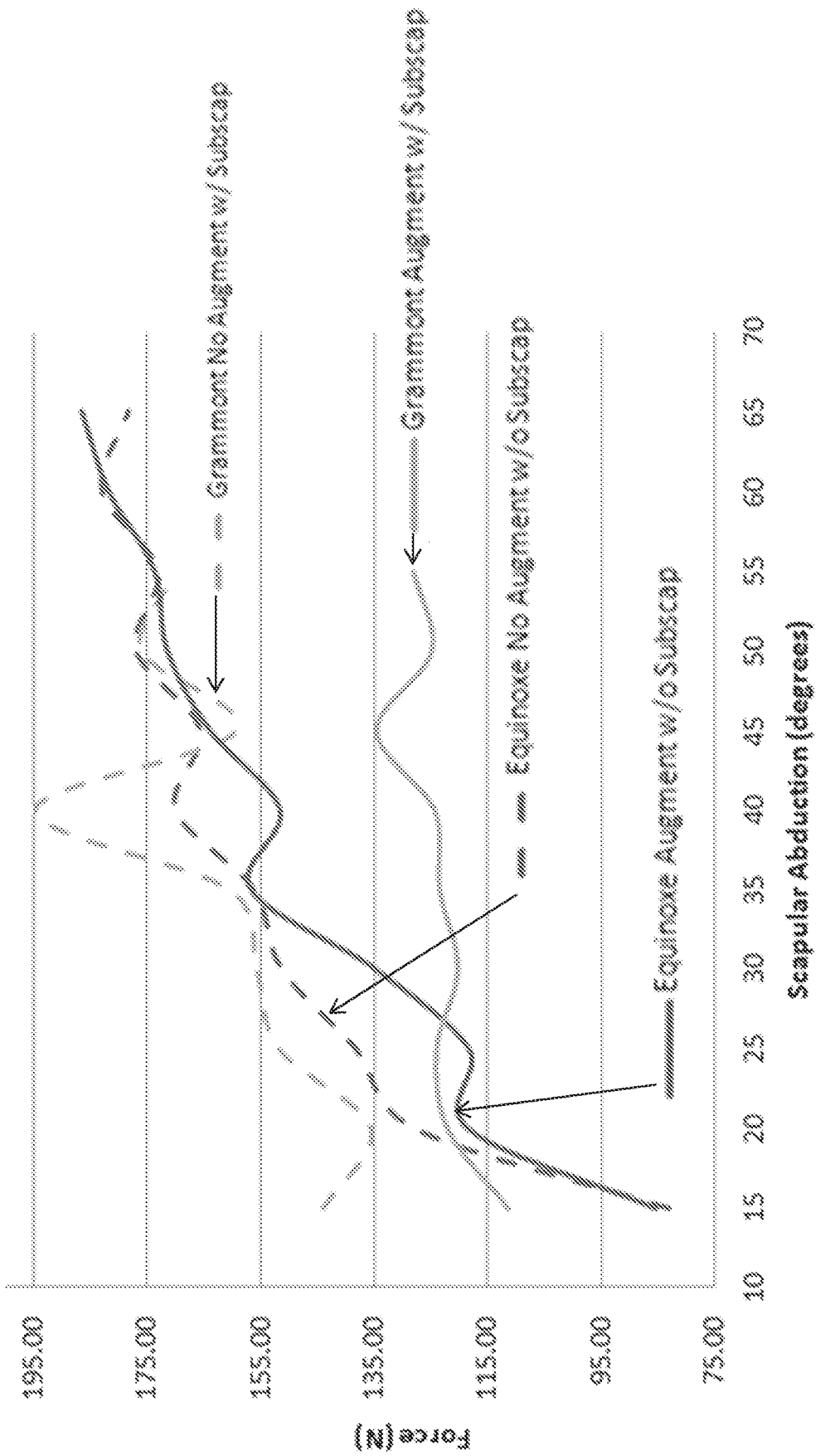
FIG. 35 is a graph comparison of the deltoid force required for abduction with the 42 mm Equinoxe® reverse shoulder prostheses (with and without augment) and the 42 mm Grammont reverse shoulder (with and without augment).
Figure 36:
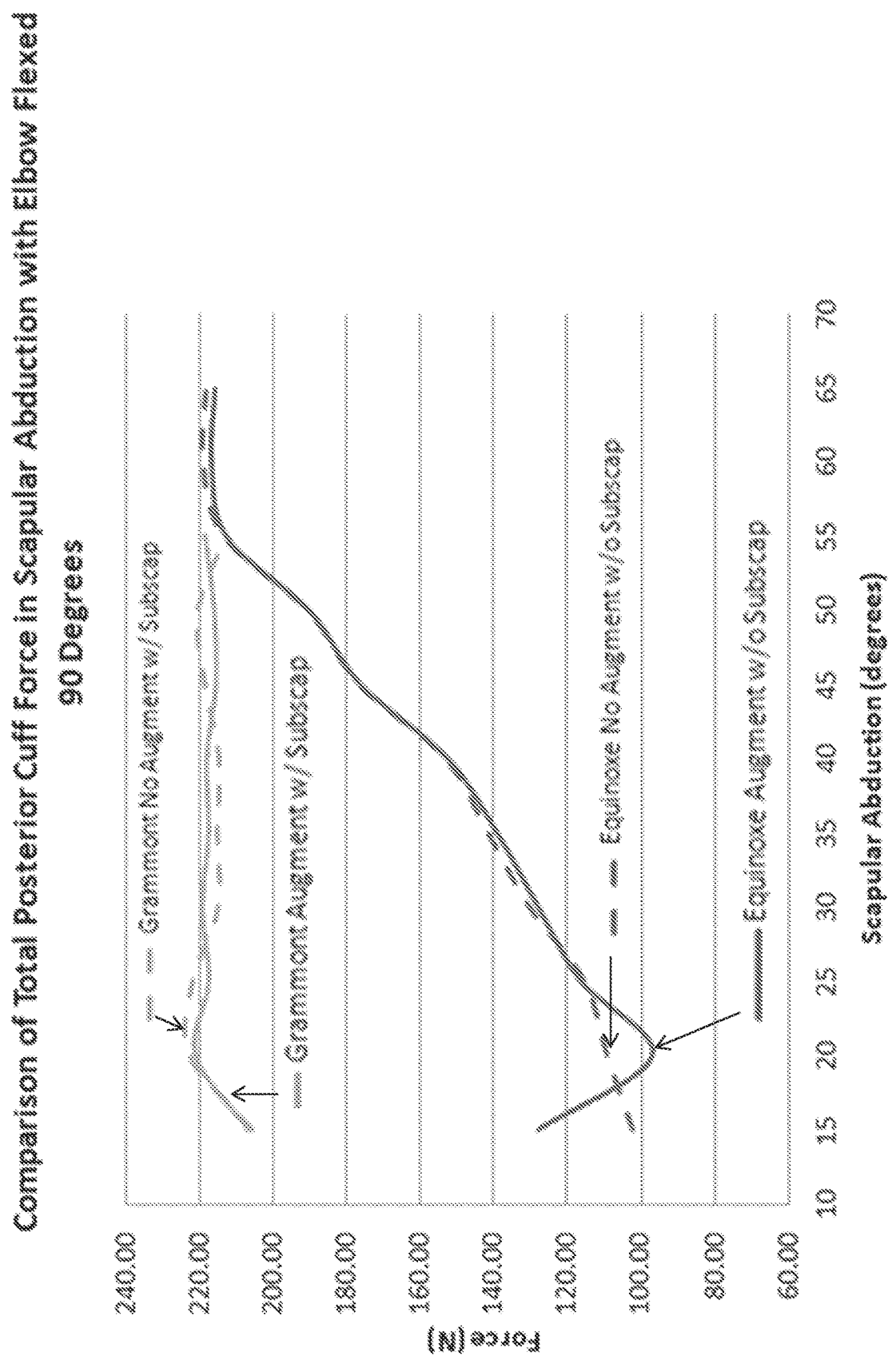
FIG. 36 is a graph comparison of the posterior cuff force required for abduction with the 42 mm Equinoxe® reverse shoulder prostheses (with and without augment) and the 42 mm Grammont reverse shoulder (with and without augment).
Figure 37:
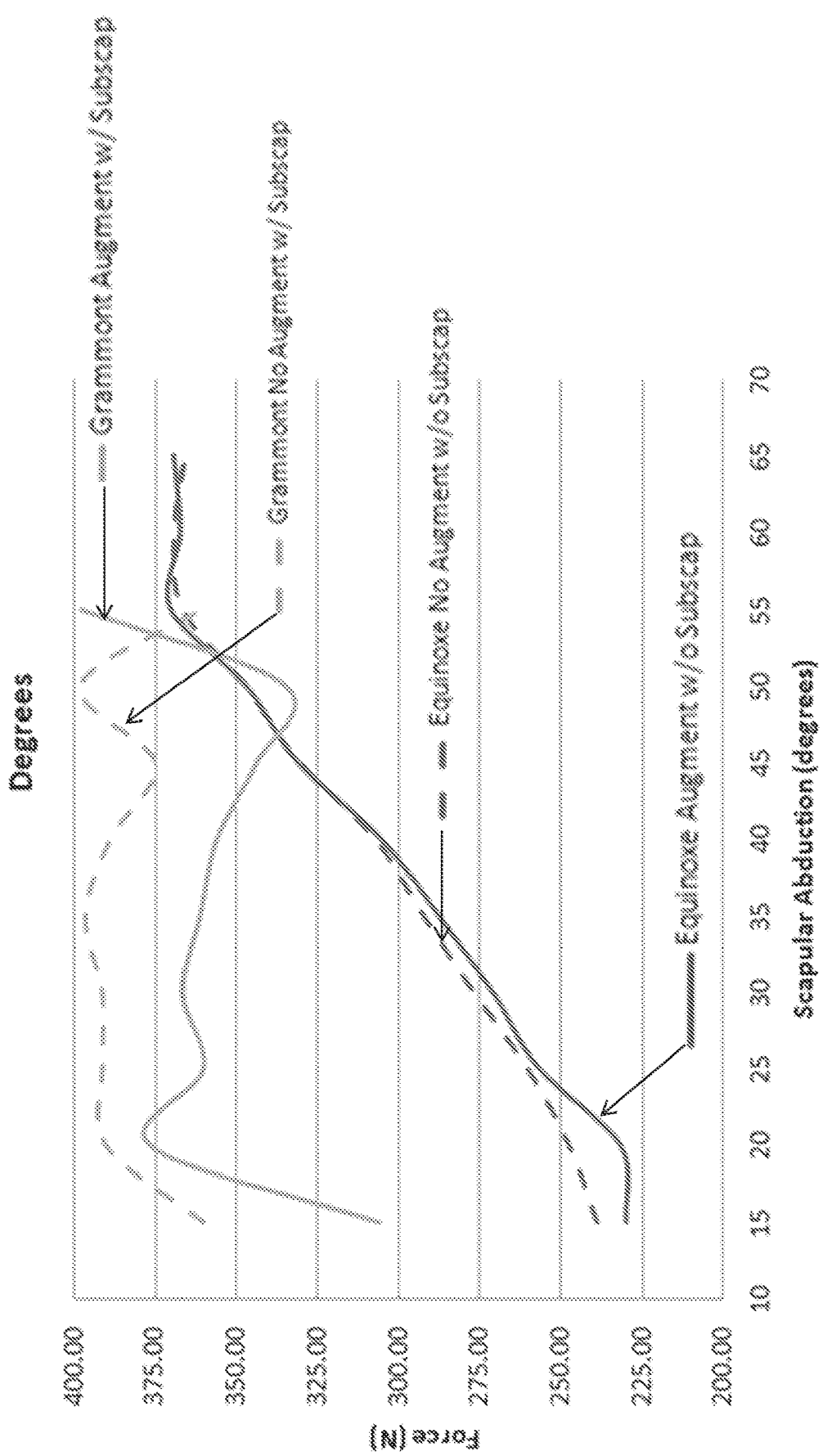
FIG. 37 is a graph comparison of joint reaction forces (JRF) for four conditions with 42 mm Equinoxe® reverse shoulder prostheses (with and without augment) and the 42 mm Grammont reverse shoulder (with and without augment).

For the native anatomic shoulder, a greater force was required in the deltoid and posterior cuff for the supraspinatus tear condition compared to the intact. (FIG. 32 and FIG. 33) For both the intact and the supraspinatus tear conditions, the augment member 40 decreased the deltoid force requirement, the posterior cuff force requirement, and the joint reaction force compared to the no augment condition (FIG. 32, FIG. 33, and FIG. 34). These decreases were most pronounced during the first 35° of abduction. For the reverse shoulder prostheses, during scapular elevation with the elbow flexed, the addition of the augment member 40 on the Equinoxe® shoulder increased the middle deltoid abductor moment arm by 3.7 mm (from 60.9 to 64.5 mm); similarly, the addition of the augment member 40 on the Grammont shoulder increased the middle deltoid abductor moment arm by 9.5 mm (from 59.5 to 69.1 mm). During Scapular elevation with the elbow extended, the addition of the augment member 40 on the Equinoxe® shoulder increased the middle deltoid abductor moment arm by 3.1 mm (from 65.1 to 68.3 mm); similarly, the addition of the augment member 40 on the Grammont shoulder increased the middle deltoid abductor moment arm by 5.8 mm (from 62.0 to 67.8 mm). Deltoid, posterior cuff, and joint reaction forces were higher for the Grammont RSA than for the Equinoxe® RSA (FIG. 35, FIG. 36, and FIG. 37). The augment member 40 decreased the deltoid force required for abduction, the posterior cuff force and the joint reaction force for both RSA designs although the effect was larger for the Grammont RSA.

In an embodiment, a prosthetic augment of the present invention produces a "supra-physiologic" moment arm for the deltoid which translates into less force required for abduction to generate the same abduction torque as the nominal condition. With less deltoid force tending to pull the humeral head superiorly, less rotator cuff force may be required to stabilize the humeral head in the center of the glenoid.

In an embodiment, the "augmented" shape of the proximal humerus, having a prosthetic augment of the present invention, increases the maximum deltoid wrapping angle, converting some of the deltoid force to a humeral head compressive force.

In an embodiment, concomitant use of a prosthetic augment of the present invention with RSA increases the deltoid moment arm. The larger effect seen with the Grammont RSA is likely a result of the medial humerus design of that particular prosthesis. For both designs (Equinoxe® RSA and Grammont RSA), the greater moment arm improves deltoid efficiency which may improve clinical outcomes including abduction strength after RSA.

In an embodiment, a prosthetic augment of the present invention increases the life of a RSA by decreasing the joint reaction force and thus decreasing polyethylene wear and the risk of acromial stress fractures.

An augment member of the present invention can be manufactured from different materials, including Co—Cr, stainless steel, titanium, carbon fiber, ceramic, PMMA bone cement, pyrocarbon, and/or bone graft. Additionally, an augment member of the present invention can be surface coated or treated with various processes to encourage fixation to the muscle and/or bone. A prosthetic augment of the present invention may connect directly to the bone, muscle, or humeral stem and may include various posts, screws (locking/compression/or poly-axial locking), fins, and or cables/sutures at various angles and positions to facilitate attachment of the augment to each aforementioned location on the humerus (which may or may not include a humeral stem in the intramedullary canal).

A prosthetic augment of the present invention may be provided in a kit. Further, a kit of the present invention may provide multiple prosthetic augments which vary with respect to their lengths, their bulbous surface size, their bulbous surface configuration, their thicknesses, and/or whether they include a left augment member or a right augment member. A kit of the present invention may further include at least one of posts, locking/compression screws, poly-axial locking screws, fins, cables and sutures.

An augment member of the present invention may be able to lateralize the humerus while maintaining the position of the center of rotation. In an embodiment, this increases the deltoid wrapping angle and allows the deltoid to compress the humerus into the glenoid, thereby improving stability.

The medical and healthcare sector represents one of the strongest vertical markets for applications of additive manufacturing (AM) and 3D printing (3DP) in which minuscule grains of plastic are sprayed in overlapping layers at high temperature and pressure to produce exquisitely precise, personalized, and complex prosthesis. In an embodiment, a Digital Imaging and Communications in Medicine (DICOM) file from a computed tomography (CT) scan or a magnet resonance imagining (MRI) scan of a patient's lateral humerus site can be converted into an STL file which can then be 3D printed. The 3D print can help visualize the lateral humerus site and plan an augment procedure of the present invention. This process can allow a surgeon to experience an extra dimension when planning an augment procedure, and the ability to fully manipulate and explore the area of interest (lateral humerus) in the real world before commencing surgery. To create an anatomically correct augment member of the present invention, MRI scans and CT scans can be utilized to design and build the prostheses prior to any surgery being carried out.

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

In an embodiment, a prosthetic augment includes an augment member configured to engage a bone, the augment member having a first face adapted for contacting the bone; and a second face adapted for contacting an underside of a muscle, wherein at least a portion of the second face includes a bulbous surface adapted to alter a wrapping angle of the muscle around the bone, and wherein the second face has a radius of curvature selected from one of a constant radius of curvature or a variable radius of curvature.

In an embodiment, a prosthetic augment includes an augment member configured to engage a bone, the augment member having a first face adapted for contacting the bone; and a second face adapted for contacting an underside of a muscle, wherein at least a portion of the second face includes a bulbous surface adapted to alter a wrapping angle of the muscle around the bone, wherein a first thickness is defined between the first face and the second face at a first position on the augment member, and wherein the first thickness ranges from about 1 mm to less than about 5 mm, wherein a second thickness is defined between the first face and the bulbous surface of the second face, and wherein the second thickness ranges from about 7 mm to about 23 mm, and wherein the first thickness and the second thickness are not equivalent so as to result in the augment member having a non-uniform thickness. The prosthetic augment may further include one or more locking bone screws.

In an embodiment, a kit for a long bone includes a prosthetic augment of the present disclosure and at least one locking bone screw.

A method includes positioning a prosthetic augment of the present disclosure between a bone and a muscle that wraps the bone; and engaging at least a portion of the first face of the augment member with the bone, wherein the bulbous surface of the second face is adapted to: (i) alter muscle wrapping around the bone, and (i) increase a moment arm of the muscle. In an embodiment, the augment member is engaged to the bone such that a center of rotation of the bulbous surface of the augment member approaches that of a native joint. In an embodiment, the augment member is engaged to the bone such that a center of rotation of the bulbous surface of the augment member approaches that of a native joint and compression of the wrapping muscle results in a stabilizing force. In an embodiment, the bone is a proximal humerus, and wherein the muscle is a deltoid muscle. In an embodiment, the bone is a posterior humerus, and wherein the muscle is a posterior rotator cuff muscle. In an embodiment, the bone is an anterior humerus, and wherein the muscle is an anterior shoulder muscle. In an embodiment, the anterior shoulder muscle is selected from the group consisting of subscapularis, teres major, pectoralis and latissimus. In an embodiment, the method is performed during anatomic shoulder arthroplasty. In an embodiment, the method is performed during reverse shoulder arthroplasty. In an embodiment, the method is performed during knee arthroplasty. In an embodiment, the method is performed during hip arthroplasty.

What is claimed is:

1. A prosthetic augment comprising:
an augment member configured to engage a proximal end of a humerus, the augment member comprising:
a proximal end and a distal end positioned opposite the proximal end, wherein the augment member is configured to engage the proximal end of the humerus such that the proximal end of the augment member is oriented toward a head of the patient and the distal end of the augment member is oriented toward a hip of the patient;
an anterior side extending from the proximal end of the augment member to the distal end of the augment member;
a posterior side extending from the proximal end of the augment member to the distal end of the augment member, the posterior side being positioned opposite the anterior side of the augment member;
a first face contoured to receive contact with the humerus, the first face extending from the proximal end of the augment member to the distal end of the augment member and from the anterior side of the augment member to the posterior side of the augment member, the first face being configured to contact bone of the humerus across an entirety of the first face; and
a second face opposite the first face, the second face extending from the proximal end of the augment member to the distal end of the augment member and from the anterior side of the augment member to the posterior side of the augment member, the second face being positioned opposite the first face of the augment member, wherein the second face is a smooth face that is adapted to prevent damage to an underside of a deltoid muscle when the underside of the deltoid muscle slides over the second face, and wherein at least a portion of the second face includes a bulbous surface adapted to increase a wrapping angle of the deltoid muscle around the humerus, thereby stabilizing a shoulder joint,
wherein a first thickness is defined between the first face and the second face at a first position on the augment member, and wherein the first thickness ranges from about 1 mm to less than about 5 mm,
wherein a second thickness is defined between the first face and the bulbous surface of the second face, and wherein the second thickness ranges from about 7 mm to about 50 mm, and
wherein the first thickness and the second thickness are not equivalent so as to result in the augment member having a non-uniform thickness, wherein at least one width of the second face is defined between the anterior side of the augment member and the posterior side of the augment member, wherein the at least one width of the second face is in a range of from about 20 mm to about 26 mm, wherein a length of the second face is defined between the proximal end of the augment member and the distal end of the augment member, wherein the length of the second face is in a range of from 20 mm to 60 mm, and wherein, when the augment member is positioned (a) between a proximal end of a humerus of a patient and a deltoid muscle of a shoulder joint of the patient, (b) such that the first face contacts bone of the humerus across the entirety of the first face and (c) such that the at least one width of the second face and the length of the second face define a muscle contact area, the second face is configured to contact the deltoid muscle while the shoulder joint moves through a range of motion.

2. The prosthetic augment of claim 1 wherein the augment member comprises at least one of cobalt chrome, stainless steel, titanium, titanium alloys, carbon fiber, ceramic, PMMA bone cement, plastics, or bone graft.

3. The prosthetic augment of claim 1 wherein the augment member further comprises at least one screw hole configured for a locking bone screw.

4. The prosthetic augment of claim 1 wherein the first face of the augment member is contoured.

5. The prosthetic augment of claim 1 wherein the augment member has bilateral symmetry.

6. The prosthetic augment of claim 1 wherein an edge of the augment member is curved.

7. The prosthetic augment of claim 1 wherein the augment member is configured so that, in vivo, a tension of the muscle is increased.

8. The prosthetic augment of claim 1 wherein the augment member is configured so that, in vivo, a moment arm of the muscle is increased.

9. The prosthetic augment of claim 1 wherein the augment member is configured so that, when the augment member is engaged with a proximal humerus in a shoulder joint, the bulbous surface results in a deltoid wrapping angle being increased by a value of about 24° as compared to a shoulder joint without the augment member.

10. The prosthetic augment of claim 1 wherein the augment member is configured so that, when the augment member is engaged with a proximal humerus in a shoulder joint having a reverse shoulder prosthesis, the bulbous surface results in a deltoid wrapping angle being increased by a value between about 22° to about 41° as compared to a shoulder joint having a reverse shoulder prosthesis without the augment member.

11. The prosthetic augment of claim 1, wherein the augment member is configured to engage the bone such that a center of rotation of the bulbous surface of the augment member approaches that of a native joint.

12. The prosthetic augment of claim 1, wherein the prosthetic augment is configured such that, when the prosthetic augment is positioned between a proximal end of a humerus of a patient and a deltoid muscle of the patient and is engaged to the humerus of the patient, a compression force by the deltoid muscle into the shoulder joint is induced so as to stabilize the shoulder joint of the patient.

13. The prosthetic augment of claim 1, wherein the prosthetic augment is configured such that, when the prosthetic augment is positioned between a proximal end of a humerus of a patient and a deltoid muscle of the patient and is engaged to the humerus of the patient, a muscle force required from the deltoid to produce a torque necessary for a desired action is reduced.

* * * * *